United States Patent
Potier et al.

(10) Patent No.: US 9,512,176 B2
(45) Date of Patent: Dec. 6, 2016

(54) AGE INHIBITORS

(75) Inventors: Pierre Potier, Paris (FR); Guy Jean Marie Potier, legal representative, Paris (FR); Marie-Claude Denise Michele Zelveyan, legal representative, Asnieres (FR); Catherine Marie Germaine Magnan, legal representative, Cabries (FR); Odette Drion, legal representative, Paris (FR); Nobumichi Andre Sasaki, Flesselles (FR); Maria Concepcion Achab Garcia Alvarez, Gif S/Yvette (FR); Qian Wang-Zhu, Gif S/Yvette (FR); Lioudmila Ermolenko, Paris (FR); Joanna Bakala, Paris (FR); Gisele Franck, Cachan (FR); Naima Bakrim Nhiri, Orsay (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/437,491

(22) Filed: Apr. 2, 2012

(65) Prior Publication Data
US 2012/0252866 A1  Oct. 4, 2012

Related U.S. Application Data

(63) Continuation of application No. 11/909,761, filed as application No. PCT/EP2006/061191 on Mar. 30, 2006, now abandoned.

(30) Foreign Application Priority Data

Mar. 31, 2005 (FR) ..................... 05 03176

(51) Int. Cl.
*C07K 5/068* (2006.01)
*A61K 38/00* (2006.01)
*C07K 5/09* (2006.01)

(52) U.S. Cl.
CPC ......... *C07K 5/06086* (2013.01); *C07K 5/0815* (2013.01); *A61K 38/00* (2013.01)

(58) Field of Classification Search
None
See application file for complete search history.

(56) References Cited

U.S. PATENT DOCUMENTS

| 4,758,583 | A | 7/1988 | Cerami et al. |
| 4,900,747 | A | 2/1990 | Vlassara et al. |
| 4,908,446 | A | 3/1990 | Ulrich et al. |
| 5,629,174 | A | 5/1997 | Sundelin et al. |
| 5,780,588 | A | 7/1998 | Pettit et al. |
| 6,083,758 | A | 7/2000 | Imperiali et al. |
| 6,337,350 | B1 | 1/2002 | Rahbar et al. |
| 6,605,642 | B2 | 8/2003 | Rahbar et al. |
| 6,693,106 | B2 | 2/2004 | Rahbar et al. |
| 6,787,566 | B2 | 9/2004 | Rahbar |
| 2003/0135023 | A1 | 7/2003 | Demuth et al. |
| 2003/0215406 | A1 | 11/2003 | Schreiner et al. |
| 2004/0266687 | A1* | 12/2004 | Hembrough et al. .......... 514/12 |
| 2005/0065090 | A1* | 3/2005 | Ludin .................... C07K 14/78 |
| | | | 514/9.3 |

FOREIGN PATENT DOCUMENTS

| EP | 0 333 071 | 9/1989 |
| EP | 0 804 452 B1 | 11/1997 |
| WO | WO 91/18523 | 12/1991 |
| WO | WO 92/14456 | 9/1992 |
| WO | WO9214456 | * 9/1992 ............. A61K 31/18 |
| WO | WO 93/04690 | 3/1993 |

(Continued)

OTHER PUBLICATIONS

Singh et al., Advanced Glycation end-products: a review, Dibetologia (2001) 44:129-146.*
McLellan et al., Analytical Biochemistry 206, 17-23 1992.*
Mutschler et al. Drug Actions, CRC Press 1995, p. 31.*
Bos & Meinardi, The 500 Dalton rule for skin penetration of chemical compounds and drugs, Exp Dermatol 2000:9, 165-169.*
The Myth of Antioxidants, Melina Wenner Moyer, Scientific American, Feb. 2013, pp. 62-67.*
Paul J. Thornally, Protein and nucleotide damage by glyoxal and methylglyoxal in physiological systems—role in ageing and disease, Drug Metab. Drug Interact 2008; 23(1-2); 125-150.*

(Continued)

*Primary Examiner* — Lianko Garyu
*Assistant Examiner* — Joseph Fischer
(74) *Attorney, Agent, or Firm* — Alston & Bird LLP

(57) ABSTRACT

The invention relates to a compound having general formula I, wherein: X represents $CH_2$, $C=O$, $C=S$ or CHOH, $R_1$ represents an amino acid optionally substituted by one or more halogen atoms, or by one or more $CF_3$ groups and n=0.1 or 2, or $R_1$ represents a peptide containing two amino acids, each amino acid being optionally substituted by one or more halogen atoms, or by one or more $CF_3$ groups and n=0 or 1, or $XR_1$ represent $PO_3H$ or $SO_3H$ and n=0.1 or 2; $R_2$ represents H, XR1, an alkyl group at $C_1$-$C_6$, an aralkyl group at $C_1$-$C_6$ or an aryl group, whereby the alkyl, aralkyl and aryl groups can be substituted by an amine $NH_2$, a carboxylic group COOH, one or more halogen atoms.

(I)

$$H_2N \diagdown \diagup R_2$$
$$| $$
$$(CH_2)_n$$
$$| $$
$$H_2N \diagup \diagdown X \diagdown R_1$$

10 Claims, 11 Drawing Sheets

(56) References Cited

FOREIGN PATENT DOCUMENTS

| | | |
|---|---|---|
| WO | WO 93/10677 | 6/1993 |
| WO | WO 93/13806 | 7/1993 |
| WO | WO 95/03318 | 2/1995 |
| WO | WO 96/23225 | 8/1996 |
| WO | WO 96/38472 | 12/1996 |
| WO | WO 01/76584 A2 | 10/2001 |
| WO | WO 01/96373 A2 | 12/2001 |
| WO | WO 01/96373 A3 | 12/2001 |
| WO | WO 02/092773 A2 | 11/2002 |
| WO | WO 02/092773 A3 | 11/2002 |
| WO | WO 02/100344 A2 | 12/2002 |
| WO | WO 03/033664 A2 | 4/2003 |
| WO | WO 03/084469 A2 | 10/2003 |
| WO | WO 03/084469 A3 | 10/2003 |
| WO | WO 2004/002418 A2 | 1/2004 |

OTHER PUBLICATIONS

Ahmed, Review Advance glycation endproducts—role in pathology of diabetic complications, Diabetics Research and Clinical Practice, 67 (2005) 3-21.*

Suzanne M. de la Monte and Jack R. Wands, Alzheimer's Disease is Type 3 Diabetes—Evidence Reviewed, J. Diabetes Science and Tech., vol. 2, Issue 6, Nov. 2008, 1101-1113.*

Angeloni et al., Role of Methylglyoxal in Alzheimer's Disease, BioMed Res. Intl, vol. 2014, art ID 238485, 12 pages, 2014.*

Alan R. Hipkiss, Parkinson's Disease and Type-2 Diabetes: Methylglyoxal may be a Common Causal Agent; Carnosine could be Protective, Mo. Med Ther 2012, 1:2, 6 pages 2012.*

International Search Report for PCT/EP2006/061191 filed Mar. 30, 2006.

International Search Report for FR 0503176, filed Mar. 31, 2005.

Sigma-Aldric, Dipeptides. 2011 [online], [retrieved on Oct. 31, 2011] Retrieved from the Sgima Aldrich biochemical catalog available on the Internet <URLhttp://www.sigmaaldrich.com/life-science/biochemical/biochemical-products.printerview.html?TablePage=16193112>.

Guest Editorial; Intervention Against the Maillard Reaction In Vivo; Archives of Biochemistry and Biophysics 419 (2003) 1-15.

Anderson, Melissa M., et al.; The Myeloperoxidase System of Human Phagocytes Generates N-(Carboxymethyl) Lysine on Proteins: A Mechanism for Producing Advanced Glycation End Products at Sites of Inflammation; The Journal of Clinical Investigation, Jul. 1999, vol. 104, No. 1, pp. 103-113.

Battah, Sinan, et al.; Kinetics and Mechanism of the Reaction of Metformin With Methylglyoxal; International Congress Series 1245 (2002) 355-356.

Beisswenger, P., et al.; Metformin Inhibition of Glycation Process; Diabetes Metab 2003-29-6S95-6S103.

Blaha, K. et al.; Basic Polypeptides as Histone Models: Synthesis and Conformation of (α,ω-Diaminoacyl-Alanyl-Glycyl) Sequential Polymers and Their Complexes With DNA; Collection Czechoslov, Chem. Commun. (vol. 42) (1977); pp. 2555-2568.

Brownlee, Michael M.D.; Advanced Protein Glycosylation in Diabetes and Aging; Annu. Rev. Med. 1995, 46:223-34; Copyright © 1995 by Annual Reviews, Inc.

Brownlee, M., et al.; Aminoguanidine Prevents Diabetes-Induced Arterial Wall Protein Cross-Linking; Science, vol. 232, Jun. 27, 1986, pp. 1629-1632.

Bucala, Richard M.D., et al.; Advanced Glycosylation End Products in Diabetic Complications; Diabetes Review, vol. 3, No. 2, 1995, pp. 258-268.

Bucala, Richard M.D., et al; Advanced Glycosylation End Products in Diabetic Renal and Vascular Disease; American Journal of Kidney Diseases; vol. 26, No. 6, Dec. 1995, pp. 875-888.

Chiarelli, F., et al.; Advanced Glycation End-Products in Diabetes Mellitus, With Particular Reference to Angiopathy; Diab. Nutr. Metab. 13: 192-199, 2000.

Frye, Elizabeth Brinkmann, et al.; Role of the Maillard Reaction in Aging of Tissue Proteins; The Journal of Biological Chemistry; vol. 273, No. 30, Issue of Jul. 24, pp. 18714-18718.

Hipkiss, Alan R.; Molecules in Focus—Carnosine, a Protective, Anti-Ageing Peptide?; The International Journal of Biochemistry & Cell Biology 30 (1998) 863-868.

Jones, Raymond C.F. and Ward, Gary J.; Amide Bond Isosteres: Imidazolines in Pseudopeptide Chemistry; Tetrahedron Letters, vol. 29, No. 31, pp. 3853-3856, 1988, Printed in Great Britain.

Kasina, Sudhakar, et al.; Tissue Distribution Properties of Technetium-99m-Diamide-Dimercaptide Complexes and Potential Use as Renal Radiopharmaceuticals; J. Med. Chem., 1986, 29, pp. 1933-1940.

Kume, Shuichi, et al.; Immunohistochemical and Ultrastructural Detection of Advanced Glycation End Products in Atherosclerotic Lesions of Human Aorta With a Novel Specific Monoclonal Antibody; American Journal of Pathology, vol. 147, No. 3, Sep. 1995, pp. 654-667.

Lorenzi, M., et al.; Early Cellular and Molecular Changes Induced by Diabetes in the Retina; Diabetologia (2001) 44:791-804.

Luth, Hans-Joachim, et al.; Age- and Stage-Dependent Accumulation of Advanced Glycation End Products in Intracellular Deposits in Normal and Alzheimer's Disease Brains; Cerebral Cortex Feb. 2005, 15:211-220.

Makita, Zenji, M.D., et al.; Advanced Glycosylation End Products in Patients With Diabetic Nephropathy; The New England Journal of Medicine, Sep. 19, 1991, pp. 836-842.

McLellan, Antony C.; Glyoxalase System in Clinical Diabetes Mellitus and Correlation With Diabetic Complications; Clinical Science (1994) 87, 21-29.

Metz, Thomas O., et al.; Pydridoxamine, an Inhibitor of Advanced Glycation and Lipdxidation Reactions: A Novel Therapy for Treatment of Diabetic Complications; Archives of Biochemistry and Biophysics 419 (2003) 41-49.

Micans, Phil PharmB; Anti-Ageing Conference London 2004; Offshore Phramacy; Aminoguanidine: Age Inhibitor by Phil Micans PharmB.

Miyata, Toshio, et al.; Alterations in Nonenzymatic Biochemistry in Uremia: Origin and Significance of "Carbonyl Stress" in Long-Term Uremic Complications: Kidney International, vol. 55 (1999), pp. 389-399.

Munch, G., et al.; Anti-Ageing Defences Against Alzheimer's Disease; The Enzymatic Defence against Glycation in Health, Disease and Therapeutics, pp. 1397-1399.

Nagaraj, Ramanakoppa H., et al.; Protein Cross-Linking by the Maillard Reaction; The Journal of Biological Chemistry; vol. 271, No. 32, Issue of Aug. 9, pp. 19338-19345, 1996.

Oturai, Peter S., et al.; Effects of Heparin and Aminoguanidine on Glomerular Basement Membrane Thickening in Diabetic Rats; APMIS 104: 259-264, 1996.

Porta, M., et al.; Diabetic Reinopathy, a Clinical Update; Diabetologia (2002) 45:1617-1634.

Rahbar, Samuel, et al., Novel Inhibitors of Advanced Glycation Endproducts; Archives of Biochemistry and Biophysics 419 (2003) 63-79.

Rinaldi, Augusto et al.; Oxidation of Meso-Diaminosuccinic Acid, a Possible Natural Substrate for D-Aspartate Oxidase; Eur. J. Biochem. 117, 635-638 (1981).

Sajithlal, G.B., et al.; Effect of Curcumin on the Advanced Glycation and Cross-Linking of Collagen in Diabetic Rats; Biochemical Pharmacology, vol. 56, pp. 1607-1614, 1998.

Shinoda, Ichizo, et al.; A New Salty Peptide, Ornithyl-β-Alanine Hydrochloride; Peptide Chemistry 1983: E.Munekata(Ed.); Protein Research Foundation, Osada (1984).

Soulis, T., et al., A Novel Inhibitor of Advanced Glycation End-Product Formation Inhibits Mesenteric Vascular Hypertrophy in Experimental Diabetes; Diabetologia (1999) 42: 472-479.

Stitt, Alan William, et al.; Elevated Age-Modified APOB in Sera of Euglycemic, Normolipidemic Patients With Atherosclerosis: Relationship to Tissue Ages; ©, The Picower Institute Press; Molecular Medicine, vol. 3, No. 9, Sep. 1997, pp. 617-627.

(56) References Cited

OTHER PUBLICATIONS

Stracke, H., et al., Efficacy of Benfotiamine Versus Thiamine on Function and Glycation Products of Peripheral Nerves in Diabetic Rats; Experimental and Clinical Endocrinology & Diabetes 109 (2001) 330-336.
Tada et al. *L-Ornithyltaurine, a New Salty Peptide*, J. Agric. Food Chem., vol. 32, No. 5, (1984) pp. 992-996.
Tada, Makoto, et al.; L-Ornithyltaurine, a New Salty Peptide; © 1984 American Chemical Society.
Thornalley, Paul J.; Glycation in Diabetic Neuropathy: Characteristics, Consequences, Causes, and Therapeutic Options; International Review of Neurobiology, vol. 50, pp. 37-57.
Ulrich, Peter, et al.; Protein Glycation, Diabetes, and Aging; Downloaded from rphr.endojournals.org on Dec. 2, 2007; Copyright © 2001 by the Endocrine Society.
Webster, Julie, et al.; The Carbonyl Scavengers Aminoguaridine and Tenilsetam Protect Against the Neurotoxic Effects of Methylglyoxal; Neurotoxicity Research (2005), 7(1,2), 95-101; Publisher F.P. Graham Publishing Co., CODEN NURRFI ISSN: 1029-8428.
Wondrak, Georg T., et al.; Identification of α-Dicarbonyl Scavengers for Cellular Protection Against Carbonyl Stress; Biochemical Pharmacology 63 (2002) 361-373.
Ziegler, Dan, et al.; Clinical Trials for Drugs Against Diabetic Neuropathy: Can We Combine Scientific Needs With Clinical Practicalities?; International Review of Neurobiology, vol. 50, pp. 431-463.

\* cited by examiner

AGE INHIBITORS

CROSS REFERENCE TO RELATED APPLICATIONS

This application is a continuation application of U.S. patent application Ser. No. 11/909,761, filed Dec. 5, 2007, which is a national phase of PCT/EP2006/061191 filed Mar. 30, 2006 which claims the benefit of French Application No. 0503176 filed Mar. 31, 2005, each of which is hereby incorporated herein in its entirety by reference.

BACKGROUND

The Maillard reaction, non-enzymatic glycation, is initiated by the condensation of an amino group present in proteins with a compound containing a carbonyl group, generally a sugar. A multitude of products, referred to as "advanced glycation end-products" (AGEs), result from the latter stages of this complex process. The consequence of the formation of these AGEs is protein cross-linking. Such cross-links have been observed in long-lived proteins such as collagen, lens crystalline, fibronectin, tubulin, myelin, laminin, actin, hemoglobin, albumin and the lipids associated with low-density lipoproteins (LDLs). AGE-modified proteins increase progressively with age and it is believed that they contribute to the normal tissue remodeling. Moreover, enhanced formation and accumulation of AGEs have been linked to the development of cataracts (Nagaraj et al., *J. Biol. Chem.* (1996) 271, 19338), uraemia (Miyata et al., *Kidney Int.* (1999) 55, 389), atherosclerosis (Kume et al., *Am. J. Pathol.* (1995) 147, 654; Stitt et al., *Mol. Med.* (1997) 3, 617), Alzheimer's disease (Münch et al., *Biochem. Soc. Trans.* (2003) 31 (6), 1397; Lüth et al., *Cerebral Cortex* (2005) 15(2), 211), Parkinson's disease (Webster et al., *Neurotoxicity Res.* (2005)/(172), 95), inflammatory disease (Anderson et al., *J. Clin. Invest.* (1999) 104, 103), age-related rheumatic disorders and, above all, clinical complications of diabetes mellitus (Brownlee, M. *Ann. Rev. Med.* (1995) 461, 223; Brinkmann et al., *J. Biol. Chem.* (1998) 273, 18714). Diabetic patients whose glycemia is elevated and persistent have an increased level of cross-linked proteins, which leads to tissue damage via modification of the structure and function of the proteins involved. Moreover, AGEs bind to membrane receptors and stimulate cellular responses. Since Maillard's discovery at the beginning of the last century, it has been believed that glucose is the sugar that participates in the cross-linking reaction. More recently, however, attention has been focused on α-dicarbonyl compounds, such as methylglyoxal (MG), glyoxal (GO) and 3-deoxyglucosone (3-DG), as active crosslinkers in vivo and in vitro. It is believed that the principal source of MG is the non-enzymatic dephosphorylation of triose-dihydroxyacetone phosphate and glyceraldehyde-3-phosphate, which are glucose metabolites. MG can also be formed by the spontaneous decomposition of triose phosphates or by the metabolism of threonine or acetone. Some studies have also confirmed the generation of α-dicarbonyls via glucose auto-oxidation. It is believed that α-dicarbonyls can be generated during the transformation of a ketoamine, known as the Amadori product, a key intermediate in the Maillard reaction. This ketoamine is itself generated by the transformation of the Schiff-base adduct, which is initially formed during the reaction of glucose with an amine. In addition, it has been reported that bacteria produce MG. Lipid peroxidation of polyunsaturated fatty acids also yields reactive carbonyl compounds, such as MG and GO and those characteristic of lipids, such as malondialdehyde (MDA) and 4-hydroxynonenal. In general, such highly reactive dicarbonyls bind to the amino, guanidine and sulfhydryl groups of proteins and irreversibly form AGEs such as $N_\epsilon$-(1-carboxyethyl)lysine (CEL), $N_\epsilon$-(1-carboxymethyl)lysine (CML), methylglyoxal-derived hydroimidazolone $N_\delta$-(5-hydro-5-methyl-4-imidazolon-2-yl)-ornithine (MG-$H_1$), glyoxal-derived hydroimidazolone (G-$H_1$), argpyrimidine, glyoxal-derived lysine dimer, 1,3-di($N^\epsilon$-lysino)imidazolium salt (GOLD), and methylglyoxal-derived lysine dimer, 1,3-di($N^\epsilon$-lysino)-4-methylimidazolium salt (MOLD). The in vivo mechanism of action of these α-dicarbonyl compounds has been studied in an effort to understand the progression of the Maillard reaction in the organism. In diabetic subjects, increased formation and accumulation of AGEs occurs, thus leading to a series of long-term complications of diabetes such as nephropathy, retinopathy, neuropathy, ulcers and microvascular and macrovascular complications (Bucala et al., *Diabetes Reviews* (1995) 3, 258; Ulrich et al., *Recent Prog. Horm. Res.* (2001) 56, 1; Porta et al., *Diabetologia* (2002) 45, 1617; Lorenzi et al., *Diabetologia* (2001) 44, 791; Ziegler et al., *Int. Rev. Neurobiol.* (2002) 50, 451; Thornalley, P. J. *Int. Rev. Neurobiol.* (2002) 50, 37; Chiarelli et al., *Diab. Nutr. Metab.* (2000) 13, 192). More particularly, renal tissue damage caused by AGEs leads to the progressive loss of renal functioning (Makita Z., et al., *N. Eng. J. Med.* (1991) 325, 836). Indeed, among diabetic patients (type 1 and type 2), plasma concentration of methylglyoxal proved to be two to six times higher than that of normal subjects (McLellan et al., *Clin. Sci.* (1994) 87, 21).

Oxidative stress is another factor associated with ageing and with the current criteria for chronic diseases such as diabetes, atherosclerosis and related vascular diseases, rheumatoid polyarthritis and uremia. Oxidative stress is defined as a significant imbalance between antioxidant and oxidant generation systems. An increase in oxidative stress can have a profound effect on the modification of lipoproteins and on transcription, as well as on the functioning and metabolism of cells. Oxidative stress can appear via several mechanisms associated with the overproduction of oxygen radicals, such as the auto-oxidation of glucose and of glycated proteins and the glycation of antioxidant enzymes. Indeed, it has been reported that MG generates reactive oxygen species (ROS) (free radicals) during glycation reactions. Thus, it can be said that oxidative stress and AGE formation are inseparably intertwined.

Normally, the glyoxalase system (glyoxalase I and glyoxalase II) and aldose reductase catalyze the detoxification of these α-dicarbonyls into D-lactate, glycolate and acetol. However, a dysfunction of this detoxification metabolism leads to an increase in the quantity of AGEs formed by highly reactive α-dicarbonyls in the organism.

Inhibition of AGE formation can delay the progression of the physiopathology of AGE-related diseases and improve quality-of-life during ageing. It can thus be assumed that the pharmacological scavenging of α-dicarbonyl compounds is a valuable therapeutic strategy in the prevention of complications of diabetes. A large number of documents exist concerning the fact that an early stage pharmacological intervention against the long-term consequences of cross-linking prevents the development of later complications of diabetes. Even if AGE-formation inhibitors can not cure the underlying pathological process, they should delay the development of complications resulting from the fundamental disorders. Among the drugs specifically developed as AGE-formation inhibitors, aminoguanidine (pimagedine, AG) is the most studied and most used agent. AG is a nucleophilic compound with two key reactive functions, namely the nucleophilic hydrazine function —NHNH$_2$ and the α-dicarbonyl directing guanidine function —NH—C (=NH)NH$_2$. These two functional groups bound together jointly form a reactive bifunctional scavenger of methylglyoxal, glyoxal and 3-desoxyglucosone (Brownlee, et al., *Science* (1986) 232, 1629). Although the beneficial effects of AG against the complications of diabetes have been largely confirmed in the diabetic rat model, AG is a well-known selective inhibitor of nitrogen monoxide (NO) and a clinical trial related to the prevention of the progression of diabetic nephropathy by AG was abandoned due to safety concerns (Oturai et al., *APMIS* (1996) 104, 259; Monnier, V. M. *Arch. Biochem. Biophys.* (2003) 419, 1). Pyridoxamine (pyridon) is another agent able to prevent complications in the diabetic rat with greater effectiveness than that of aminoguanidine, and it is able to scavenge lipid peroxidation products and α-dicarbonyl compounds (Metz et al., *Archives of Biochemistry and Biophysics* (2003) 419, 41). Metformin, an antihyperglycemic drug widely used in the management of type 2 diabetes, also reduces levels of methylglyoxal and glyoxal both in vivo and in vitro by forming triazepinones (Beisswenger et al., *Diabetes Metab.* (2003) 29, 6895). However, AG proved to be a much better scavenger (by a factor of 450) of methylglyoxal compared with metformin (Battah et al., *Intern. Congress Series* 1245 (2002) 355). Other compounds possessing AGE-formation inhibitory activity include D-penicillamine (Wondrak G et al., *Biochem. Pharmacol.* (2002) 63, 361), LR-90, methylene bis(4,4'-(2-chlorophenylureidophenoxyisobutyric acid)) (Rahbar et al., *Arch. Biochem. Biophys.* (2003) 419, 63), thiamin (Benfotiamine) (Stracke et al., *J. Exp. Clin. Endocrinol. Diabetes* (2001) 109, 330), carnosine (β-alanyl-L-histidine), a natural dipeptide widely distributed throughout mammalian tissues (Hipkiss A. R., *Int. J. Biochem. Cell Biol.* (1998) 30, 863), curcumin (Sajithlal et al., *G. Biochem. Pharmacol.* (1998) 56, 1607) another natural compound isolated from *Curcuma longa*, 2,3-diaminophenazine (NNC39-0028) (Soulis, et al., *Diabetologia* (1999) 42, 472). Given the marked impact of AGEs on quality-of-life during ageing, there remains a need to develop efficient agents that can scavenge highly reactive α-dicarbonyl compounds such as methylglyoxal, glyoxal and 3-desoxyglucosone and that have low cytotoxicity and low mutagenicity.

SUMMARY

In a surprising way, the present inventors have discovered a new class of compounds able to inhibit the formation of advanced glycation end-products by scavenging reactive α-dicarbonyl compounds.

Some of these compounds are already known as such but not with respect to their therapeutic application.

Thus, patent application WO02/100344 discloses the

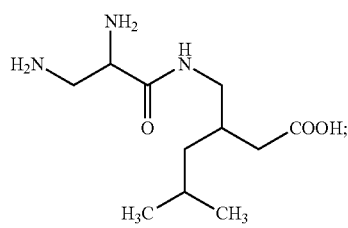

synthesis intermediate the article by Jones et al., (*Tetrahedron Letters* (1988), 29 (31), pages 3856-3856) discloses the synthesis intermediates

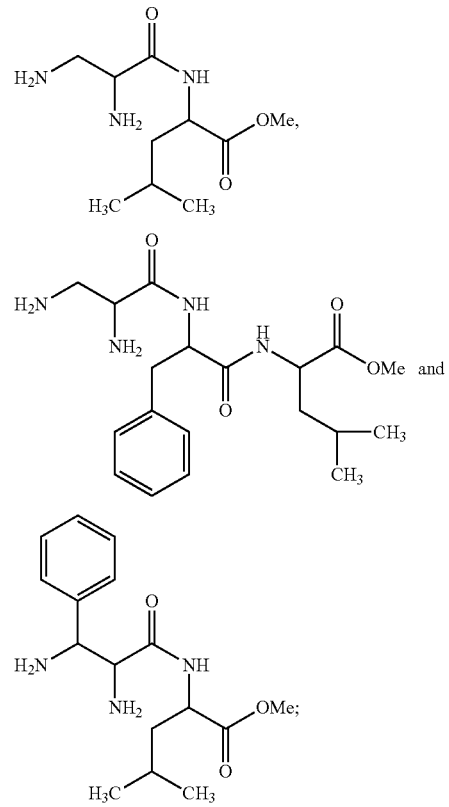

the article by Kasina et al., (*Journal of Medicinal Chemistry* (1986), 29 (10), pages 1933-1940) discloses the synthesis intermediate

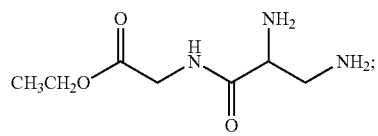

the article by Tada et al., (*Journal of Agricultural And Food Chemistry* (1984), 32 (5), pages 992-996) discloses the flavor of peptides of formula I wherein R$_2$ represents a hydrogen atom, X represents C=O, R$_1$ represents —NH—(CH$_2$)$_m$—COOH and m=1, 2 or 3; the article by Shinoda et al., (*Peptide Chemistry* (1984), volume date 1983, 21st, pages 43-46) discloses the peptides

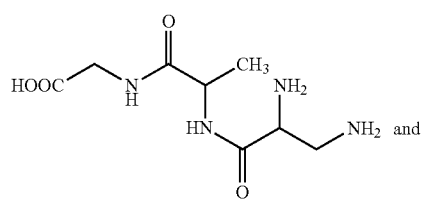

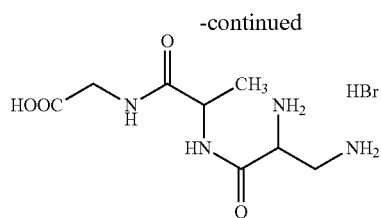

having a salty flavor.

Only the patent application WO 2004/002418 discloses the peptide of formula

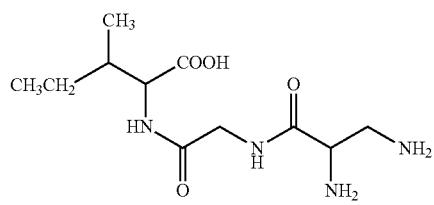

and its therapeutic application. This document does not, however, indicate that this peptide is an AGE inhibitor.

Additionally, derivatives analogous to those discovered by the inventors, in particular 2,3-diaminopropionic acid (DAPA), have been disclosed in a patent application (WO 92/14456). DAPA would be highly susceptible to decarboxylation by ornithine decarboxylase, a ubiquitous enzyme which participates in the synthesis of a large number of polyamines leading to ethylenediamine and/or 2-aminoacetamide. With a view to facilitate the elimination via the urine of the condensation products of α-dicarbonyl compounds and the scavenging agents, the presence of an acid functional group such as —COOH or $SO_3H$ in the scavenger molecules is a crucial requirement. Otherwise, the condensation products would remain in circulation by renal tubular reabsorption mechanisms with the risk of a release α-dicarbonyls following another metabolic reaction. From the point of view of ornithine decarboxylase metabolism, the compounds discovered by the inventors of the present application can be used as agents, which are more effective than DAPA, to scavenge reactive α-dicarbonyl compounds such as methylglyoxal, glyoxal and 3-desoxyglucosone by forming adducts which are eliminated in the urine. Indeed, DAPA prevents the modification of insulin by MG, as is illustrated in FIG. 1. However, FIG. 7 demonstrates that its cytotoxicity is higher and that its effectiveness in protecting cells lower (68% cell survival when incubated with MG) compared with L-DAPA-L-Val (93%), L-DAPA-L-Leu (81%) and L-DAPA-L-Ile (79%), compounds according to the present invention. In addition, DAPA appears to be mutagenic.

Thus, the present invention relates to a compound of following general formula I:

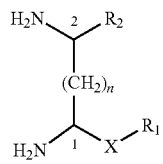

I wherein:

X represents $CH_2$, C=O, C=S or CHOH, $R_1$ represents an amino acid, optionally substituted by one or more halogen atoms, advantageously fluorine, or by one or more $CF_3$ groups, and n=0, 1 or 2 or X represents $CH_2$, C=O, C=S or CHOH, $R_1$ represents a peptide containing two amino acids, each amino acid being optionally substituted by one or more halogen atoms, advantageously fluorine, or one or more $CF_3$ groups, and n=0 or 1 or $XR_1$ represents $PO_3H$ or $SO_3H$ and n=0, 1 or 2;

$R_2$ represents H, $XR_2$, a $C_1$-$C_6$ alkyl group, a $C_1$-$C_6$ aralkyl group or an aryl group, the alkyl, aralkyl and aryl groups being able to be substituted by an amine ($NH_2$), a carboxylic group (COOH), one or more halogen atoms, advantageously fluorine, or one or more $CF_3$ groups;

or the pharmaceutically acceptable addition salts, isomers, enantiomers and diastereoisomers of same, as well as mixtures of same, with the exception of compounds wherein $R_2$ represents a hydrogen atom, X represents C=O, $R_1$ represents —NH—$(CH_2)_m$—COOH and m=1, 2 or 3 and n=0, 1 or 2;

represented by the following formulas:

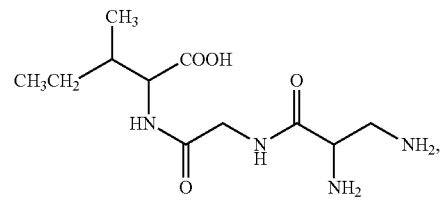

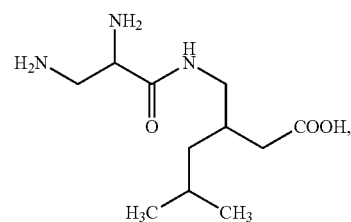

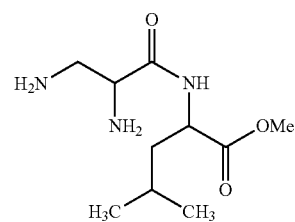

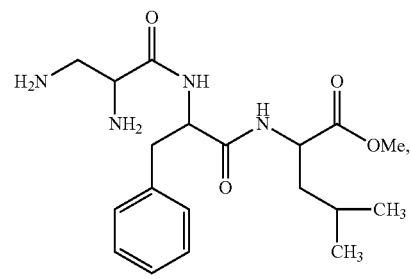

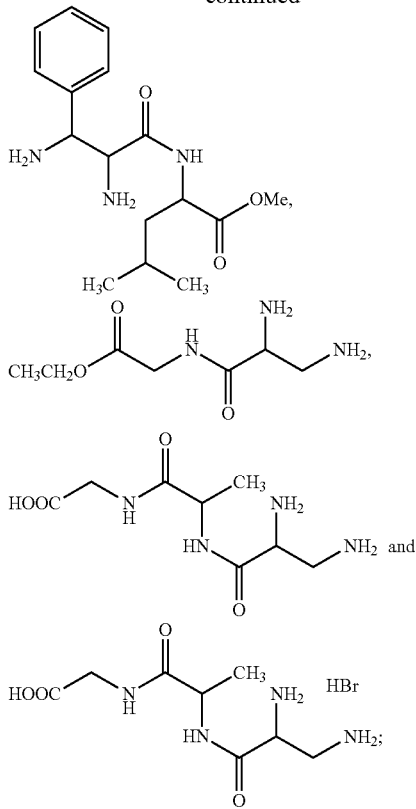

and the compounds L-ornithyl-taurine, L-diaminobutyryl-taurine and L-diaminopropionyl taurine.

In the sense of the present invention, the term "$C_1$-$C_6$ alkyl group" means any alkyl group of one to six carbon atoms, linear or branched. In particular, it can relate to a methyl, ethyl, n-propyl, isopropyl, n-butyl, isobutyl, sec-butyl, t-butyl, n-pentyl and n-hexyl group.

In the sense of the present invention, the term "aryl group" means one or more aromatic rings of five to eight carbon atoms, possibly adjoining or fused. In particular, the aryl group can be a phenyl or naphthyl group, advantageously phenyl.

In the sense of the present invention, the term "aralkyl group" means any aryl group as defined above, linked via an alkyl group as defined above. In particular, a benzyl group is an aralkyl group.

In the sense of the present invention, the "pharmaceutically acceptable addition salt" of a compound means any salt that is pharmaceutically acceptable and that has the desired pharmacological activity of the parent compound. Such salts comprise:
(1) acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphtalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; or (2) salts formed when an acid proton present in the parent compound either is replaced by a metal ion, for example an alkali metal ion, an alkaline earth metal ion or an aluminum ion; or coordinates with an organic or inorganic base. Acceptable organic bases include diethanolamine, ethanolamine, N-methylglucamine, triethanolamine, tromethamine and the like. Acceptable inorganic bases include aluminum hydroxide, calcium hydroxide, potassium hydroxide, sodium carbonate and sodium hydroxide.

Advantageous pharmaceutically acceptable salts are salts formed from hydrochloric acid, trifluoroacetic acid, dibenzoyl-L-tartaric acid and phosphoric acid.

It should be understood that all references to pharmaceutically acceptable salts include the solvent addition forms (solvates) or the crystalline forms (polymorphs), as defined herein, of the given acid addition salt.

The stereochemistry of the C-1 position of formula I (the carbon atom at the junction of the $NH_2$ and X groups) can be R or S or a mixture thereof. The stereochemistry of the C-2 position (the carbon atom at the junction of the $NH_2$ and $R_2$ groups) can be R or S or a mixture thereof.

In the sense of the present invention, "amino acids" means all natural α-amino acid residues (for example alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophane (Trp), tyrosine (Tyr) and valine (Val)) in D or L form, as well as non-natural amino acids (for example, β-alanine, allylglycine, tert-leucine, norleucine (Nle), 3-amino-adipic acid, 2-aminobenzoic acid, 3-aminobenzoic acid, 4-aminobenzoic acid, 2-aminobutanoic acid, 4-amino-1-carboxymethyl piperidine, 1-amino-1-cyclobutanecarboxylic acid, 4-aminocyclohexaneacetic acid, 1-amino-1-cyclohexanecarboxylic acid, (1R,2R)-2-aminocyclohexanecarboxylic acid, (1R,2S)-2-aminocyclohexanecarboxylic acid, (1S,2R)-2-aminocyclohexanecarboxylic acid, (1S,2S)-2-aminocyclohexanecarboxylic acid, 3-aminocyclohexanecarboxylic acid, 4-aminocyclohexanecarboxylic acid, (1R,2R)-2-aminocyclopentanecarboxylic acid, (1R,2S)-2-aminocyclopentanecarboxylic acid 1-amino-1-cyclopentanecarboxylic acid, 1-amino-1-cyclopropanecarboxylic acid, 4-(2-aminoethoxy)-benzoic acid, 3-aminomethylbenzoic acid, 4-aminomethylbenzoic acid, 2-aminobutanoic acid, 4-aminobutanoic acid, 6-aminohexanoic acid, 1-aminoindane-1-carboxylic acid, 4-aminomethyl-phenylacetic acid, 4-aminophenylacetic acid, 3-amino-2-naphthoic acid, 4-aminophenylbutanoic acid, 4-amino-5-(3-indolyl)-pentanoic acid, (4R,5S)-4-amino-5-methylheptanoic acid, (R)-4-amino-5-methylhexanoic acid, (R)-4-amino-6-methylthiohexanoic acid, (S)-4-amino-pentanoic acid, (R)-4-amino-5-phenylpentanoic acid, 4-aminophenylpropionic acid, (R)-4-aminopimeric acid, (4R,5R)-4-amino-5-hyroxyhexanoic acid, (R)-4-amino-5-hydroxypentanoic acid, (R)-4-amino-5-(p-hydroxyphenyl)-pentanoic acid, 8-aminooctanoic acid, (2S,4R)-4-amino-pyrrolidine-2-carboxylic acid, (2S,4S)-4-amino-pyrrolidine-2-carboxylic acid, azetidine-2-carboxylic acid, (2S,4R)-4-benzyl-pyrrolidine-2-carboxylic acid, (S)-4,8-diaminooctanoic acid, tert-butylglycine, γ-carboxyglutamate, β-cyclohexylalanine, citruline, 2,3-diamino propionic acid, hippuric acid, homocyclohexylalanine, moleucine, homophenylalanine, 4-hydroxyproline, indoline-2-carboxylic acid, isonipecotic acid, α-methyl-alanine, nicopetic acid, norvaline, octahydroindole-2-carboxylic acid, ornithine, penicillamine, phenylglycine (Phg), 4-phenyl-pyrrolidine-2-carboxylic acid, pipecolic acid, propargylglycine, 3-pyridinylalanine, 4-pyridinylalanine, 1-pyrrolidine-3-carboxylic acid, sarcosine, the statins, tetrahydroisoquinoline-1-carboxylic acid, 1,2,3,4-tetrahydroisoquinoline-3-carboxylic acid, tranexamic acid, 4,4-difluoro proline, 4-fluoro proline, alpha-(3,4-difluorobenzyl)-proline, gamma-(3,4-difluorobenzyl)-proline, alpha-(trifluoromethyl)phenylalanine, hexafluoroleucine, 5,5,5-trifluoroleucine, 6,6,6-trifluoronorleucine, 2-(trifluoromethyl)leucine, 2-(trifluoromethyl)norleucine, 4,4,4-trifluorovaline, 4,4,4,4', 4',4'-hexafluorovaline, pentafluorophenylalanine, 2,3-difluorophenylalanine, 2,4-difluorophenylalanine, 2,5-difluorophenylalanine, 2,6-difluorophenylalanine, 3,4-difluorophenylalanine, 3,5-difluorophenylalanine, 3,3-difluoro-3-(4-fluorophenyl)alanine, 2,3-difluorophenylglycine, 2,4-difluorophenylglycine, 2,5-difluorophenylglycine, 3,4-difluorophenylglycine, 4,4-difluoroethylglycine, 4,4,4-trifluoroethylglycine and hexafluoronorleucine). The term also includes natural and non-natural amino acids carrying a conventional amino protecting group (for example, an acetyl group, tert-butyloxycarbonyl, benzyloxycarbonyl or 9-fluorenylmethylcarbonyl), as well as natural and non-natural amino acids protected at the carboxylic end (advantageously by a $C_1$-$C_{18}$ alkyl group, an ester, a phenyl amide or benzyl amide or an amide, which, respectively, give a carboxylic end of the following formula: —CO($C_1$-$C_{18}$ alkyl), —COO($C_1$-$C_{18}$ alkyl), —CONHphenyl, CONHbenzyl, or CONH$_2$). Advantageously, the amino acid according to the present invention has its carboxylic end unprotected.

Advantageously, the amino acid according to the present invention has its carboxylic end protected in the form of a $C_1$-$C_{18}$ alkyl ester (—COO($C_1$-$C_{18}$ alkyl)), preferably a $C_{13}$-$C_{18}$ alkyl ester (—COO($C_{13}$-$C_{18}$ alkyl)).

Advantageously, the amino acid is linked to the X radical of the compound of formula I by the N-terminal end. Advantageously, the bond thus formed is as follows: —X—NH—R, wherein R represents the remainder of the amino acid molecule.

Advantageously, the amino acid according to the present invention is substituted by one or more halogen atoms (Br, Cl, I or F), advantageously fluorine, or one or more CF$_3$ groups. Advantageously, this substitution is present on the alkyl or aryl moiety of the amino acid. Even more advantageously, the nitrogen atom is not substituted. The principal advantages of substitution by a halogen atom, in particular by a fluorine atom, or by a CF$_3$ group relate to the bioavailability of the compounds obtained and, in particular, to improvements in their cell membrane permeation and binding characteristics.

Advantageously, the amino acid is selected among alanine, valine, isoleucine, proline, leucine, phenylalanine, glycine, β-alanine, norleucine, aspartic acid, lysine, or tert-leucine, advantageously among alanine, valine, isoleucine, proline, phenylalanine, leucine, norleucine or tert-leucine.

Advantageously, the phenyl radical of phenylalanine is substituted by one or more halogen atoms, advantageously fluorine, or by one or more CF$_3$ groups, advantageously in the para position, less advantageously in the ortho or meta position.

Advantageously, the butyl radical of norleucine is substituted by one or more halogen atoms, advantageously fluorine, or by one or more CF$_3$ groups.

In the sense of the present invention, the term "$C_1$-$C_{18}$ alkyl group" means any alkyl group of one to 18 carbon atoms, linear or branched. In particular, it can relate to a methyl, ethyl, n-propyl, isopropyl, n-butyl, isobutyl, sec-butyl, t-butyl, n-pentyl and n-hexyl group.

In the sense of the present invention, the term "peptide comprising two amino acids" means any sequence of two amino acids as defined below or of peptidyl residues. The sequence can be linear or cyclic. For example, a cyclic peptide can be prepared or can result from the formation of a disulfide bridge between two cysteine residues in a sequence. Advantageously, the peptide is linked to the remainder of the compound of formula I by the N-terminal end. Peptide derivatives can be prepared by any conventional method (in solution or solid phase) known in the art, such as those described in the examples below. The peptide sequences specifically described in the present application are written with the amino end on the left and the carboxylic end on the right. Advantageously, the peptide is selected among Ala-Gly, Ala-Ala, Ala-Pro or Ala-Val, advantageously among L-Ala-Gly, L-Ala-L-Ala, L-Ala-L-Pro or L-Ala-L-Val.

Advantageously, the compound according to the present invention is such that X represents C=O, CH$_2$ or C=S.

Advantageously, the compound according to the present invention is such that R$_2$ represents H or XR$_1$, advantageously XR$_1$.

In a specific embodiment, the compound according to the present invention is such that R$_1$ represents an amino acid, advantageously selected among alanine, valine, isoleucine, proline, leucine, norleucine, phenylalanine or tert-leucine.

Advantageously, the compound according to the present invention is such that X is C=O, n=0, and R$_1$ is alanine, valine, leucine, isoleucine, proline, norleucine, phenylalanine or tert-leucine.

Advantageously, the compound according to the present invention is such that R$_2$ is XR$_1$ or H and n=0.

In another specific embodiment of the invention, the compound according to the present invention is represented by the following general formula II:

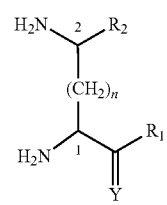

II wherein:
R$_1$ represents —NH—R$_3$—(C=O)R$_4$ or

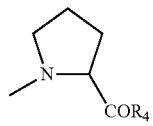

wherein
R$_3$ represents
a $C_1$-$C_{12}$ alkyl group, advantageously $C_1$-$C_6$, optionally substituted by one or more groups chosen among a halogen atom, advantageously fluorine, a —CF$_3$, phenyl, phenol, —COOH, amine or phenyl group substituted by one or more halogen atoms, advantageously fluorine, or by one or more CF$_3$ groups;

a phenyl group, optionally substituted by an amine, an OH group, one or more halogen atoms, advantageously fluorine, or one or more $CF_3$ groups and $R_4$ represents OH, $NH_2$, a $C_1$-$C_{30}$ alkoxy, advantageously $C_1$-$C_{20}$;

$R_2$ represents H, $COR_1$, or a $C_1$-$C_6$ alkyl group optionally substituted by one or more halogen atoms, advantageously fluorine, or by one or more $CF_3$ groups;

n=0, 1 or 2;

Y represents an oxygen or sulfur atom, advantageously an oxygen atom;

or the pharmaceutically acceptable addition salts, isomers, enantiomers and diastereoisomers of same, as well as mixtures of same.

In the sense of the present invention, the term "$C_1$-$C_{12}$ alkyl group" means any alkyl group of one to 12 carbon atoms, linear or branched. In particular, it can relate to a methyl, ethyl, n-propyl, isopropyl, n-butyl, isobutyl, sec-butyl, t-butyl, n-pentyl and n-hexyl group.

The term "$C_1$-$C_{30}$ alkoxy" means any —O—R radical, wherein R is a $C_1$-$C_{30}$ alkyl radical as defined herein. Examples of alkoxy radicals include, but are not limited to, methoxy, ethoxy, isopropoxy and the like.

Advantageously the compound according to the present invention is such that n=0.

Advantageously $R_2$=H or $COR_1$.

In a specific embodiment, the compound according to the present invention is selected among:

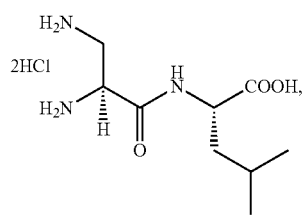
1

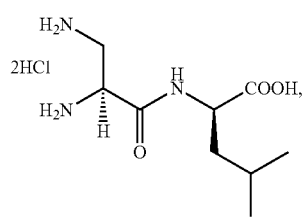
2

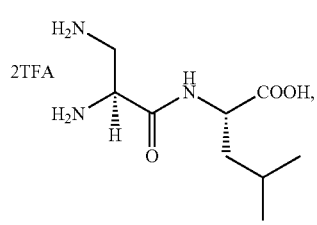
3

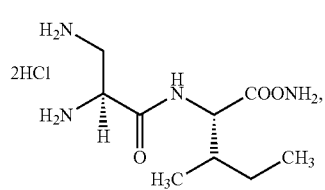
6

-continued

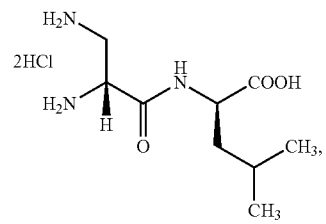
7

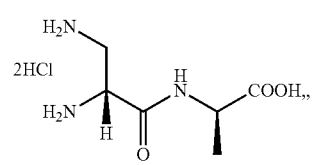
8

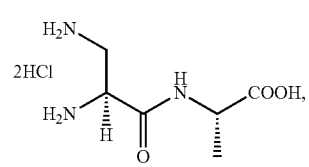
9

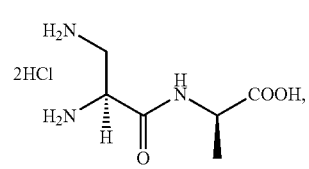
10

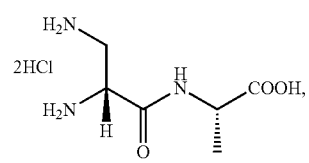
11

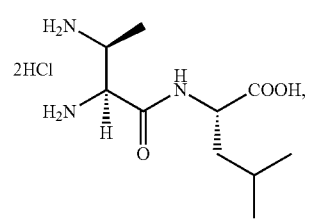
12

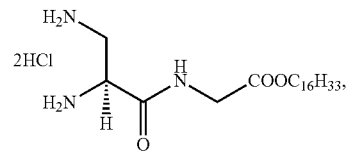
13

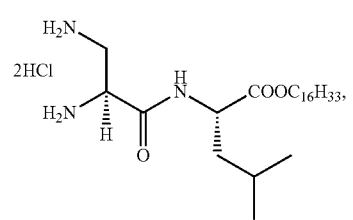
14

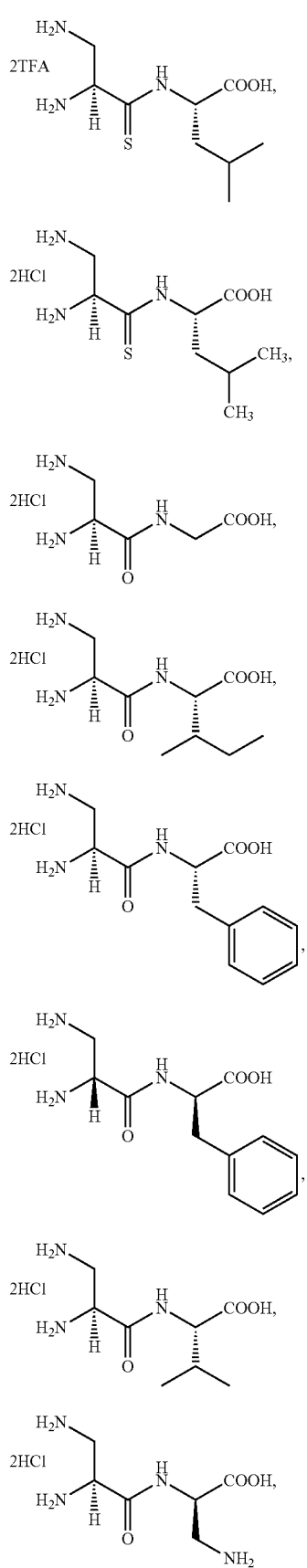

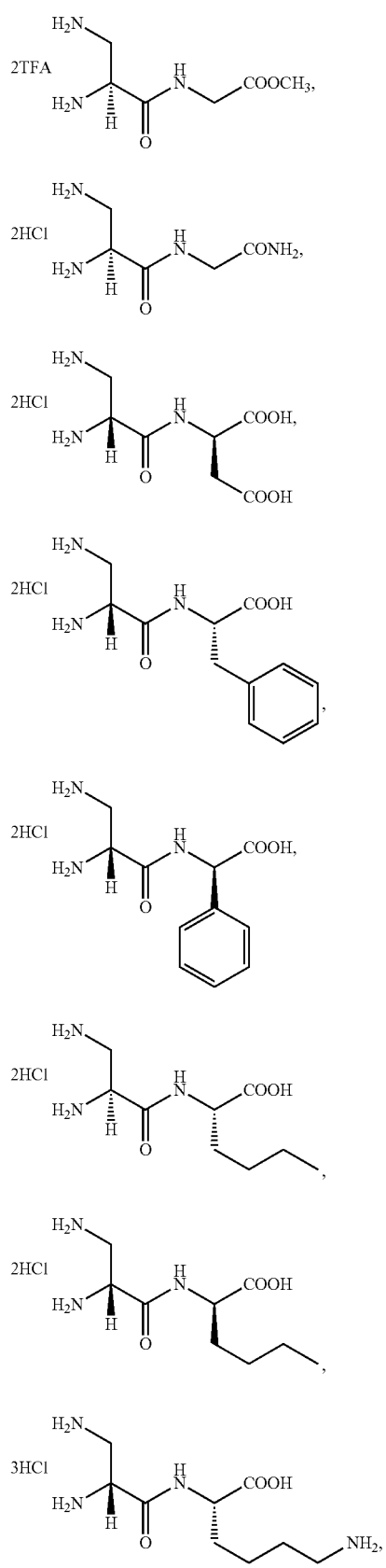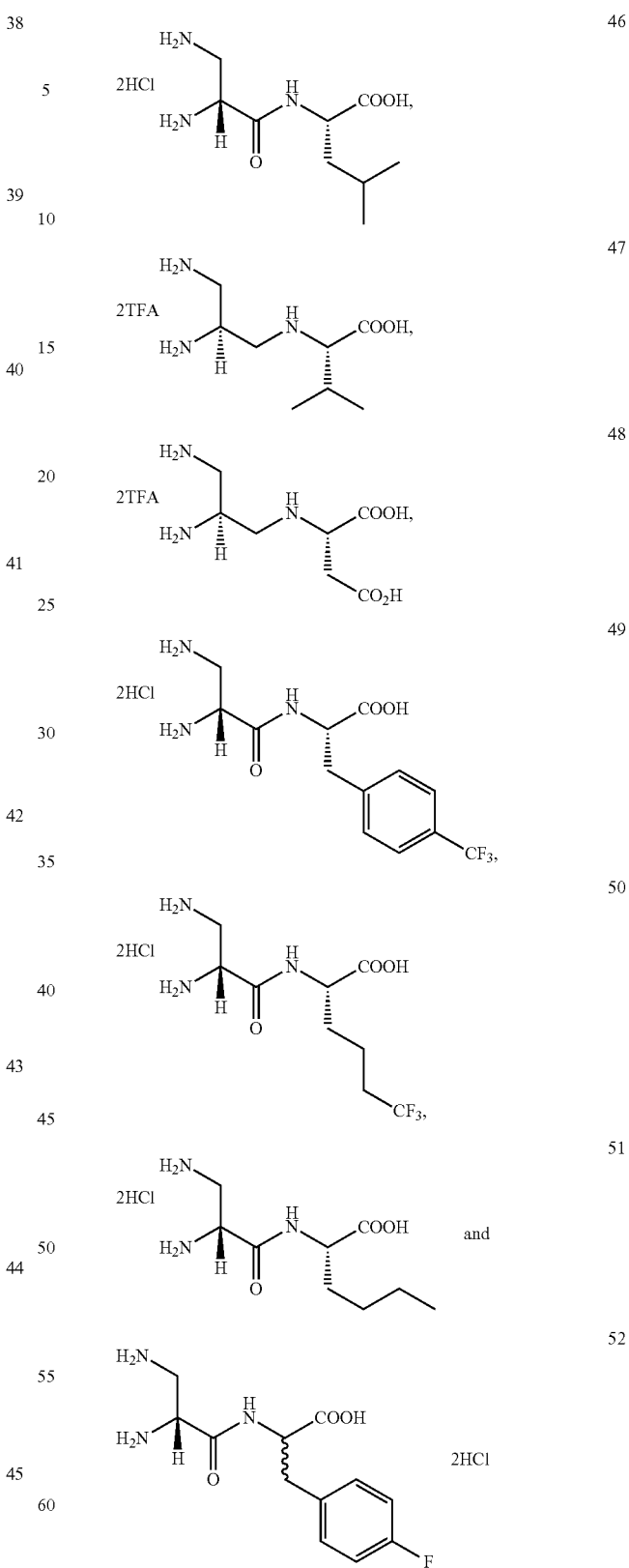
or the pharmaceutically acceptable addition salts, isomers, enantiomers and diastereoisomers of same, as well as mixtures of same.

The present invention also relates to the use of a compound according to the present invention to prevent the deterioration of proteins in foods.

Said foods can be of animal or plant origin. The compounds according to the present invention are administered in an effective quantity in said foods in order to prevent the deterioration and the degradation of proteins contained therein. Such a use increases the period during which the foods can be consumed and stored and preserves their nutritional and organoleptic qualities.

Additionally, the present invention relates to a pharmaceutical or cosmetic composition comprising a compound according to the present invention and a pharmaceutically or cosmetically acceptable excipient.

The present invention relates to a compound of following general formula I

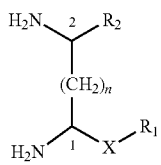

I wherein:

X represents $CH_2$, C=O, C=S or CHOH, $R_1$ represents an amino acid, optionally substituted by one or more halogen atoms, advantageously fluorine, or by one or more $CF_3$ groups, and n=0, 1 or 2 or X represents $CH_2$, C=O, C=S or CHOH, $R_1$ represents a peptide containing two amino acids, each amino acid being optionally substituted by one or more halogen atoms, advantageously fluorine, or one or more $CF_3$ groups, and n=0 or 1 or $XR_1$ represents $PO_3H$ or $SO_3H$ and n=0, 1 or 2;

$R_2$ represents H, $XR_2$, a $C_1$-$C_6$ alkyl group, a $C_1$-$C_6$ aralkyl group or an aryl group, the alkyl, aralkyl and aryl groups being able to be substituted by an amine ($NH_2$), a carboxylic group (COOH), one or more halogen atoms, advantageously fluorine, or one or more $CF_3$ groups;

or the pharmaceutically acceptable addition salts, isomers, enantiomers and diastereoisomers of same, as well as mixtures of same, with the exception of the compound

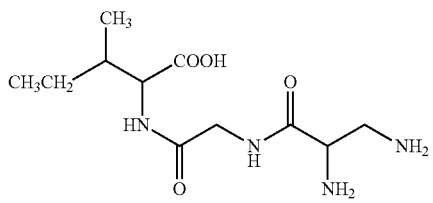

for use as a drug.

Advantageously, the compound according to the present invention for use as a drug is represented by the following general formula II:

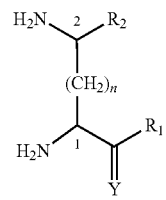

II wherein:

$R_1$ represents NH—$R_3$—(C=O)$R_4$ or

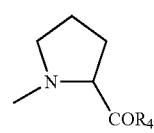

wherein $R_3$ represents a $C_1$-$C_{22}$ alkyl group, advantageously $C_1$-$C_6$, optionally substituted by one or more groups chosen among a halogen atom, advantageously fluorine, a —$CF_3$, phenyl, phenol, —COOH, amine or phenyl group substituted by one or more halogen atoms, advantageously fluorine, or by one or more $CF_3$ groups;

a phenyl group, optionally substituted by an amine, an OH group, one or more halogen atoms, advantageously fluorine, or one or more $CF_3$ groups and $R_4$ represents OH, $NH_2$, a $C_1$-$C_{30}$ alkoxy, advantageously $C_1$-$C_{20}$;

$R_2$ represents H, $COR_1$, or a $C_1$-$C_6$ alkyl group optionally substituted by one or more halogen atoms, advantageously fluorine, or by one or more $CF_3$ groups;

n=0, 1 or 2;

Y represents an oxygen or sulfur atom, advantageously an oxygen atom;

or the pharmaceutically acceptable addition salts, isomers, enantiomers and diastereoisomers of same, as well as mixtures of same.

Advantageously, the compound according to the present invention for use as a drug is selected among

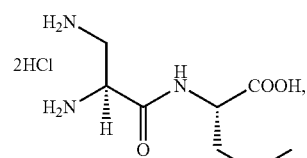

1

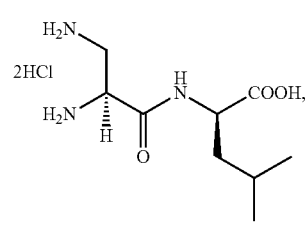

2

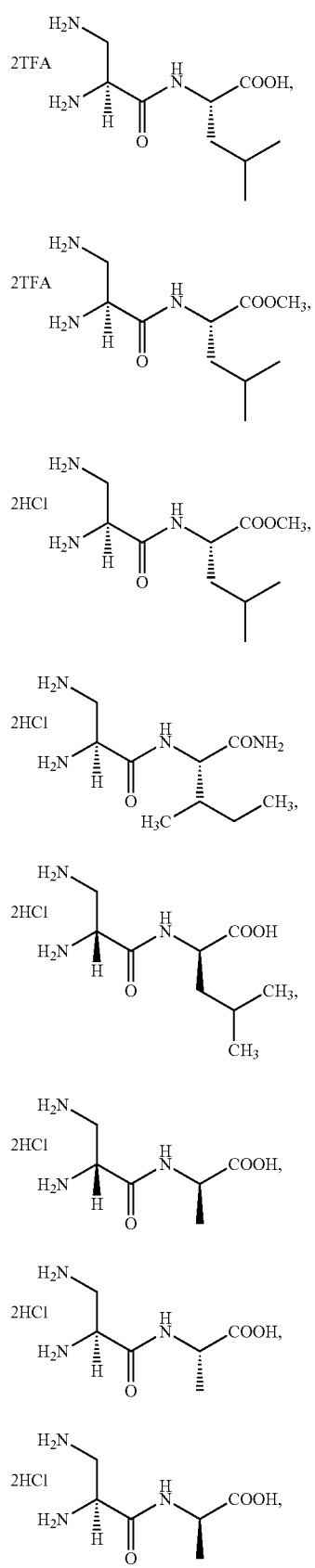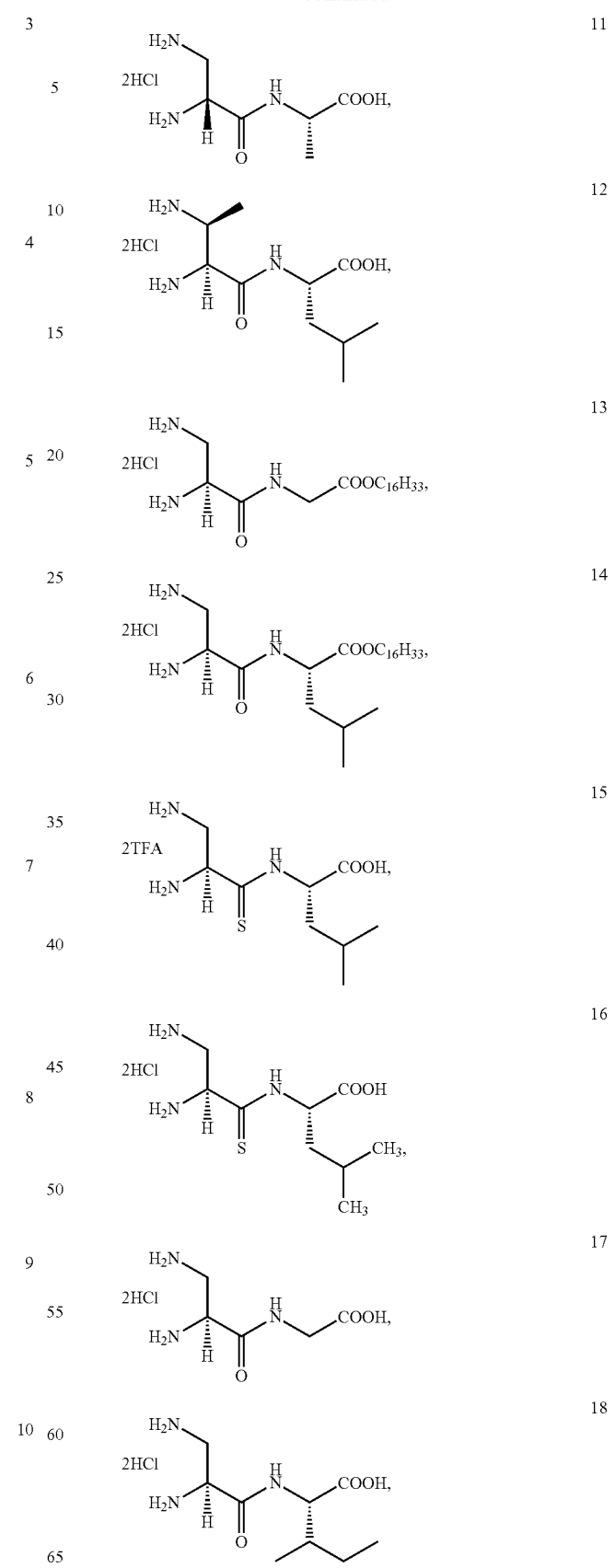

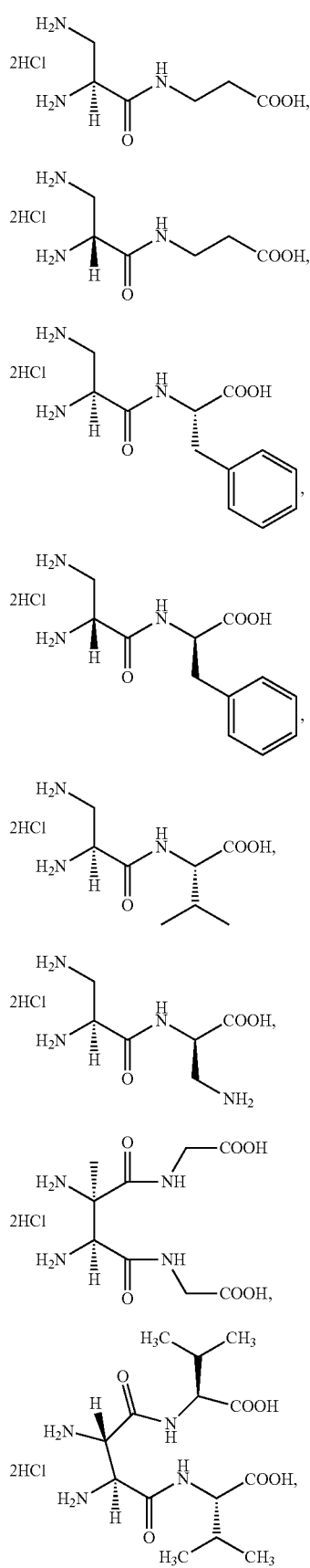
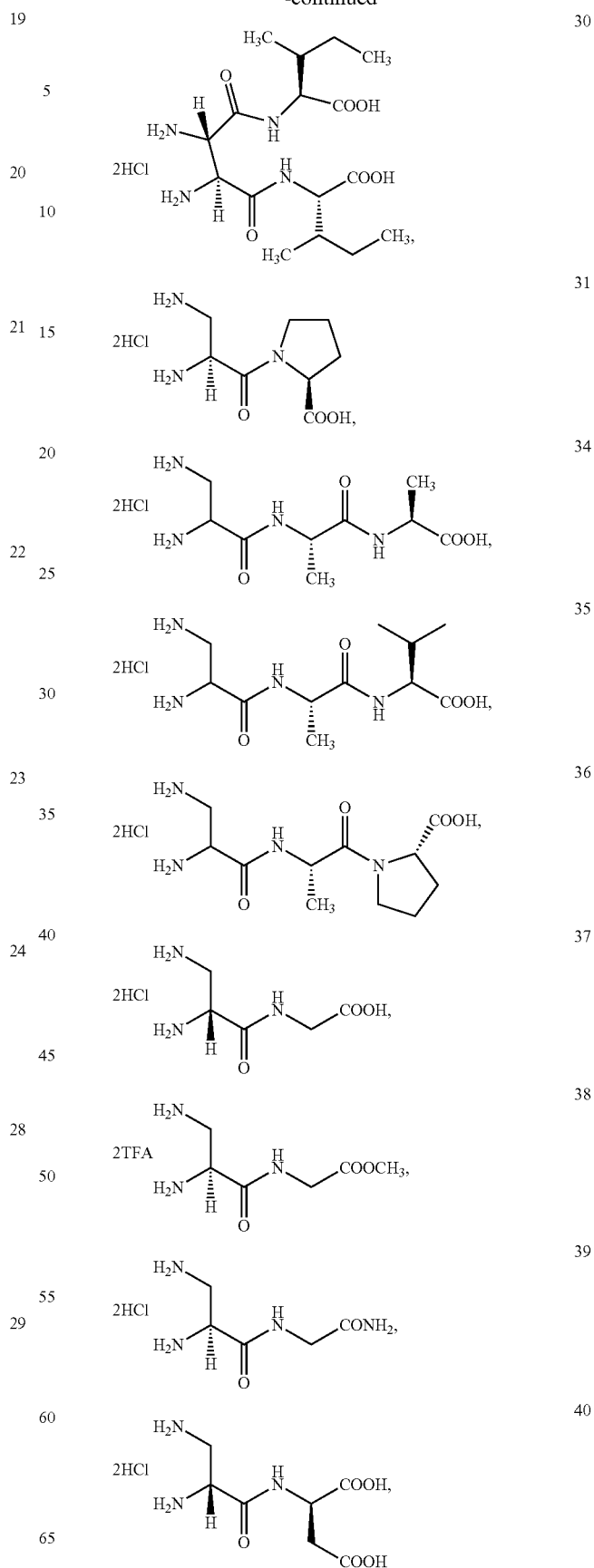

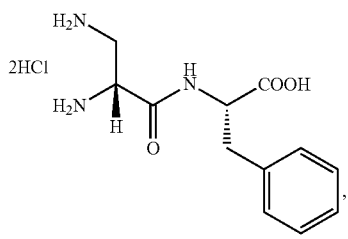

41

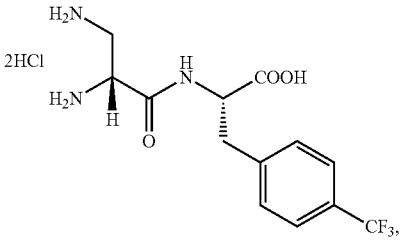

49

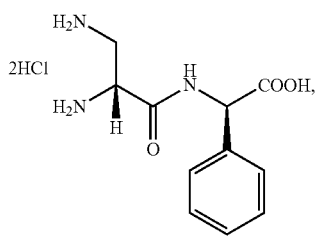

42

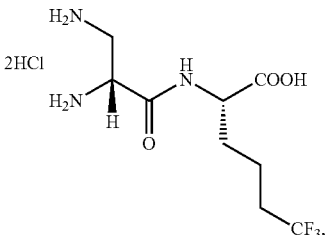

50

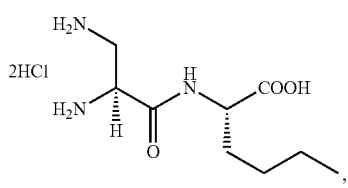

43

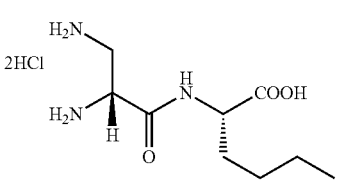

51 and

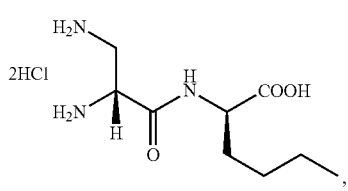

44

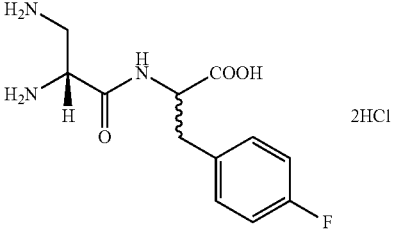

52

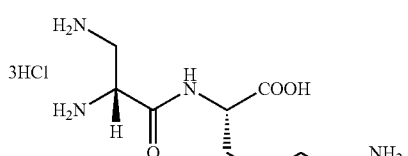

45

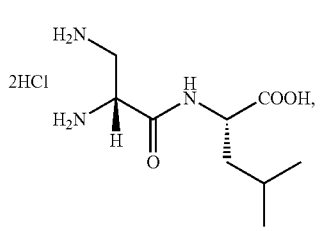

46

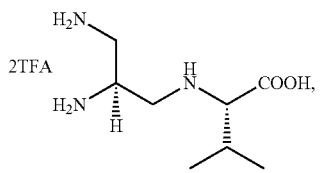

47

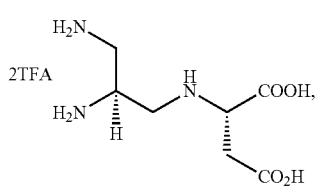

48 or the pharmaceutically acceptable addition salts, isomers, enantiomers and diastereoisomers of same, as well as mixtures of same.

In a specific embodiment, the drug according to the present invention is a scavenger of reactive carbonyl compounds, advantageously an inhibitor of the formation of advanced glycation end-products.

Advantageously, the drug according to the present invention is for the prevention and/or the treatment of a state or disease due to the formation of advanced glycation end-products or to the cross-linking of proteins, for the prevention and/or the treatment of the deleterious effects of the ageing of an organism, said effects being the formation of advanced glycation end-products or the cross-linking of proteins, or in a patient for the slowing or the stopping of the progression of complications resulting from diabetes, said complications resulting from the formation of advanced glycation end-products or from the cross-linking of proteins.

Advantageously, the drug according to the present invention is intended to treat, prevent and/or slow in a patient the progression of diseases chosen among rheumatoid polyarthritis, Alzheimer's disease, uremia, neurodegenerative diseases, atherosclerosis, microvascular and macrovascular complications of diabetes including diabetic retinopathy and renal failure due to diabetic nephropathy, microangiopathies and macroangiopathies, cataracts, amyloidosis associated with dialysis or with Alzheimer's disease, Parkinson's disease, gingivitis, cavities, bucco-dental conditions, diabetic ulcers, chronic renal failure, chronic renal dialysis, inflammatory diseases, age-related rheumatic disorders and porphyria and to treat early-stage cancers.

Even more advantageously, the drug according to the present invention is for administration by oral route.

Additionally, the present invention relates to the use of a compound of general formula I or II as defined above for the preparation of a drug that scavenges reactive carbonyl compounds, advantageously an inhibitor of the formation of advanced glycation end-products, advantageously for the prevention and/or the treatment of a state or disease due to the formation of advanced glycation end-products or to the cross-linking of proteins, the prevention and/or the treatment of the deleterious effects of the ageing of an organism, said effects being the formation of advanced glycation end-products or the cross-linking of proteins, or in a patient for the slowing or the stopping of the progression of complications resulting from diabetes, said complications resulting from the formation of advanced glycation end-products or from the cross-linking of proteins;

to treat, prevent and/or slow in a patient the progression of diseases chosen among rheumatoid polyarthritis, Alzheimer's disease, uremia, neurodegenerative diseases, atherosclerosis, microvascular and macrovascular complications of diabetes including diabetic retinopathy and renal failure due to diabetic nephropathy, microangiopathies and macroangiopathies, cataracts, amyloidosis associated with dialysis or with Alzheimer's disease, Parkinson's disease, gingivitis, cavities, bucco-dental conditions, diabetic ulcers, chronic renal failure, chronic renal dialysis, inflammatory diseases, age-related rheumatic disorders and porphyria and to treat early-stage cancers.

The present invention also relates to a method for the prevention and/or the treatment of a state or disease due to the formation of advanced glycation end-products or to the cross-linking of proteins, the prevention and/or the treatment of the deleterious effects of the ageing of an organism, said effects being the formation of advanced glycation end-products or the cross-linking of proteins, or in a patient for the slowing or the stopping of the progression of complications resulting from diabetes, said complications resulting from the formation of advanced glycation end-products or from the cross-linking of proteins; for the treatment, prevention and/or slowing in a patient of the progression of diseases chosen among rheumatoid polyarthritis, Alzheimer's disease, uremia, neurodegenerative diseases, atherosclerosis, microvascular and macrovascular complications of diabetes including diabetic retinopathy and renal failure due to diabetic nephropathy, microangiopathies and macroangiopathies, cataracts, amyloidosis associated with dialysis or with Alzheimer's disease, Parkinson's disease, gingivitis, cavities, bucco-dental conditions, diabetic ulcers, chronic renal failure, chronic renal dialysis, inflammatory diseases, age-related rheumatic disorders and porphyria and to treat early-stage cancers; said method comprising the administration in a patient in need of such a treatment of an effective quantity of a compound of general formula I or II according to the present invention as defined above.

Thus, the present invention relates to a drug or a pharmaceutical composition comprising a compound according to the present invention.

Said compositions or drugs can be formulated for administration in mammals, including human being. Dosing varies according to the treatment and to the affection to be treated. Said compositions or drugs are provided in such a way as to be suitable for administration by the digestive or parenteral route.

In the pharmaceutical compositions or drugs of the present invention for oral, sublingual, subcutaneous, intramuscular, intravenous, transdermal, local or rectal administration, the active ingredient can be administered in unit dose forms, in a mixture with conventional pharmaceutical carriers, to animals or to humans. Suitable unit dose forms include forms for oral administration such as tablets, gelatin capsules, powders, granules and oral solutions or suspensions, sublingual and buccal administration forms, subcutaneous, intramuscular, intravenous, intranasal, intraocular, or rectal administration forms.

When a solid composition or drug is prepared in tablet form, the principal active ingredient is mixed with a pharmaceutical carrier such as gelatin, starch, lactose, magnesium stearate, talc, gum arabic or analogues. The tablets can be coated with sucrose or other suitable materials or the tablets can be treated so that they have extended or delayed activity and that they continuously release a predetermined quantity of the active ingredient.

A preparation in gelatin capsules is obtained by mixing the active ingredient with a diluent and by pouring the mixture obtained into soft or hard gelatin capsules.

A preparation in syrup or elixir form can contain the active ingredient along with a sweetener and an antiseptic, as well as a flavoring agent and an agent that provides a suitable color.

Water-dispersible powders or granules can contain the active ingredient in a mixture with dispersion, wetting or suspension agents, as well as with flavor correctors or sweeteners.

Suppositories, which are prepared with binders that melt at rectal temperature, such as cocoa butter or polyethylene glycol, are used for rectal administration.

For parenteral, intranasal or intraocular administration, suitable preparations include aqueous suspensions, isotonic saline solutions or sterile injectable solutions containing pharmacologically compatible dispersion and/or wetting agents.

The active ingredient can be also formulated in microcapsule form, optionally with one or more carrier additives.

The active ingredient can also be administered by topical route.

The present invention also relates to the cosmetic use of a compound according to the present invention as an anti-ageing and restructuring active ingredient for the epidermis and the papillary dermis and/or as an anti-wrinkle active ingredient.

The compounds according to the present invention have a tensor effect on the skin. They can be administered by oral or topical route.

The cosmetic or pharmaceutical compositions according to the present invention can be formulated for administration by topical route. They can be provided in the forms commonly used for this type of administration, i.e., notably lotions, foams, gels, dispersions, sprays, shampoos, serums, masks, body milks or creams, for example, with excipients enabling in particular cutaneous penetration in order to improve the properties and the accessibility of the active ingredient. The forms can be a single-phase vehicle comprised of a neutral hydroxypropylcellulose gel or a gel containing sodium carboxymethylcellulose. It is also possible to prepare creams and two-phase vehicles containing a hydrophilic phase dispersed in a lipophilic phase.

In addition to the composition according to the present invention, such compositions or drugs generally contain a physiologically acceptable medium, in general containing water or solvents such as alcohols, ethers or glycols, for example. They can also contain a cosmetically or pharmaceutically acceptable excipient. Such excipients can be selected among compounds exhibiting suitable compatibility with the active ingredient. Examples of such excipients include natural water-soluble polymers such as polysaccharides (xanthan gum, carob bean gum, peptin, etc.) or polypeptides, cellulose derivatives such as methylcellulose, hydroxypropylcellulose and hydroxypropyl-methylcellulose, as well as synthetic polymers, poloxamers, carbomers, PVA or PVP.

Lastly, a person skilled in the art may choose to add to this cosmetic or pharmaceutical composition various co-solvent excipients such as ethanol, glycerol, benzyl alcohol, humectants (glycerol), diffusion agents (Transcutol, urea) or antibacterial preservatives (0.15% methyl p-hydroxybenzoate). Said composition can also contain surfactants, stabilizers, emulsifiers, thickeners, other active ingredients providing a complementary or possibly synergistic effect, trace elements, essential oils, fragrances, colorants, collagen, chemical or mineral filters, hydrating agents or thermal spring water.

The present invention also relates to a method for the cosmetic anti-ageing treatment of the skin by the application of a composition comprising a compound according to the present invention.

The abbreviations used within the framework of this application are as follows: DAPA=2,3-diaminopropionic acid, DABA=2,3-diaminobutylic acid (absent specification to the contrary) or 2,4-diaminobutylic acid, DASA=diaminosuccinic acid, EDC=1-[3-(dimethylamino)propyl]-3-ethylcarbodiimide hydrochloride, HOBt=1-hydroxybenzotriazole hydrate, Boc=t-butoxycarbonyl, TFA=trifluoroacetic acid, THF=tetrahydrofuran.

BRIEF DESCRIPTION OF THE FIGURES

The present invention will be better understood in reference to the figures wherein.

In these figures, (a) represents the results of somatostatin-14 alone; (b) represents the results of somatostatin-14+methylglyoxal; (c) represents the results of somatostatin-14+methylglyoxal+L-DAPA-L-Val (example 23) and (d) represents the results of somatostatin-14+methylglyoxal+L-DAPA-L-Leu (example 1). To obtain these results, somatostatin-14 (0.03 mm) is incubated in vitro in a 10 mM phosphate buffer, pH 7.45, containing 0.1 M NaCl, with or without (a) methylglyoxal (3.6 mM) in the presence ((c) and (d)) or the absence (b) of compounds according to the present invention (4.3 mM) for 24 hours at 37° C.

Figure 11:
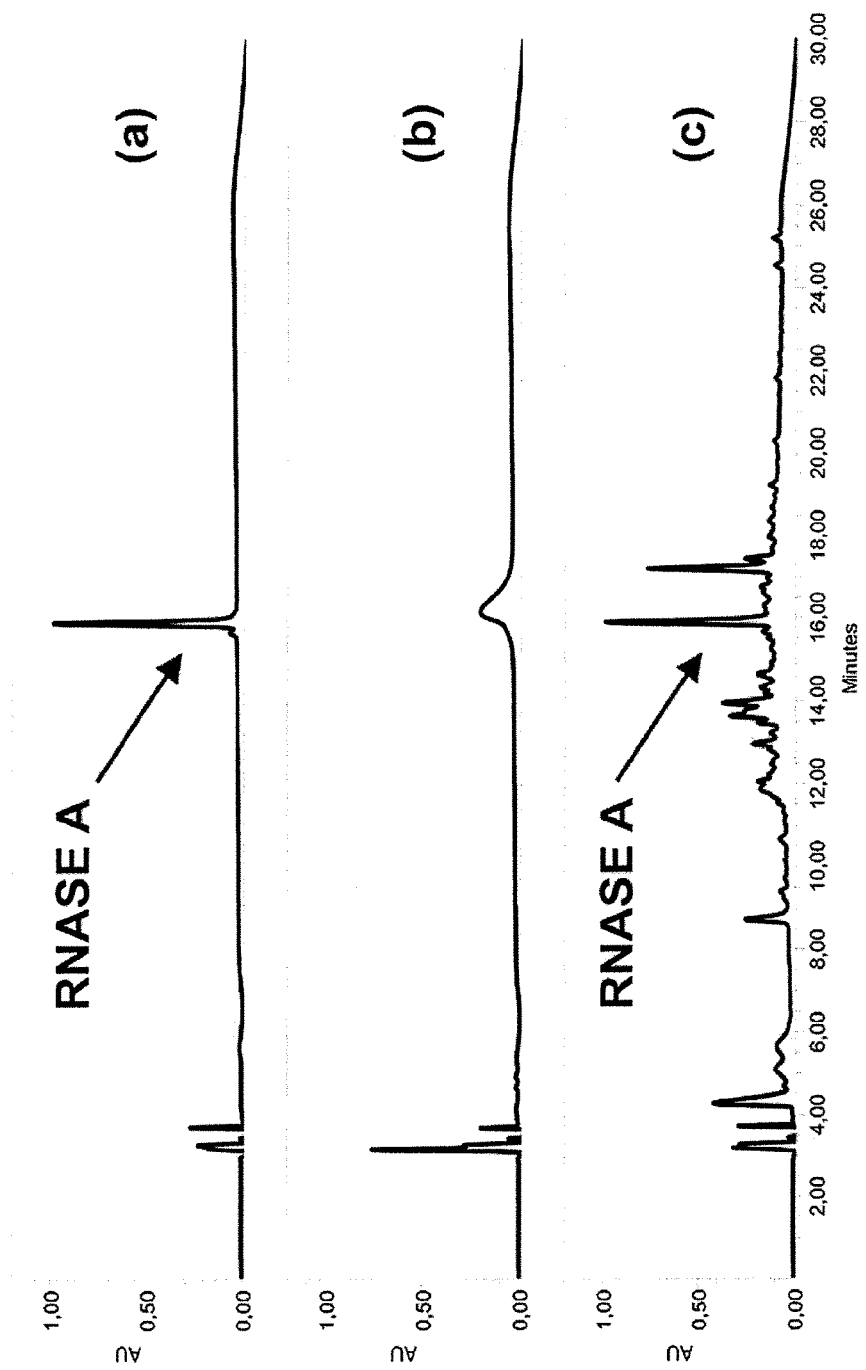
Figure 12:
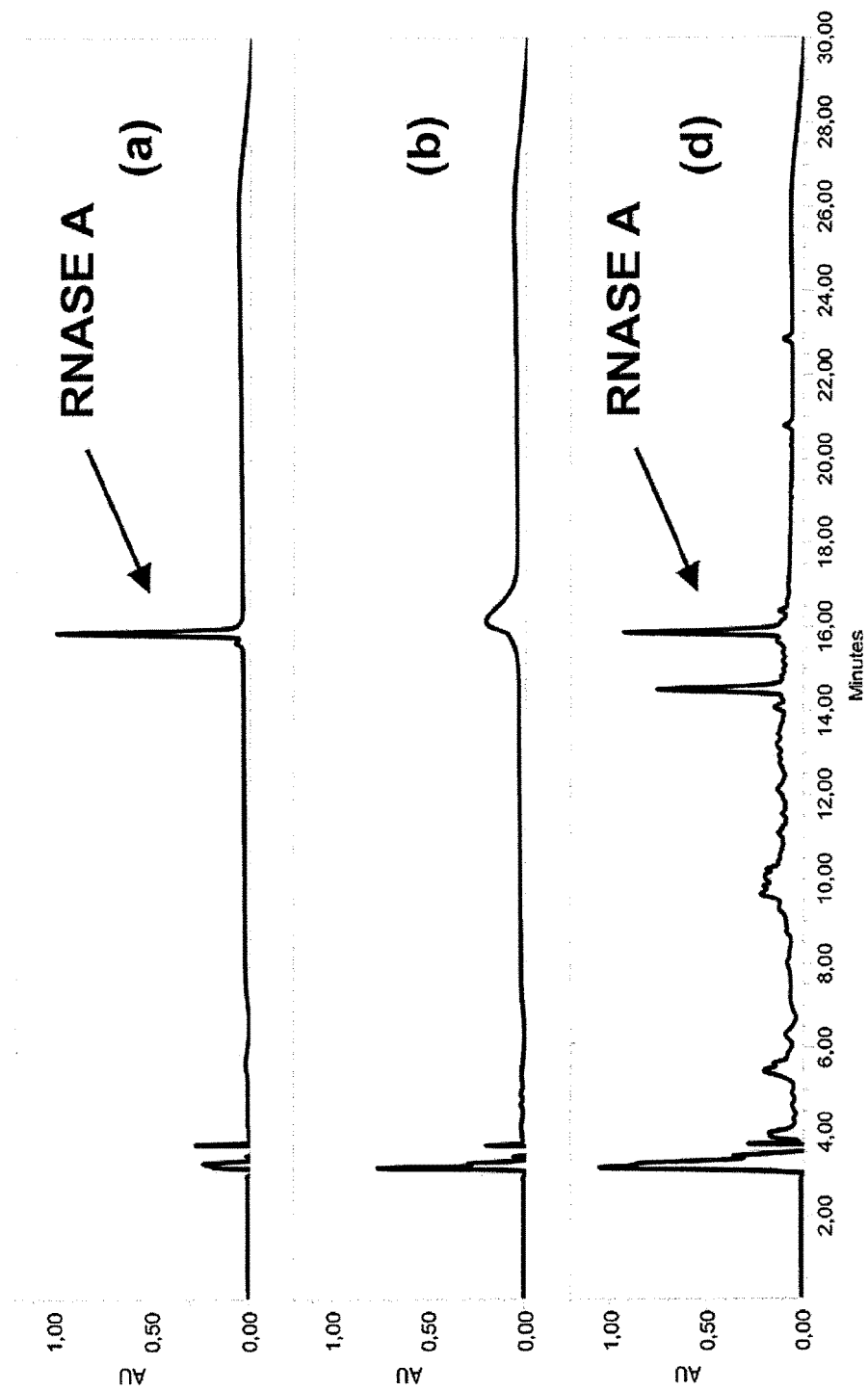
Figure 13:
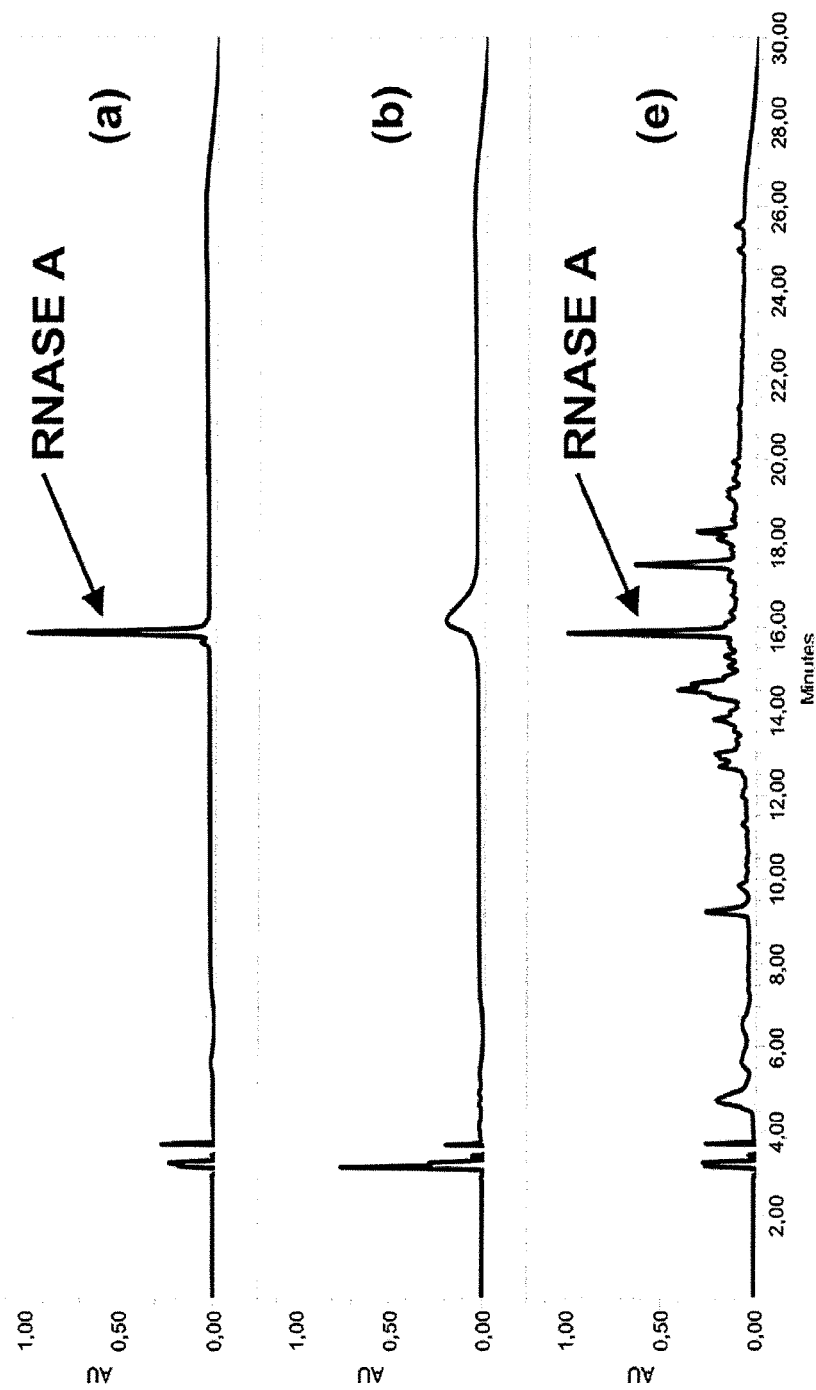

FIGS. 11 to 13 present the results obtained by HPLC for three compounds according to the present invention, L-DAPA-L-Ile (example 18), L-DAPA-L-Val (example 23) and L-DAPA-L-Leu (example 1), on RNase A modifications induced by methylglyoxal. HPLC conditions are as follows: C-18, Symmetry 300 (4.6×250 mm) column, injection volume 100 μl of reaction mixture diluted to ⅒; flow 1 ml/min; temperature 40° C.; solvent A: $H_2O$+0.1% TFA; solvent B: 60/40 $CH_3CN/H_2O$+0.1% TFA; linear gradient of 20% B to 80% B in 20 minutes; detection: UV at 215 nm: PDA (chromatograms extracted at 215 nm). The compounds according to the present invention prevent the modifications to RNase A. In these figures: (a) represents the results of RNase A; (b) represents the results of RNase A+methylglyoxal; (c) represents the results of RNase A+methylglyoxal+L-DAPA-L-Ile (example 18); (d) represents the results of RNase A+methylglyoxal+L-DAPA-L-Val (example 23); (e) represents the results of RNase A+methylglyoxal+L-DAPA-L-Leu (example 1). To obtain these results, RNase A (0.08 mM) is incubated in vitro in a 100 mM phosphate buffer, pH 7.45, with or without (a) methylglyoxal (32 mM) in the presence ((c), (d) and (e)) or the absence (b) of compounds according to the present invention (38 mM) for 21 hours at 37° C.

Figure 14:
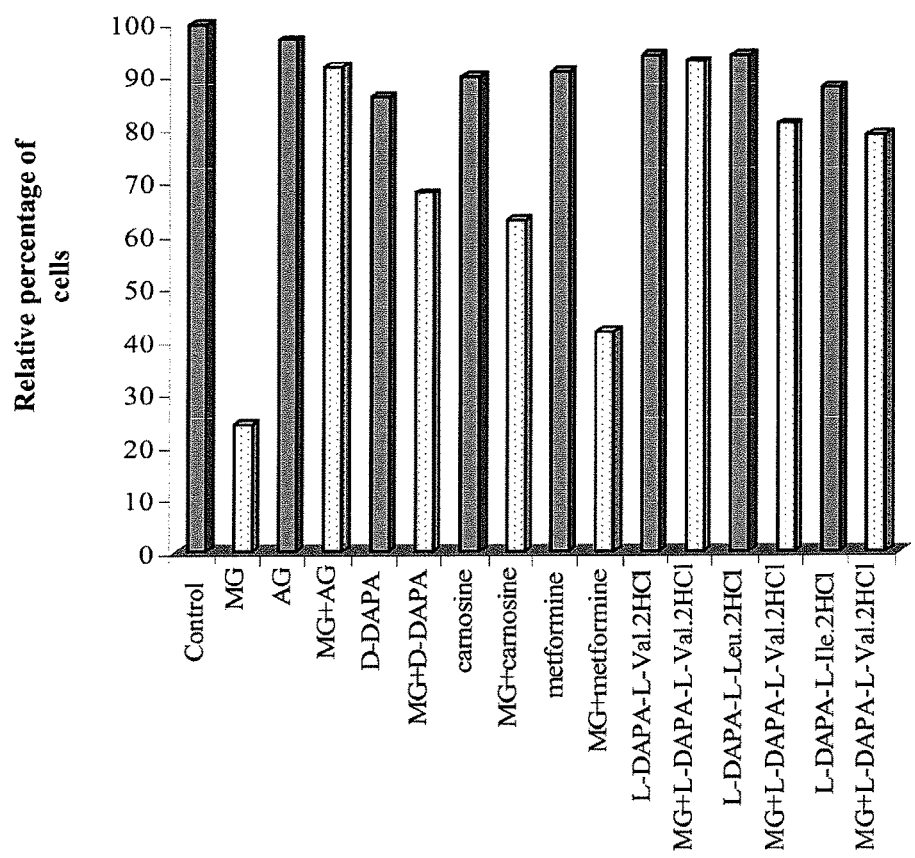
Figure 15:
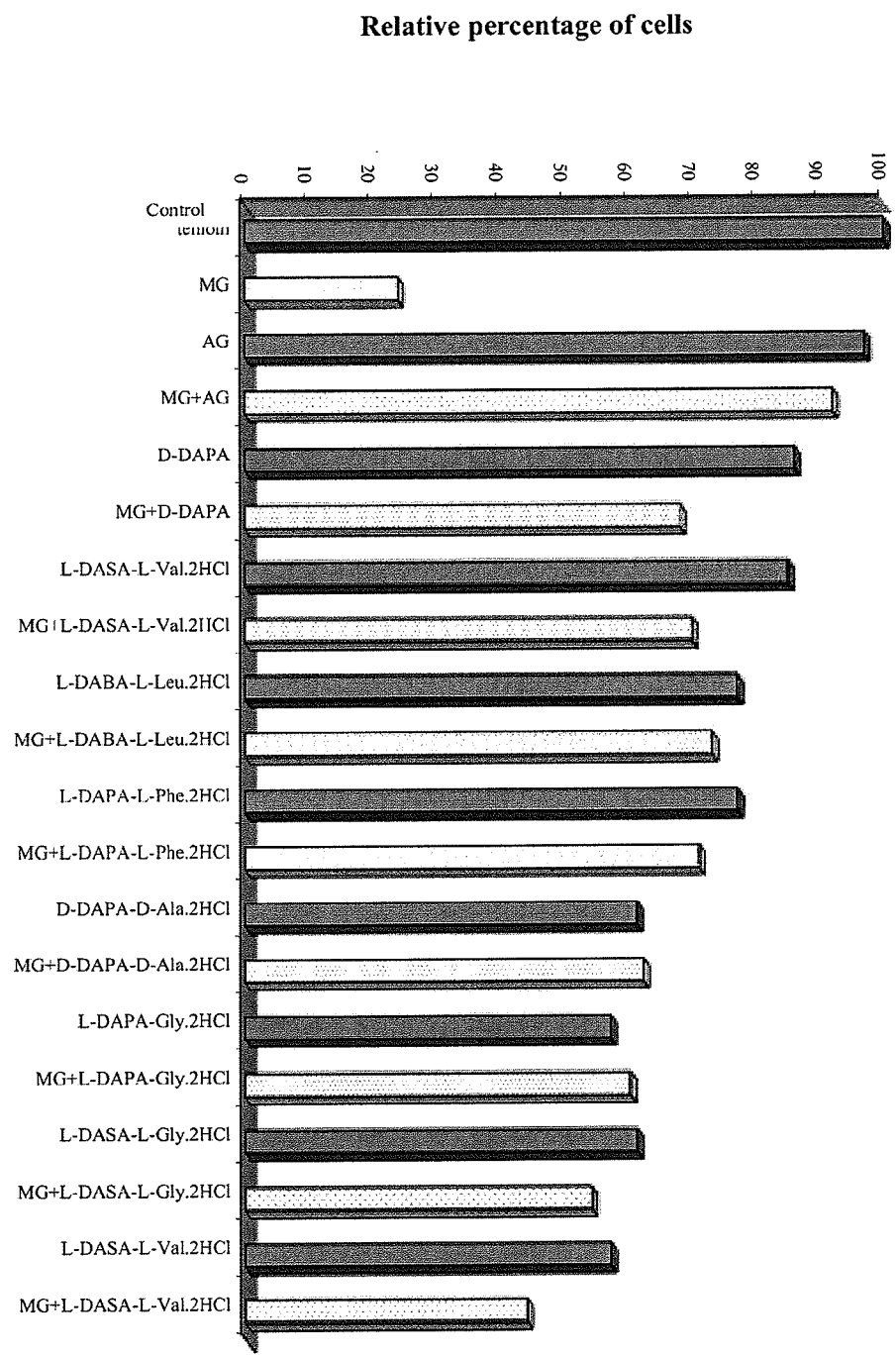

FIGS. 14 and 15 represents EA endothelial cell growth in the presence of compounds according to the present invention and compounds according to the prior art, in particular aminoguanidine (AG) and diaminopropionic acid (DAPA), in the presence or absence of methylglyoxal (MG).

DETAILED DESCRIPTION

The general method for producing compounds according to the present invention comprises step (a), or steps (a) and (b), or steps (a), (b) and (c), or steps (a) and (d), or steps (a), (d) and (e), as follows:

a) coupling of an amino acid or peptide alkyl ester with an N-protected diamino acid (for example, DAPA, DABA, DASA, Orn or Lys according to the value of n) in an organic solvent, advantageously dichloromethane, advantageously by using reagents forming an active ester, such as EDC and HOBt, for example, advantageously under agitation at room temperature;

b) alkaline hydrolysis of the alkyl ester obtained in step (a), advantageously with LiOH, advantageously in the solvent THF/MeOH/H$_2$O, MeOH/H$_2$O or H$_2$O, then acidification, advantageously with an aqueous solution of KHSO$_4$ at pH 5 to obtain the pure acid;

c) deprotection of the N-protecting groups of the acid obtained in step (b) advantageously with 3 M HCl-dioxane (or THF) and elimination of the volatile components;

d) preparation of thioamides by addition of Lawesson's reagent to the peptide obtained in step (a), advantageously under inert atmosphere, and heating, advantageously at 80° C., for two hours;

e) deprotection of the thioamides with di-Boc, tert-butyl ester protection obtained in step (d) by the addition of TFA in an organic solvent, advantageously dichloromethane, at a low temperature, advantageously 0° C.

In an advantageous embodiment, the compounds according to the present invention can be produced according to the method described hereafter, i.e., the implementation of step (1), or of steps (1) and (2), or of steps (1), (2) and (3), or of steps (1) and (4), or of steps (1), (4) and (5).

1. Coupling Reaction of N-Protected Carboxylic Acids and Amino Acid Alkyl Esters To a solution of a diamino acid (for example, DAPA, DABA, DASA, Orn or Lys) (1.0 mmol) properly N-protected (preferably by a Boc group) and an amino acid alkyl ester (1.1 mmol) in dichloromethane (5.0 ml) were added reagents forming an active ester (for example, EDC (1.2 mmol) and HOBt (1.1 mmol)) and the reaction mixture was stirred at room temperature overnight. Water was added and the aqueous phase was extracted with EtOAc. The combined organic layers were washed successively with 1 N HCl, H$_2$O, saturated NaHCO$_3$ and brine, dried on Na$_2$SO$_4$ and then filtered. The solvent was evaporated under reduced pressure and then the residue was purified by flash column chromatography to obtain the dipeptide.

2. Alkaline Hydrolysis of the Alkyl Ester

To a solution of alkyl ester (1.0 mmol) in THF/MeOH/H$_2$O or MeOH/H$_2$O at room temperature was added an alkaline solution (preferably 1.0 mmol LiOH). The reaction mixture was then agitated until all of the starting ester had disappeared (approximately overnight). The reaction mixture was acidified with an aqueous solution of KHSO$_4$ at pH 5 and then extracted with an organic solvent (preferably CH$_2$Cl$_2$). The organic phase was dried (Na$_2$SO$_4$) and then evaporated under reduced pressure to obtain the crude acid, which is used directly in the following reaction without additional purification.

3. Deprotection of the N-Protecting Groups

A solution of N-protected dipeptide carboxylic acid (1 mmol) in 3 M HCl-dioxane (or THF) was agitated at room temperature for three to nine hours. The volatile components were eliminated by evaporation to obtain the dipeptide hydrochloride.

4. Preparation of the Thioamides

Lawesson's reagent (1.1 mmol) was added all at once to a solution of the dipeptide mentioned above (step 1) (2.0 mmol) in toluene (10 ml) at room temperature under an argon atmosphere. The reaction mixture was agitated for two hours at 80° C. The solvent was eliminated by evaporation under reduced pressure. The residue was purified by silica-gel column chromatography (CH$_2$Cl$_2$ then 10/1 CH$_2$Cl$_2$/Et$_2$O) to obtain the corresponding thioamide.

5. Deprotection of the Thioamides with Di-Boc, Tert-Butyl Ester Protection

TFA (5 ml) was added to a solution of thioamide tert-butyl ester with di-Boc protection (1 mmol) in dichloromethane (5 ml) at 0° C.; the resulting solution was stored overnight at 0° C. The volatile components were eliminated by evaporation to obtain the dithiopeptide in the form of trifluoroacetic acid salt.

The following examples are given as non-limiting illustrations.

The following compounds according to the present invention were prepared by implementing the method described above.

Example 1

L-DAPA-L-Leu.2HCl

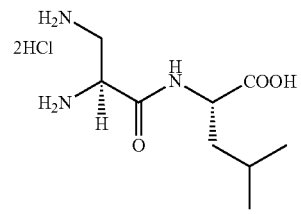

1

$^1$H NMR (300 MHz, CD$_3$OD) δ 4.37 (t, J=5.8 Hz, 1H), 4.30 (dd, J=9.4, 5.6 Hz, 1H), 3.45 (dd, J=13.9, 6.0 Hz, 1H), 3.34 (dd, J=13.9, 5.3 Hz, 1H), 1.64-1.49 (m, 3H), 0.78 (d, J=6.4 Hz, 3H), 0.74 (d, J=6.4 Hz, 3H);

$^{13}$C NMR (75 MHz, CD$_3$OD) δ 176.6, 167.3, 53.0, 51.7, 41.4, 40.6, 26.1, 23.4, 21.5;

MS (ESI) m/z 218 [M+H]$^+$;

HRMS calculated for C$_9$H$_{20}$N$_3$O$_3$ (M+H) 218.1505. found: 218.1512.

$[\alpha]_D^{26}$ +3.41 (c 1.0, 6 N HCl)

Example 2

L-DAPA-D-Leu.2HCl

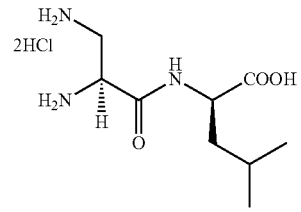

2

$[\alpha]_D^{22}$ +7.8 (c 1.0 H$_2$O)
$[\alpha]_D^{26}$ +39.59 (c 1.0, 6 N HCl)
$^1$H NMR (300 MHz, CD$_3$OD) δ 4.38 (dd, J=5.0, 6.7 Hz, 1H), 4.30 (t, J=7.8 Hz, 1H), 3.60-3.43 (m, 2H), 1.67-1.56 (m, 3H), 0.86 (d, J=6.0 Hz, 3H), 0.83 (d, J=6.0 Hz, 3H);

$^{13}$C NMR (75 MHz, D$_2$O) δ 175.9, 166.0, 52.3, 50.7, 39.6, 39.1, 24.5, 22.0, 20.9;

MS (ESI) m/z 218 [M+H]$^+$;

HRMS calculated for C$_9$H$_{20}$N$_3$O$_3$ (M+H) 218.1505. found: 218.1552.

Example 3

L-DAPA-L-Leu.2TFA

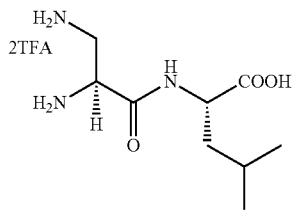

$[\alpha]_D^{22}$ +20 (c 0.5, MeOH;
$[\alpha]_D^{24}$ +1.13 (c 1.0, 6 N HCl)
$^1$H NMR (300 MHz, CD$_3$OD) δ 4.51-4.46 (m, 1H), 4.12 (t, J=6.2 Hz, 1H), 3.36 (d, J=5.9 Hz, 2H), 1.78-1.62 (m, 3H), 0.98 (d, J=6.1 Hz, 3H), 0.95 (d, J=6.1 Hz, 3H);
$^{13}$C NMR (62.5 MHz, D$_2$O) δ 176.6, 166.8, 52.6, 51.1, 40.3, 39.7, 25.1, 22.7, 21.1;
MS (ESI) m/z 218 [M+H]$^+$, 240 [M+Na]$^+$;
HRMS calculated for C$_9$H$_{20}$N$_3$O$_3$ (M+H) 218.1505. found: 218.1512, calculated for C$_9$H$_{19}$N$_3$O$_3$Na (M+Na) 240.1324. found: 240.1364.

Example 4

L-DAPA-L-LeuOMe.2TFA

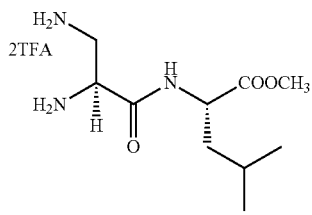

$[\alpha]_D$ +3.8 (c 1.2, MeOH);
$^1$H NMR (300 MHz, CD$_3$OD) δ 4.55 (t, J=7.4 Hz, 1H), 4.42 (t, J=5.9 Hz, 1H), 3.75 (s, 3H), 3.52 (d, J=5.9 Hz, 2H), 1.81-1.61 (m, 3H), 0.95 (d, J=6.8 Hz, 3H), 0.93 (d, J=6.6 Hz, 3H);
$^{13}$C NMR (62.5 MHz, CD$_3$OD) δ 175.0, 167.4, 53.4, 52.8, 51.9, 41.3, 40.9, 25.9, 23.3, 21.6;
MS (ESI) m/z 232 (M+H)$^+$, 254 [M+Na]$^+$;
HRMS calculated for C$_{10}$H$_{22}$N$_3$O$_3$ (M+H) 232-1661. found: 232.1660.

Example 5

L-DAPA-L-LeuOMe.2HCl

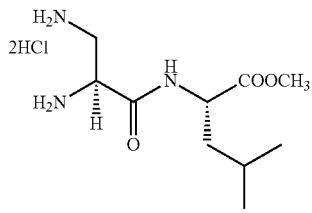

$^1$H NMR (300 MHz, CD$_3$OD) δ 4.46 (dd, J=7.7, 5.6 Hz, 1H), 4.44 (t, J=4.9 Hz, 1H), 3.67 (s, 3H), 3.48 (d, J=5.6 Hz, 2H), 1.75-1.55 (m, 3H), 0.89 (d, J=6.4 Hz, 3H), 0.86 (d, J=6.4 Hz, 3H);
$^{13}$C NMR (75 MHz, CD$_3$OD) δ 175.0, 167.1, 53.4, 52.9, 51.8, 41.4, 40.8, 26.0, 23.3, 21.6;
MS (ESI) m/z 232 [M+H]$^+$;
HRMS calculated for C$_{10}$H$_{22}$N$_3$O$_3$ (M+H) 232.1661. found: 232.1660.
$[\alpha]_D^{24}$ +6.2 (c 0.7, MeOH)

Example 6

L-DAPA-L-IleNH$_2$.2HCl

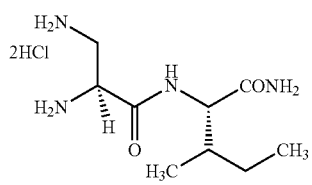

$[\alpha]_D$ +25 (c 0.5, MeOH);
$^1$H NMR (300 MHz, CD$_3$OD) δ 4.59 (dd, J=7.0, 5.5 Hz, 1H), 4.37 (d, J=5.5 Hz, 1H), 3.57 (dd, J=13.4, 5.5 Hz, 1H), 3.36 (dd, J=13.4, 7.2 Hz, 1H), 2.01-1.91 (m, 1H), 1.58-1.47 (m, 1H), 1.44-1.28 (m, 1H), 1.05 (d, J=6.8 Hz, 3H), 0.95 (t, J=7.4 Hz, 3H);
$^{13}$C NMR (62.5 MHz, CD$_3$OD) δ 176.3, 167.6, 60.6, 51.3, 41.2, 37.8, 25.5, 16.3, 12.0;
MS (ESI) m/z 217 [M+H]$^+$, 239 [M+Na]$^+$;
HRMS calculated for C$_9$H$_{21}$N$_4$O$_2$ (M+H) 217.1665. found: 217.1674, calculated for C$_9$H$_{20}$N$_4$O$_2$Na (M+Na) 239.1484. found: 239.1499.

Example 7

D-DAPA-D-Leu.2HCl

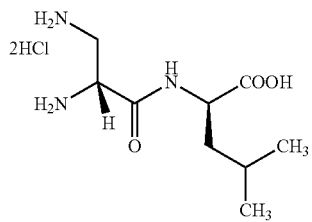

$^1$H NMR (300 MHz, D$_2$O) δ 4.38-4.31 (m, 2H), 3.50-3.34 (m, 2H), 1.62-1.50 (m, 3H), 0.79 (d, J=6.4 Hz, 3H), 0.75 (d, J=6.4 Hz, 3H).
$[\alpha]_D$ −11.7 (c 1.0, H$_2$O)
MS (ESI) m/z 218 [M+H]$^+$; 240 [M+Na]$^+$;
HRMS calculated for C$_9$H$_{20}$N$_3$O$_3$ (M+H): 218.1505. found: 218.1537.

Example 8

D-DAPA-D-Ala.2HCl

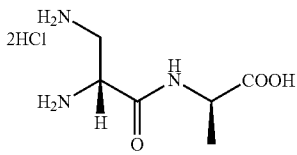

8

[α]<sub>D</sub> −21.9 (c 1.0, MeOH);
$[\alpha]_D^{26}$ −6.15 (c 1.0, 6 N HCl)
$^1$H NMR (300 MHz, D$_2$O) δ 4.53 (q, J=7.4 Hz, 1H), 4.48 (t, J=6.0 Hz, 1H), 3.64 (d, J=6.0 Hz, 2H), 1.50 (d, J=7.4 Hz, 3H);
$^{13}$C NMR (75 MHz, D$_2$O) δ 176.7, 166.5, 51.2, 49.9, 40.3, 16.6;
MS (ESI) m/z 176 [M+H]$^+$;
Analysis, calculated for C$_6$H$_{15}$N$_3$O$_3$Cl$_2$: C, 29.05; H, 6.09; N, 16.94; Cl, 28.58. found: C, 28.67; H, 6.24; N, 16.67; Cl, 27.64.

Example 9

L-DAPA-L-Ala.2HCl

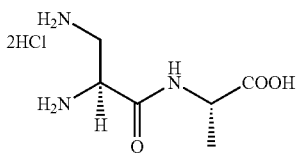

9

$^1$H NMR (300 MHz, D$_2$O) δ 4.51 (q, J=7.5 Hz, 1H), 4.46 (t, J=6.0 Hz, 1H), 3.62 (d, J=6.0 Hz, 2H), 1.49 (d, J=7.5 Hz, 3H);
$^{13}$C NMR (75 MHz, D$_2$O) δ 176.8, 166.5, 51.2, 49.9, 40.3, 16.6;
MS (ESI) m/z 176 [M+H]$^+$;
HRMS calculated for C$_6$H$_{14}$N$_3$O$_3$, (M+H) 176.1035. found: 176.1037.
$[\alpha]_D^{26}$ +7.83 (c 1.0, 6 N HCl)

Example 10

L-DAPA-D-Ala.2HCl

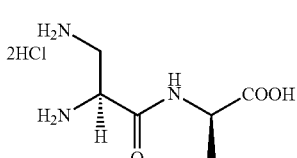

10

$^1$H NMR (300 MHz, D$_2$O) δ 4.33-4.24 (m, 2H), 3.50-3.39 (m, 2H), 1.41 (d, J=7.4 Hz, 3H);
$^{13}$C NMR (75 MHz, D$_2$O) δ 176.0, 166.0, 50.9, 49.5, 39.8, 16.3;
MS (ESI) m/z 176 [M+H]$^+$;
HRMS calculated for C$_6$H$_{14}$N$_3$O$_3$ (M+H) 176.1035. found: 176.1044.
$[\alpha]_D^{26}$ +64.56 (c 1.0, 6 N HCl)

Example 11

D-DAPA-L-Ala.2HCl

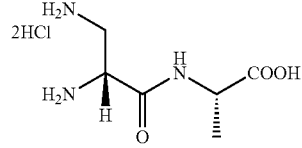

11

$^1$H NMR (300 MHz, D$_2$O) δ 4.49-4.41 (m, 2H), 3.68-3.54 (m, 2H), 1.49 (d, J=7.3 Hz, 3H);
$^{13}$C NMR (75 MHz, D$_2$O) δ 176.4, 166.3, 51.3, 49.8, 40.1, 16.6;
MS (ESI) m/z 176 [M+H]$^+$;
HRMS calculated for C$_6$H$_{14}$N$_3$O$_3$ (M+H) 176.1035. found: 176.1043.
$[\alpha]_D^{26}$ −60.9 (c 1.0, 6 N HCl)

Example 12

(2S,3S)-DABA-L-Leu.2HCl

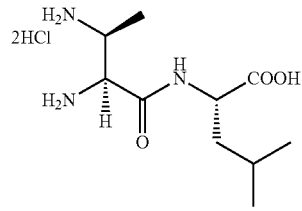

12

$^1$H NMR (300 MHz, D$_2$O) δ 4.34 (t, J=7.2 Hz, 1H), 4.22 (d, J=4.2 Hz, 1H), 3.87 (dq, J=4.2, 7.2 Hz, 1H), 1.58-1.56 (m, 3H), 1.34 (d, J=6.8 Hz, 3H), 0.79 (d, J=6.0 Hz, 3H), 0.76 (d, J=6.0 Hz, 3H);
$^{13}$C NMR (75 MHz, D$_2$O) δ 175.9, 165.6, 54.4, 52.0, 47.9, 39.0, 24.3, 22.0, 20.5, 14.0;
MS (ESI) m/z 232 [M+H]$^+$;
HRMS calculated for C$_{10}$H$_{22}$N$_3$O$_3$ (M+H) 232.1661. found: 232.1663.
$[\alpha]_D^{22}$ +9.6 (c 0.2, H$_2$O)

Example 13

L-DAPA-Gly-OC$_{16}$H$_{33}$.2HCl

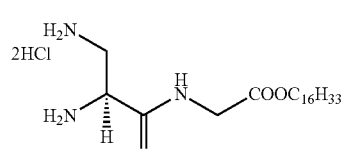

13

¹H NMR (300 MHz, CD₃OD) δ 4.44 (t, J=5.8 Hz, 1H), 4.20 (t, J=6.7 Hz, 2H), 4.17, 4.07 (AB q, J=17.8 Hz, 2H), 3.53 (d, J=5.8 Hz, 2H), 1.73-1.64 (m, 2H), 1.43-1.30 (m, 26H), 0.91 (t, J=6.7 Hz, 3H);

¹³C NMR (75 MHz, CD₃OD) δ 171.6, 167.5, 67.0, 51.9, 42.3, 41.2, 33.1, 30.8, 30.7, 30.5, 30.4, 29.7;

MS (ESI) m/z 386 [M+H]⁺;

HRMS calculated for $C_{21}H_{44}N_3O_3$ (M+H) 386.3383. found: 386.3352.

$[\alpha]_D^{26}$ −5.98 (c 0.5, MeOH)

Example 14

L-DAPA-L-Leu-OC₁₆H₃₃.2HCl

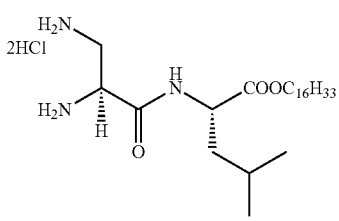

14

¹H NMR (300 MHz, CD₃OD) δ 4.34-4.28 (m, 2H), 4.01-3.86 (m, 2H), 3.41-3.29 (m, 2H), 1.61-1.39 (m, 5H), 1.16-1.05 (m, 26H), 0.76 (d, J=6.4 Hz, 3H), 0.72 (d, J=6.4 Hz, 3H), 0.66 (t, J=6.7 Hz, 3H);

¹³C NMR (75 MHz, CD₃OD) δ 174.6, 167.2, 67.2, 53.0, 51.8, 41.4, 40.9, 33.2, 30.9, 30.6, 30.6, 30.4, 29.7, 27.0, 26.1, 23.8, 23.4, 21.8, 14.6;

MS (ESI) m/z 442 [M+H]⁺;

HRMS calculated for $C_{25}H_{52}N_3O_3$ (M+H) 442.4009. found: 441.3983.

$[\alpha]_D^{26}$ +13.1 (c 2.0, MeOH)

Example 15

L-DAPA-L-(S)-Leu.2TFA

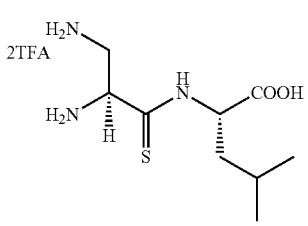

15

¹H NMR (300 MHz, D₂O) δ 4.79 (dd, J=9.3, 5.4 Hz, 1H), 4.56 (t, J=6.4 Hz, 1H), 3.48 (dd, J=13.8, 5.8 Hz, 1H), 3.41 (dd, J=13.8, 6.6 Hz, 1H), 1.79-1.53 (m, 3H), 0.81 (d, J=6.4 Hz, 3H), 0.77 (d, J=6.4 Hz, 3H);

¹³C NMR (62.5 MHz, D₂O) δ 194.5, 174.9, 58.0, 54.6, 41.5, 38.8, 24.7, 22.0, 20.7;

MS (ESI) m/z 234 [M+H]⁺;

HRMS calculated for $C_9H_{20}N_3O_2S$: 234.1276. found: 234.1306.

$[\alpha]_D^{26}$ +60.6 (c 2.5, MeOH)

Example 16

L-DAPA-L-(S)-Leu.2HCl

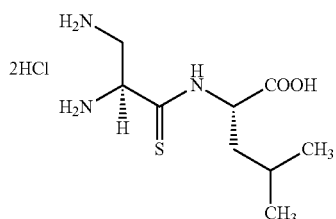

16

¹H NMR (300 MHz, D₂O) δ 4.80 (dd, J=9.6, 4.9 Hz, 1H), 4.60 (t, J=6.2 Hz, 1H), 3.52-3.39 (m, 2H), 1.81-1.58 (m, 3H), 0.82 (d, J=6.4 Hz, 3H), 0.78 (d, J=6.2 Hz, 3H);

¹³C NMR (62.5 MHz, D₂O) δ 194.5, 174.8, 57.9, 54.6, 41.5, 38.8, 24.7, 22.0, 20.7;

MS (ESI) m/z 234 [M+H]⁺;

HRMS calculated for $C_9H_{20}N_3O_2S$: 234.1276. found: 234.1306.

$[\alpha]_D^{26}$ +90.6 (c 1.0, MeOH)

Example 17

L-DAPA-Gly.2HCl

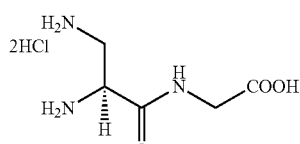

17

¹H NMR (300 MHz, D₂O) δ 4.54 (t, J=5.8 Hz, 1H), 4.20 (d, J=18.0 Hz, 1H), 4.10 (d, J=18.0 Hz, 1H), 3.65 (d, J=5.8 Hz, 1H);

¹³C NMR (75 MHz, D₂O) δ 173.1, 166.5, 50.5, 41.6, 39.5;

MS (ESI) m/z 162 [M+H]⁺

HRMS calculated for $C_5H_{12}N_3O_3$ (M+H) 162.0879. found: 162.0864.

$[\alpha]_D^{25}$ +28 (c 1.8, H₂O)

Example 18

L-DAPA-L-Ile.2HCl

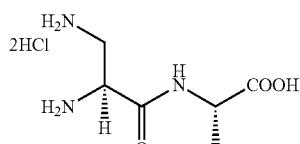

18

¹H NMR (300 MHz, D₂O) δ 4.52 (t, J=5.9 Hz, 1H); 4.46 (d, J=4.9 Hz, 1H); 3.60 (d, J=5.9 Hz, 2H); 2.05 (m, 1H); 1.45 (m, 1H); 1.27 (m, 1H); 0.97 (d, J=6.9 Hz, 3H); 0.90 (t, J=7.3 Hz, 3H);

$^{13}$C NMR (62.5 MHz, D$_2$O) δ 175.5, 166.8, 58.8, 51.1, 40.3, 37.0, 25.3, 15.7, 11.6;

MS (ESI) m/z 218 [M+H], 240 [M+Na]$^+$;

HRMS calculated for C$_9$H$_{20}$N$_3$O$_3$: 218.1505. found: 218.1537.

[α]$_D^{26}$ +22.4 (c 1.2, H$_2$O)

Example 19

L-DAPA-β-Ala.2HCl

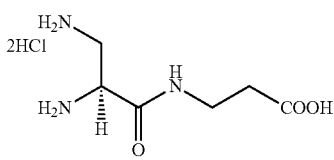

$^1$H NMR (300 MHz, CD$_3$OD) δ 4.40 (t, J=5.8 Hz, 1H), 3.54 (m, 4H); 2.64 (m, 2H);

$^{13}$C NMR (62.5 MHz, CD$_3$OD) δ 174.0, 166.6, 52.1, 41.1, 36.9, 34.2;

MS (ESI) m/z 176 [M+H]$^+$;

HRMS calculated for C$_6$H$_{14}$N$_3$O$_3$ (M+H) 176.1035. found: 176.1068.

[α]$_D^{26}$ +3.8 (c 0.5, H$_2$O)

Example 20

D-DAPA-β-Ala.2HCl

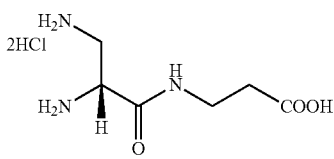

$^1$H NMR (300 MHz, CD$_3$OD) δ 4.40 (t, J=5.8 Hz, 1H), 3.54 (m, 4H); 2.64 (m, 2H);

$^{13}$C NMR (62.5 MHz, CD$_3$OD) δ 174.0, 166.6, 52.1, 41.1, 36.9, 34.2;

MS (ESI) m/z 176 [M+H]$^+$.

Example 21

L-DAPA-L-Phe.2HCl

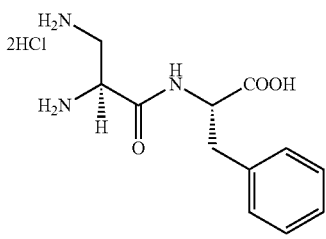

$^1$H NMR (300 MHz, CD$_3$OD) δ 7.32 (m, 5H); 4.79 (dd, J=9.9, 4.4 Hz, 1H); 4.48 (t, J=5.9 Hz, 1H); 3.61 (dd, J=13.9, 6.1 Hz, 1H); 3.51 (dd, J=13.9, 5.7 Hz, 1H); 3.35 (dd, J=14.2, 3.4 Hz, 1H); 3.08 (dd, J=14.2, 9.9 Hz, 1H);

$^{13}$C NMR, (62.5 MHz, CD$_3$OD) δ 175.1, 167.2, 138.2, 130.3, 129.7, 128.1, 68.2, 56.2, 51.7, 41.3, 37.5;

MS (ESI) m/z 252 [M+H]$^+$.

HRMS calculated for C$_{12}$H$_{18}$N$_3$O$_3$ (M+H) 252.1348. found: 252.1341.

[α]$_D^{26}$ +41.8 (c 1.0, H$_2$O)

Example 22

D-DAPA-D-Phe.2HCl

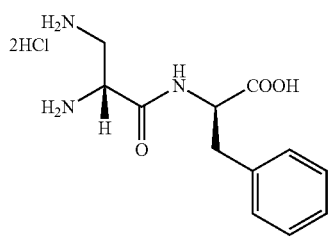

$^1$H NMR (300 MHz, CD$_3$OD) δ 7.32 (m, 5H); 4.79 (dd, J=9.9, 4.4 Hz, 1H); 4.48 (t, J=5.9 Hz, 1H); 3.61 (dd, J=13.9, 6.1 Hz, 1H); 3.51 (dd, J=13.9, 5.7 Hz, 1H); 3.35 (dd, J=14.2, 3.4 Hz, 1H); 3.08 (dd, J=14.2, 9.9 Hz, 1H);

$^{13}$C NMR (62.5 MHz, CD$_3$OD) δ 175.1, 167.2, 138.2 130.3, 129.7, 128.1, 68.2, 56.2, 51.7, 41.3, 37.5;

MS (ESI) m/z 252 [M+H]$^+$, 269 [M+H$_2$O]$^+$.

HRMS calculated for C$_{12}$H$_{18}$N$_3$O$_3$ (M+H) 252.1348. found: 252.1349.

[α]$_D^{26}$ −38.0 (c 1.9, H$_2$O)

Example 23

L-DAPA-L-Val.2HCl

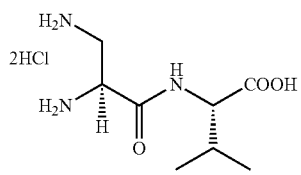

$^1$H NMR (300 MHz, D$_2$O) δ 4.54 (t, J=5.9 Hz, 1H); 4.42 (d, J=5.0 Hz, 1H); 3.60 (d, J=5.9 Hz, 2H); 2.29 (m, 1H); 0.97 (t, J=6.7 Hz, 6H);

$^{13}$C NMR (62.5 MHz, D$_2$O) δ 175.5, 166.9, 59.5, 51.1, 40.3, 30.4, 19.0, 17.6;

MS (ESI) m/z 204 [M+H]$^+$;

HRMS calculated for C$_8$H$_{18}$N$_3$O$_3$: 204.1348. found 204.1365.

[α]$_D^{26}$ +22.2 (c 2.0, H$_2$O)

Example 24

L-DAPA-D-DAPA.3HCl

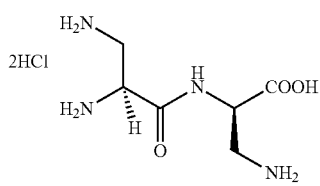

¹H NMR (300 MHz, D₂O) δ 4.60 (m, 1H); 4.55 (dd, J=6.5, 4.9 Hz, 1H); 3.65 (m, 3H); 3.45 (dd, J=13.5, 7.7 Hz, 1H);
¹³C NMR (62.5 MHz, D₂O) δ 171.6, 167.6, 51.8, 51.5, 40.2, 40.1;
MS (ESI) m/z 191 [M+H]⁺;
HRMS calculated for $C_6H_{15}N_4O_3$. 191.1144. found: 191.1146.
$[\alpha]_D^{26}$ −43.4 (c.0.4, H₂O)

Example 28

(2S,3R)-DASA-1-Gly-4-Gly.2HCl

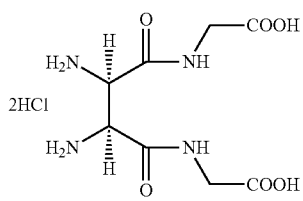

¹H NMR (300 MHz, D₂O) δ 4.61 (s, 1H); 4.43 (s, 1H); 4.06, 4.04 (2s, 4H);
¹³C NMR (62.5 MHz, D₂O) δ 172.9, 172.7, 52.7, 42.5;
MS (ESI) m/z 263 [M+H]⁺; 285 [M+Na]⁺;
HRMS calculated for $C_8H_{15}N_4O_6$: 263.0992. found: 263.0970.
$[\alpha]_D^{26}$ −2.2 (c 1.5, H₂O)

Example 29

(2S,3S)-DASA-1-L-Val-4-L-Val.2HCl

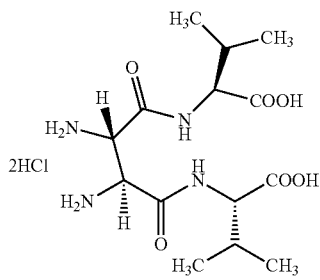

¹H NMR (300 MHz, D₂O) δ 4.78 (m, 1H); 4.65 (m, 1H); 4.35 (m, 1H), 4.21 (m, 1H); 2.12 (m, 2H); 0.85 (m, 12H);
¹³C NMR (62.5 MHz, D₂O) 175.7, 174.8, 59.2, 59.0, 52.8, 52.3, 30.0, 29.7, 18.4, 18.3, 17.2, 16.9.
MS (ESI) m/z 347 [M+H]⁺, 369 [M+Na]⁺;
HRMS calculated for $C_{14}H_{26}N_4O_6Na$: 369.1750. found: 369.1760.
$[\alpha]_D^{26}$ −38.8 (c 0.5, H₂O)

Example 30

(2S,3S)-DASA-1-L-Ile-4-L-Ile.2HCl

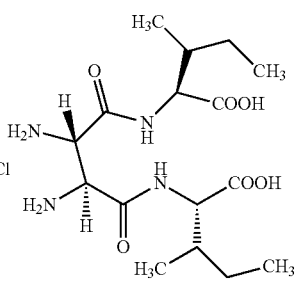

¹H NMR (300 MHz, D₂O) δ 4.78 (m, 1H); 4.62 (m, 1H); 4.40 (m, 2H); 1.75 (m, 6H); 0.85 (m, 12H);
¹³C NMR (62.5 MHz, D₂O) 173.9, 173.1, 164.9, 163.7, 56.3, 54.8, 52.0, 51.8, 39.4, 24.5, 24.4, 22.5, 22.2, 20.5;
MS (ESI) m/z 375 [M+H]⁺, 397 [M+Na]⁺;
HRMS calculated for $C_{16}H_{30}N_4O_6Na$: 397.2063. found: 397.1995.
$[\alpha]_D^{26}$ -18.7 (c 0.3, MeOH)

Example 31

L-DAPA-L-Pro.2HCl

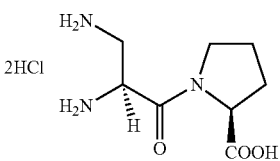

¹H NMR (300 MHz, D₂O) δ 4.62 (m, 1H); 4.39 (m, 1H); 3.62 (d, J=7.6 Hz, 1H); 3.57 (m, 2H); 3.42 (dd, J=13.6, 6.1 Hz, 1H); 2.05 (m, 2H); 1.95 (m, 2H);
¹³C NMR (62.5 Hz, D₂O) δ 173.1, 164.9, 59.6, 52.6, 46.0, 39.2, 28.2, 22.3;
MS (ESI) m/z 202 [M+H];
HRMS calculated for $C_8H_{16}N_3O_3$: 202.1192. found 202.1196.
$[\alpha]_D^{26}$ −72.2 (c 1.3, H₂O)

Example 34

L-DAPA-L-Ala-L-Ala.2HCl

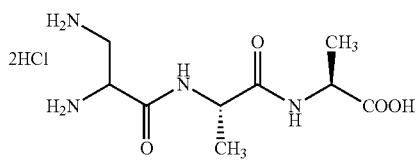

Example 35

L-DAPA-L-Ala-L-Val.2HCl

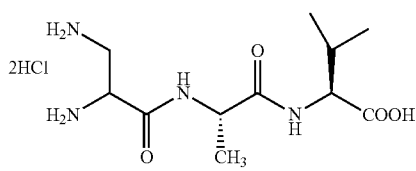

Example 36

L-DAPA-L-Ala-L-Pro.2HCl

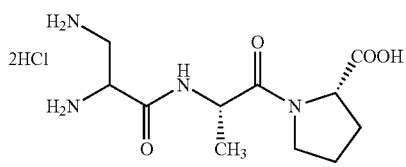

Example 37

D-DAPA-Gly.2HCl

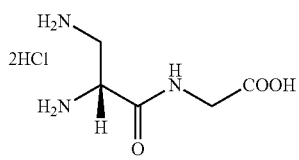

$^1$H NMR (300 MHz, D$_2$O) δ 4.42 (t, J=5.8 Hz, 1H), 4.00 (d, J=18.1 Hz, 1H), 4.10 (d, J=18.1 Hz, 1H), 3.53 (d, J=5.8 Hz, 2H);
$^{13}$C NMR (75 MHz, D$_2$O) δ 172.7, 166.4, 50.5, 41.4, 39.5;
MS (ESI) m/z 162 [M+H]$^+$;
HRMS calculated for C$_5$H$_{12}$N$_3$O$_3$ (M+H) 162.0879. found: 162.0863.
[α]$_D^{25}$ −28.8 (c 1.3, H$_2$O)

Example 38

L-DAPA-GlyOMe.2TFA

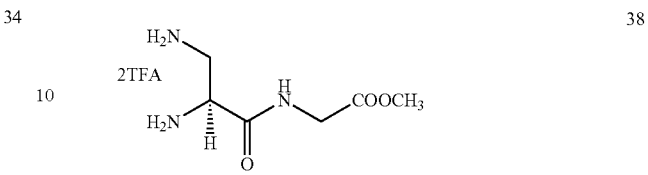

$^1$H NMR (300 MHz, CD$_3$OD) δ 4.39 (t, J=5.7 Hz, 1H), 4.15 (d, J=17.8 Hz, 1H), 4.05 (d, J=17.8 Hz, 1H), 3.75 (s, 3H), 3.52 (dd, J=5.7, 1.5 Hz, 2H);
$^{13}$C NMR (75 MHz, CD$_3$OD) δ 171.9, 167.5, 53.1, 51.9, 42.1, 41.0;
MS (ESI) m/z 176 [M+H]$^+$;
HRMS calculated for C$_6$H$_{14}$N$_3$O$_3$ (M+H) 176.1035. found: 176.1005.
[α]$_D^{25}$ +24.0 (c 1.1, H$_2$O)

Example 39

L-DAPA-GlyNH$_2$.2HCl

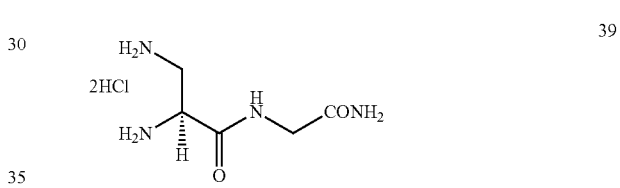

$^1$H NMR (300 MHz, D$_2$O) δ 4.43 (t, J=5.9 Hz, 1H), 4.0 (m, 2H), 3.52 (d, J=5.9 Hz, 2H);
$^{13}$C NMR (75 MHz, D$_2$O) δ 173.1, 166.7, 50.6, 42.1, 39.4;
MS (ESI) m/z 161 [M+H]$^+$;
HRMS calculated for C$_5$H$_{13}$N$_4$O$_2$ (M+H) 161.1039. found: 161.1042.
[α]$_D^{25}$ +38.6 (c 0.23, H$_2$O)

Example 40

D-DAPA-D-Asp.2HCl

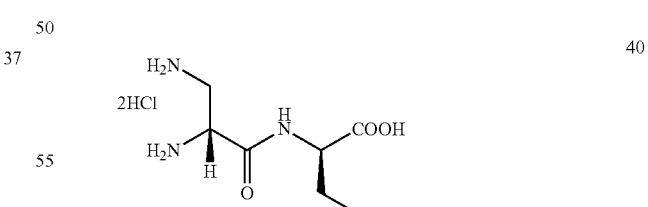

$^1$H NMR (300 MHz, D$_2$O) δ 4.75 (m, 1H), 4.38 (dd, J=6.3, 5.3 Hz, 1H), 3.50 (dd, J=14.4, 5.3 Hz, 1H), 3.42 (dd, J=14.4, 6.4 Hz, 1H), 2.93 (d, J=6.3 Hz, 2H);
$^{13}$C NMR (75 MHz, D$_2$O) δ 174.2, 173.2, 165.9, 50.6, 49.4, 39.4, 35.1;
MS (ESI) m/z 220 [M+H]$^+$;
HRMS calculated for C$_7$H$_{14}$N$_3$O$_5$ (M+H) 220.0933. found: 220.0903.
[α]$_D^{25}$ −32.4 (c 0.7, H$_2$O)

Example 41

D-DAPA-L-Phe.2HCl

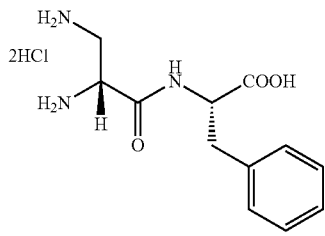

¹H NMR (300 MHz, D₂O) δ 7.25 (m, 5H), 4.72 (dd, J=8.7, 5.6 Hz, 1H), 4.28 (dd, J=6.1, 5.7 Hz, 1H), 3.49 (dd, J=14.3, 6.2 Hz, 1H), 3.43 (dd, J=14.3, 5.7 Hz, 1H), 3.22 (dd, J=14.3, 5.6 Hz, 1H), 3.03 (dd, J=14.3, 8.7 Hz, 1H);
¹³C NMR (75 MHz, D₂O) δ 174.4, 165.8, 136.3, 129.2, 128.8, 127.3, 66.6, 54.6, 50.4, 39.6;
MS (ESI) m/z 252 [M+H]⁺
HRMS calculated for $C_{12}H_{18}N_3O_3$ (M+H) 252.1348. found: 252.1357.
$[\alpha]_D^{25}$ −42.3 (c 1.0, H₂O)

Example 42

D-DAPA-D-Phg.2HCl

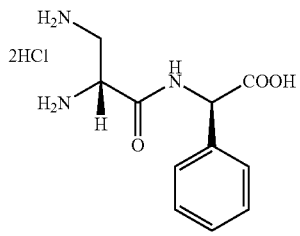

¹H NMR (300 MHz, D₂O) δ 7.32 (s, 5H), 5.43 (s, 1H), 4.38 (m, 1H), 3.52 (d, J=5.9 Hz, 2H);
¹³C NMR (75 MHz, D₂O) δ 173.2, 165.5, 134.4, 129.3, 127.8, 57.6, 50.4, 39.6;
MS (ESI) m/z 238 [M+H]⁺;
HRMS calculated for $C_{11}H_{16}N_3O_3$ (M+H) 238.1192. found: 238.1190.
$[\alpha]_D^{25}$ −81.4 (c 1.0, H₂O)

Example 43

L-DAPA-L-Nle.2HCl

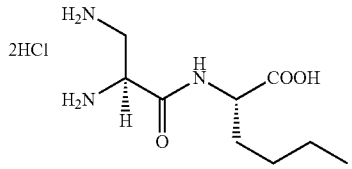

¹H NMR (300 MHz, D₂O) δ 4.35 (m, 2H), 3.48 (d, J=5.9 Hz, 2H), 1.70 (m, 1H), 1.60 (m, 1H), 1.20 (m, 4H), 0.72 (t, J=7.2 Hz, 3H);
¹³C NMR (75 MHz, D₂O) δ 175.6, 166.1, 57.1, 53.6, 50.4, 39.6, 29.9, 27.0, 21.5, 13.0;

MS (ESI) m/z 218 [M+H]⁺;
HRMS calculated for $C_9H_{20}N_3O_3$ (M+H) 218.1505. found: 218.1518.
$[\alpha]_D^{25}$ +6.8 (c 0.5, H₂O)

Example 44

D-DAPA-D-L-Nle.2HCl

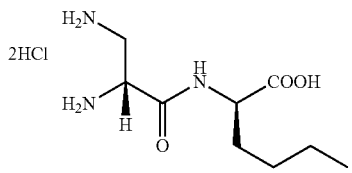

Example 45

D-DAPA-L-Lys.3HCl

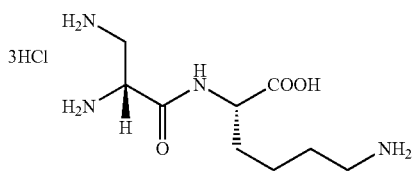

¹H NMR (300 MHz, D₂O) δ 4.42 (dd, J=6.6, 5.1 Hz, 1H), 4.28 (dd, J=8.0, 5.8 Hz, 1H), 3.52 (m, 2H), 2.90 (t, J=7.6 Hz, 2H), 1.82 (m, 2H), 1.60 (m, 2H), 1.37 (m, 2H);
¹³C NMR (75 MHz, D₂O) δ 174.9, 166.1, 53.5, 50.7, 39.5, 39.2, 29.7, 26.3, 22.1;
MS (ESI) m/z 233 [M+H]⁺;
HRMS calculated for $C_9H_{10}N_4O_3$ (M+H) 233.1614. found 233.1624.
$[\alpha]_D^{25}$ −41.0 (c 0.6, H₂O)

Example 46

D-DAPA-L-Leu.2HCl

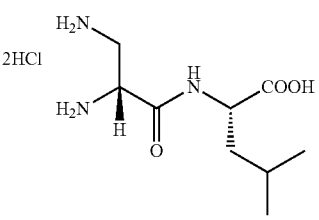

¹H NMR (300 MHz, D₂O) δ 4.37 (dd, J=6.8, 4.9 Hz, 1H), 4.28 (dd, J=8.0, 6.5 Hz, 1H), 3.49 (m, 2H), 1.7-1.5 (m, 3H), 0.85 (d, J=6.2 Hz, 3H), 0.81 (d, J=6.2 Hz, 3H);
¹³C NMR (75 MHz, D₂O) δ 176.0, 166.0, 52.4, 50.7, 39.6, 39.1, 24.5, 22.0, 20.9;
MS (ESI) m/z 218 [M+H]⁺;
HRMS calculated for $C_9H_{20}N_3O_3$ (M+H) 218.1505. found: 218.1506.
$[\alpha]_D^{25}$ −2.5 (c 1.4, H₂O)

Example 47

L-DAPA-(CH₂)-L-Val.2TFA

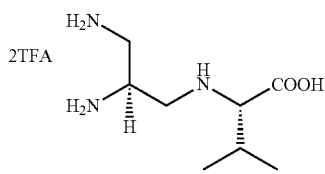

47

¹H NMR (300 MHz, CD₃OD) δ 3.74 (quintet, J=6.2 Hz, 1H), 3.42 (d, J=4.3 Hz, 1H), 3.36 (dd, J=6.2 Hz, 2H), 3.12-3.10 (m, 2H), 2.25-2.14 (m, 1H), 1.05 (d, J=7.0 Hz, 1H);
¹³C NMR (62.5 MHz, CD₃OD) δ 175.9, 68.3, 49.7, 49.1, 41.6, 32.1, 18.9, 18.8;
MS (ESI) m/z 190 [M+H]⁺;
HRMS calculated for $C_8H_{19}N_3O_2$ (M+H) 190.1556. found: 190.1552.
$[\alpha]_D^{26}$ +3.0 (c 1.0, MeOH)

Example 48

L-DAPA-L-Asp.2TFA

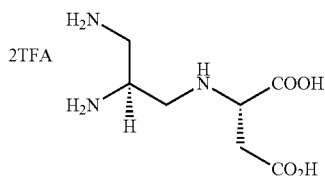

48

¹H NMR (300 MHz, CD₃OD) δ 4.86 (dd, J=6.3, 4.8 Hz, 1H), 4.42 (t, J=5.7 Hz, 1H), 3.57 (dd, J=13.9, 5.8 Hz, 1H), 3.52 (dd, J=13.9, 5.8 Hz, 1H), 2.99 (dd, J=17.2, 6.2 Hz, 1H), 2.91 (dd, J=17.2, 4.6 Hz, 1H);
¹³C NMR (62.5 MHz, D₂O) δ 174.5, 173.8, 167.1, 51.8, 50.8, 41.2, 36.2;
MS (ESI) m/z 220 [M+H]⁺;
HRMS calculated for $C_7H_{24}N_3O_5$ (M+H) 220.0933. found: 220.0950.
$[\alpha]_D^{26}$ +36.6 (c 1.0, MeOH)

Example 49

D-DAPA-L-(4-trifluoromethyl)-Phe.OH.2HCl

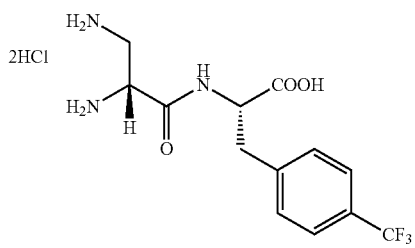

49

¹H NMR (300 MHz, D₂O) δ 7.58 (d, J=7.9 Hz, 2H), 7.35 (d, J=8.1 Hz, 2H), 4.69 (m, 1H), 4.25 (t, J=6.0 Hz, 1H), 3.27 (dd, J=13.9, 5.8 Hz, 1H), 3.17 (d, J=6.0 Hz, 1H), 3.04 (dd, J=14.0, 9.3 Hz, 1H);

¹³C NMR (75 MHz, D₂O) δ 174.1, 165.7, 140.7, 130.0, 129.6 (q, J=32.9 Hz), 125.5, 125.0 (q, J=271.1 Hz), 54.3, 50.7, 39.5, 36.3;
MS (ESI) m/z 320 [M+H]⁺;
HRMS calculated for $C_{13}H_{17}F_3N_3O_3$ (M+H) 320.1222. found: 320.1236.

Example 50

D-DAPA-L-ε-trifluoromethyle-Nle.OH.2HCl

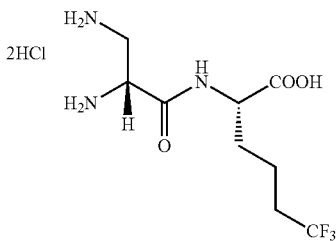

50

Example 51

D-DAPA-L-Nle.2HCl

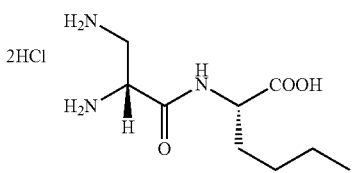

51

¹H NMR (300 MHz, D₂O) δ 4.43 (dd, J=6.6, 5.1 Hz, 1H), 4.33 (dd, J=8.1, 5.7 Hz, 1H), 3.60 (dd, J=14.5, 5.1 Hz, 1H), 3.53 (dd, J=14.5, 6.6 Hz, 1H), 1.82 (m, 2H), 1.34 (m, 4H), 0.86 (t, J=7.2 Hz, 3H);
¹³C NMR (75 MHz, D₂O) δ 175.6, 166.0, 53.8, 50.6, 39.4, 29.9, 27.1, 21.6, 13.0;
MS (ESI) m/z 218 [M+H]⁺;
HRMS calculated for $C_9H_{20}N_3O_3$ (M+H) 218.1505. found: 218.1506.
$[\alpha]_D^{25}$ −43.0 (c 1.4, H₂O)

Example 52

D-DAPA-DL-p-fluoroPhe.2HCl

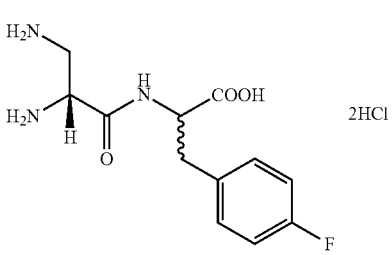

52

¹H NMR (300 MHz, D₂O) δ 7.20-7.15 (m, 2H), 7.03-6.95 (m, 2H), 4.66-4.59 (m, 1H), 4.27 (t, J=5.7 Hz, 0.5H), 4.25 (t, J=5.8 Hz, 0.5H), 3.43 (d, J=6.2 Hz, 0.5H), 3.42 (d, J=5.7

Hz, 0.5H), 3.20-3.10 (m, 1H), 3.17 (d, J=6.0 Hz, 1H), 2.97 (dd, J=14.1, 8.6 Hz, 0.5H), 2.94 (dd, J=14.1, 9.2 Hz, 0.5H);

$^{13}$C NMR (75 MHz, D$_2$O) δ 174.3, 174.2, 165.8, 165.7, 162.8 (d, J=243.7 Hz), 133.0, 132.8, 131.7, 131.6, 116.3, 116.0, 54.7, 54.5, 50.7, 50.4, 39.5, 35.7, 35.5;

MS (ESI) m/z 270 [M+H]$^+$;

HRMS calculated for C$_{12}$H$_{17}$FN$_3$O$_3$ (M+H) 270.1254. found: 270.1255.

Example 53

Biochemical and Biological Results

Figure 1:
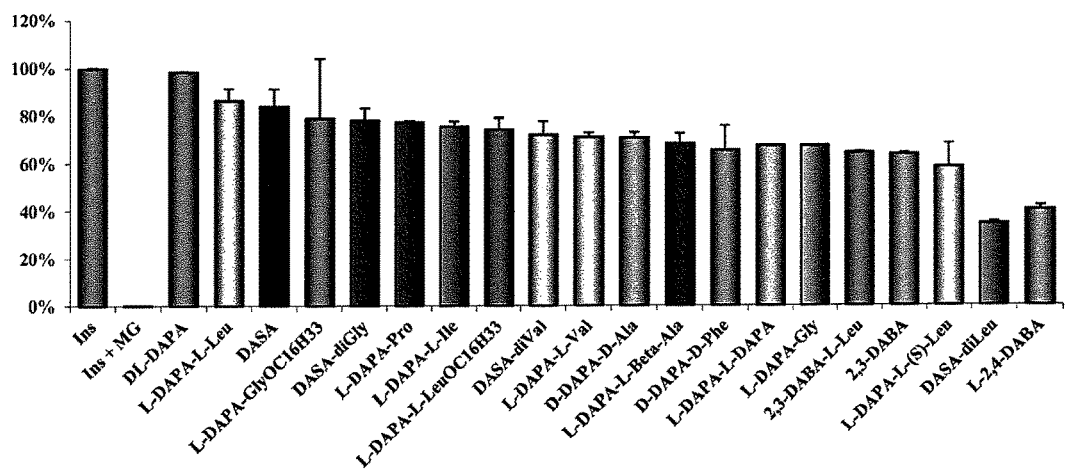
FIG. 1 presents the comparative effects of dicarbonyl scavengers in the form of dihydrochloride according to the present invention and the comparison with DAPA on the modification of insulin (Ins) by methylglyoxal (MG). The percentage of insulin is indicated following incubation with methylglyoxal in the presence or absence of dicarbonyl scavengers. Insulin (0.034 mM) is incubated in vitro in a 10 mM phosphate buffer, pH 7.45 (containing 0.1 M NaCl) with methylglyoxal (3.4 mM) in the presence of dicarbonyl scavengers (4.08 mM) for 21 hours at 37° C. Insulin concentration is measured by HPLC (same conditions as in FIG. 3).

The effectiveness of the novel compounds according to the present invention is shown in the following manner:

Modification of Insulin by Methylglyoxal and the Inhibiting Effect of the Compounds According to the Present Invention: Comparison Between these Products and the Inhibitors of the Prior Art Human insulin (Ins) is incubated with methylglyoxal (MG) under physiological conditions. After 24 hours, the insulin is completely modified, as illustrated in FIG. 1 (Ins+MG).

On the other hand, insulin is incubated with methylglyoxal in the presence of an equimolar quantity of the AGE inhibitors according to the present invention under physiological conditions. After 24 hours, the modification of insulin by MG is considerably reduced, as is illustrated in FIG. 1.

Figure 2:
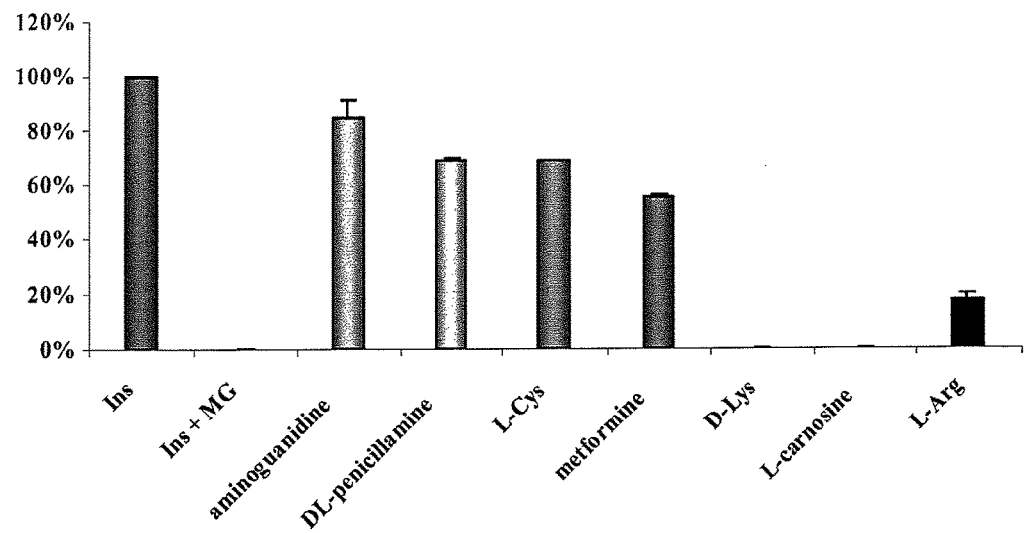
FIG. 2 presents the comparative effects of the dicarbonyl scavengers of the prior art on the modification of insulin by methylglyoxal. The experimental conditions are identical to those described in FIG. 1. The compounds marked with an asterisk (*) are used in hydrochloride form.
Figure 3:
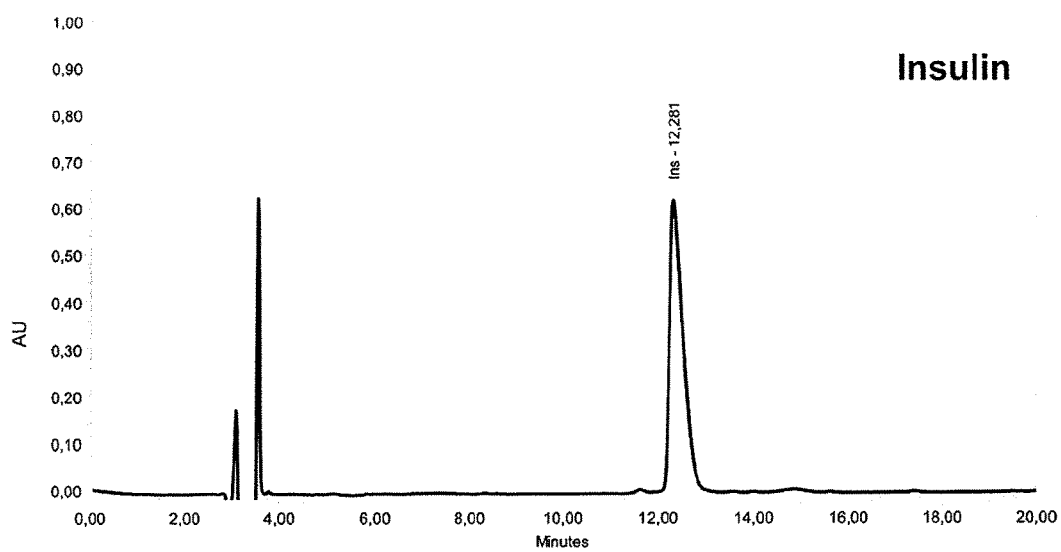
FIGS. 3 to 8 present the results obtained by HPLC for two compounds according to the present invention, L-DAPA-L-Leu (example 1) and L-DAPA-L-Val (example 23), on insulin modifications induced by methylglyoxal. It can be observed that these modifications are prevented. The HPLC conditions are as follows: C-18, Symmetry 300 (4.6×250 mm) column, injection volume 100 μl of reaction mixture; flow 1 ml/min; temperature 40° C.; solvent A: $H_2O$+0.1% TFA; solvent B: 60/40 $CH_3CN/H_2O$+0.1% TFA; linear gradient of 50% B to 55% B in 15 minutes; detection: UV at 215 nm: PDA (chromatograms extracted at 220 nm).
Figure 4:
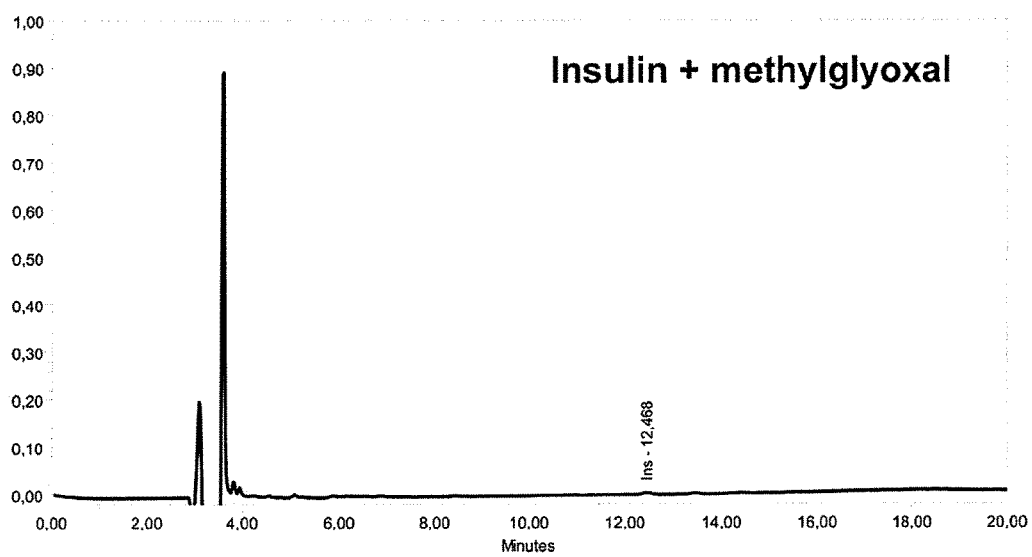
Figure 5:
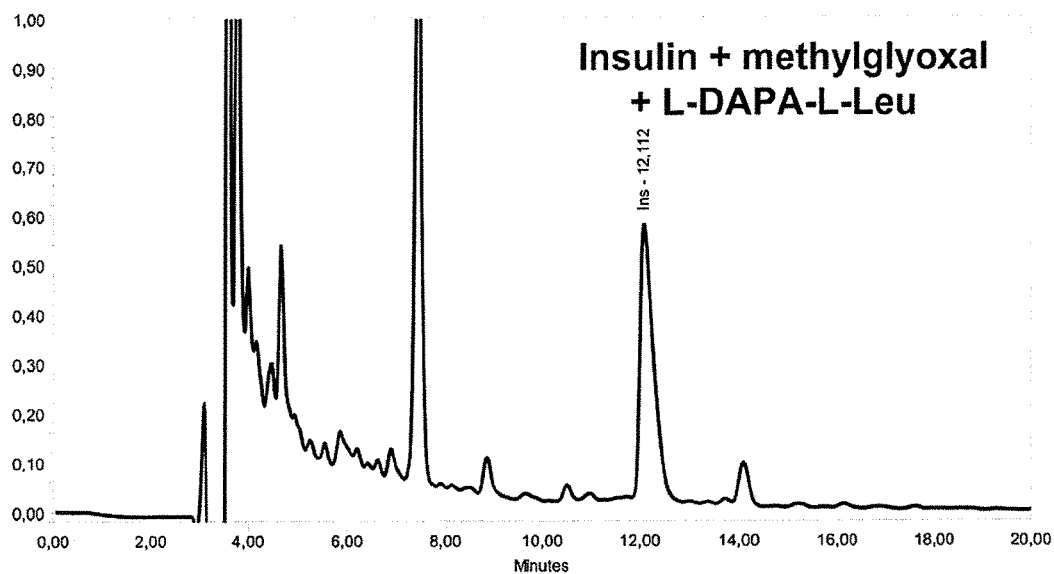

FIG. 2 illustrates the effectiveness of certain known reactive dicarbonyl scavengers in inhibiting the modification of insulin by MG.

Analyses by HPLC clearly demonstrate that some of the AGE inhibitors according to the present invention scavenge methylglyoxal, which can otherwise modify insulin (FIGS. 3 to 8). Certain examples of the effects of the AGE inhibitors according to the present invention on somatostatin-14 (containing 2 Lys) and ribonuclease (RNase) A (containing 10 Lys and 4 Arg) are illustrated in FIGS. 9-10 and 11-13, respectively.

Electrophoresis Studies of the Inhibiting Capacities of the Novel Compounds According to the Present Invention, MG Scavengers, Against AGE Formation Ribonuclease A and lysozyme (10 mg/ml) are incubated in the presence of methylglyoxal (10 mM) or in the presence of methylglyoxal and one of the inhibitors according to the present invention in an equimolar quantity at 37° C. After 48 hours of incubation, the proteins are analyzed by polyacrylamide gel electrophoresis (8%-16% SDS PAGE gel).

Analysis of the results shows that in the presence of methylglyoxal, ribonuclease A and lysozyme exhibit extensive modification, which is indicated by the appearance of the dimer form of the protein.

The addition of one of the inhibitors according to the present invention, namely L-DAPA-L-Leu (example 1), L-DAPA-L-Ile (example 18), L-DAPA-L-Val (example 23), D-DAPA-D-Ala (example 8), (2S,3S)-DASA-L-Leu (example 29), L-DAPA-L-Gly (example 17) or L-DABA-L-Leu (example 12), provides protection from these structural modifications caused by methylglyoxal. The presence of inhibitors according to the present invention largely prevents the formation of cross-linked proteins by scavenging methylglyoxal.

The enzymatic activity of ribonuclease A after treatment with methylglyoxal and the various inhibitors according to the present invention is measured using the methylene blue RNA staining technique of Greiner-Stöffele et al. (Anal. Biochem. (1996) 240, 24).

The results are summarized in table 1 below.

TABLE 1

| Condition | Enzymatic activity (%) |
|---|---|
| Control RNase | 100 |
| RNase + methylglyoxal | 10.11% |
| MG + D-DAPA | 20.32% |
| MG (+) AG | 70.52% |
| MG + L-DABA-L-Leu (example 12) | 80.97% |
| MG + D-DAPA-D-Ala (example 8) | 87.37 |
| MG + L-DAPA-L-Gly (example 17) | 85.61% |
| MG + L-DAPA-L-Phe (example 21) | 70.20% |
| MG + (2S,3S)-DASA-L-Val (example 29) | 75.09% |
| MG + L-DAPA-L-(S)-Leu (example 16) | 75.69% |
| MG + L-DAPA-L-Leu (example 1) | 93.91% |
| MG + L-DAPA-L-Ile (example 18) | 90.77% |
| MG + L-DAPA-L-Val (example 23) | 90.77% |

Enzyme kinetics as measured by spectrophotometry at 688 nm show that the inhibition of enzymatic activity caused by methylglyoxal is considerably reduced in the presence of the inhibitors according to the present invention.

Comparative analyses (by electrophoresis and by enzyme activity measurements) are carried out on ribonuclease A or lysozyme using aminoguanidine (AG) as the inhibitor. The results clearly show that the inhibitors according to the present invention are considerably more effective than AG.

The same trend is observed for lysozyme (containing 6 Lys and 11 Arg) during tests carried out under the same conditions as for ribonuclease A.

MG reacts with a protein's lysine and arginine residues, thus altering the charges on the modified polypeptide. This was demonstrated by the electrophoresis of glyoxalase I treated with MG under non-denaturing conditions. The exposure of glyoxalase I to MG (10 mM) for 24 hours increases the mobility of the protein toward the positive electrode, a change that is consistent with the loss of positive charges from the ϵ-amino and guanidino groups and the gain of negative charges. When the inhibitors according to the present invention (L-DAPA-L-Leu (example 1) or L-DAPA-L-Ile (example 18)) are included in the incubation mixture, the presence of these compounds inhibits the gain of negative charge.

The incubation of glyoxalase I, a key protein in the α-oxoaldehyde detoxification system, in the presence of methylglyoxal, modifies the protein. This modification causes a change in charge and a 50% decrease in enzymatic activity compared to the control.

The addition of the compounds according to the present invention (L-DAPA-L-Leu or L-DAPA-L-Ile) prevents the inhibition exerted by methylglyoxal and protects against structural modifications.

Comparative results obtained by electrophoresis show that aminoguanidine (AG) is much less effective than AGE inhibitors (according to the present invention) with respect to the protecting effect of these compounds against the structural modifications of ribonuclease A induced by MG. The AGE inhibitors according to the present invention, namely L-DAPA-L-Leu (example 1) and L-DAPA-L-Ile (example 18), or AG (10 mM) are incubated with MG and ribonuclease A for 40 hours at 37° C.

Growth of EA Cells in the Presence of MG Scavengers According to the Present Invention and of the Prior Art and/or Methylglyoxal The cells used for the test are from the EA.hy 926 cell line, which are endothelial cells obtained by the hybridization of human umbilical vein endothelial cells (HUVECs) with lung cancer cells (A549). The EA.hy 926 endothelial cells are incubated in Dulbecco's modified Eagle's Medium (DMEM) enriched with 10% fetal calf serum. The cells are incubated in 12-well plates. Each well initially contains 100,000 cells. Cell growth is achieved by incubating the cells in 2 ml of culture medium after adding or not adding the various potential inhibitors (1 mM) and/or methylglyoxal (600 µM) for 48 hours at 37° C. in a moist atmosphere with 5% $CO_2$.

The number of cells is evaluated in the following way:

The cells are stained using the (4,5-dimethylthiazol-2-yl)-2,5-diphenyltetrazolium bromide (MTT) assay. MTT penetrates in the cell where it is converted into formazan. The quantity of formazan formed is proportional to the number of living cells.

The results are expressed as a relative percentage of the number of cells after treatment compared to the number of control cells without treatment [100*OD (treated cells)/OD (control cells)]. Detection is carried out by UV/visible spectrophotometry at 570 nm.

Principle: MTT (yellow) penetrates the cell and is converted into an insoluble blue compound, formazan, by cleavage of its tetrazolium rings by the mitochondrial dehydrogenase enzymes of living cells. Formazan is solubilized by isopropanol. The number of cells is proportional to the quantity of formazan formed and its absorbance.

Figure 6:
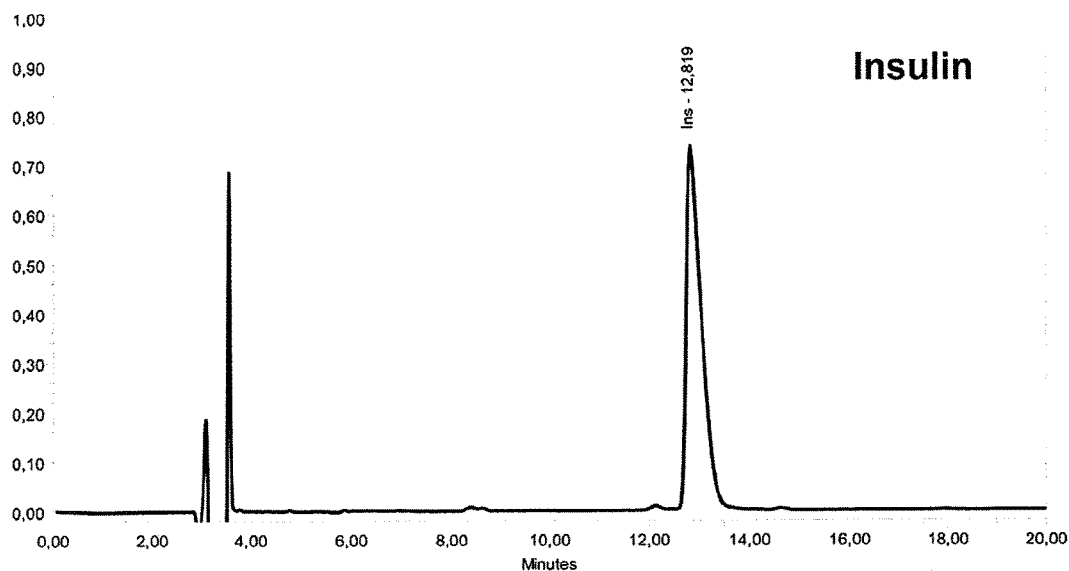
Figure 7:
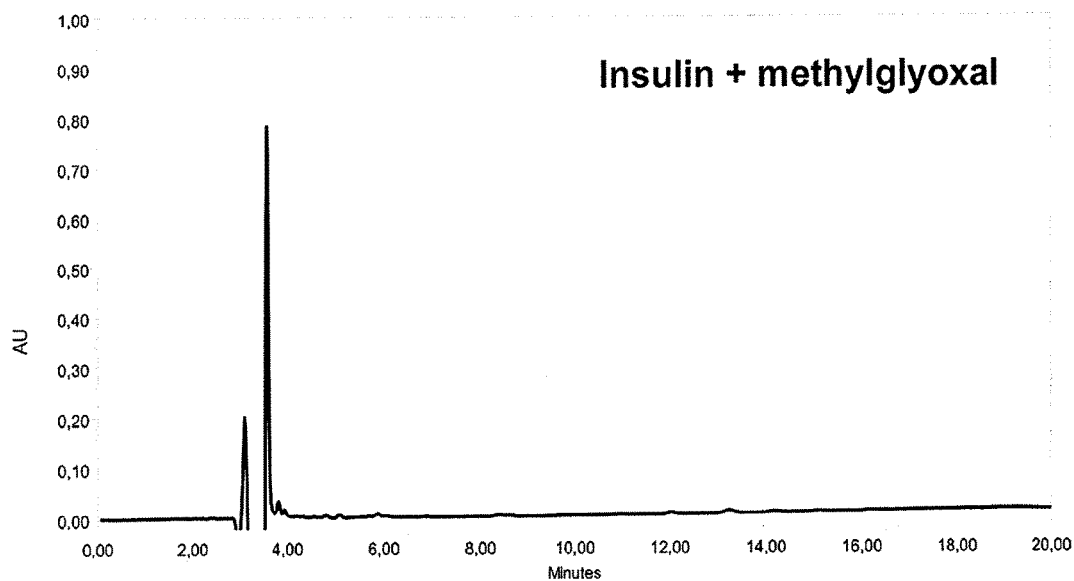
Figure 8:
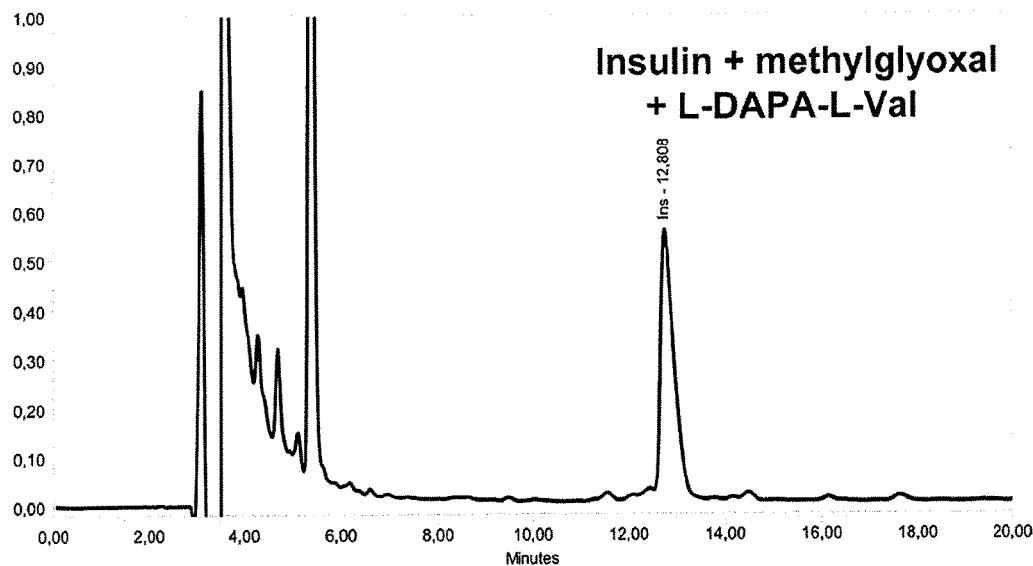
Figure 9:
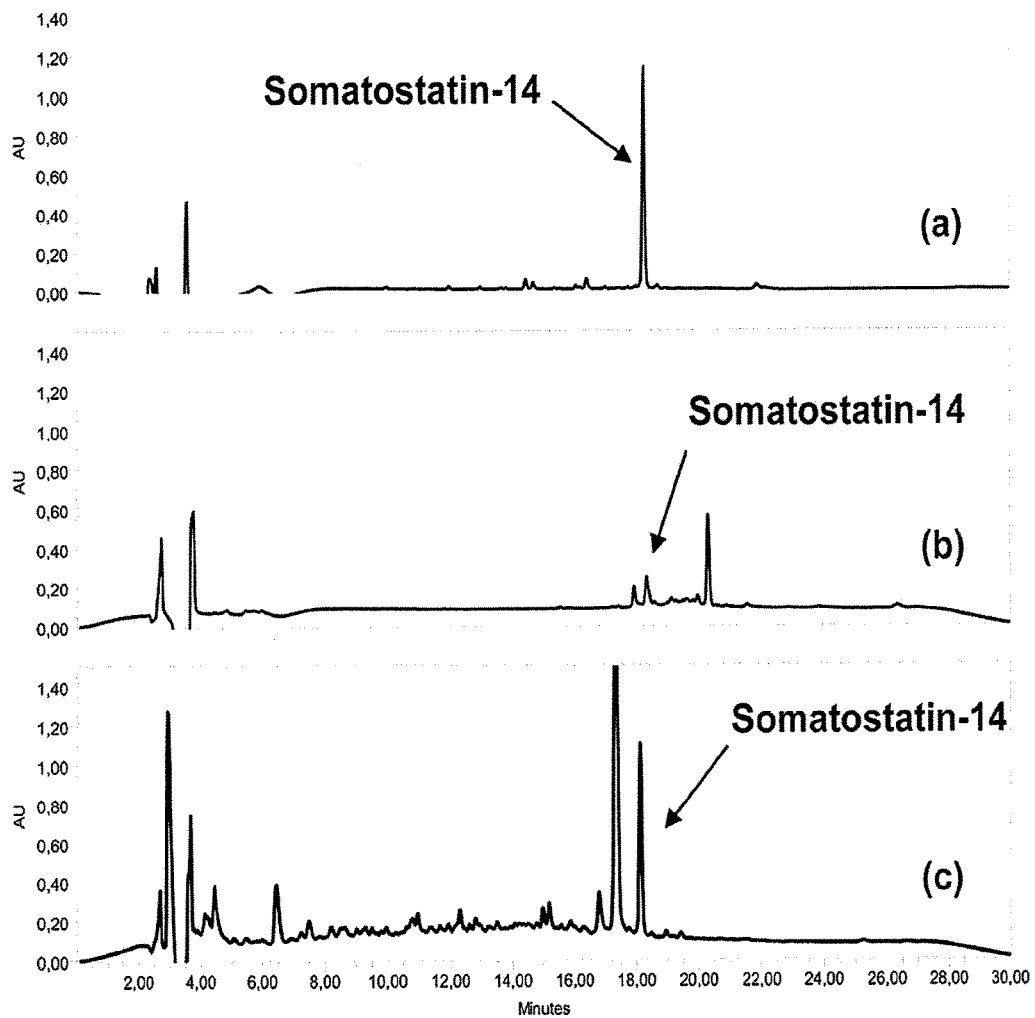
FIGS. 9 and 10 present the results obtained by HPLC for two compounds according to the present invention, L-DAPA-L-Leu (example 1) and L-DAPA-L-Val (example 23), on somatostatin-14 modifications induced by methylglyoxal. HPLC conditions are as follows: C-18, Symmetry 300 (4.6×250 mm) column, injection volume 100 μl of reaction mixture; flow 1 ml/min; solvent A: $H_2O$+0.1% TFA; solvent B: 80/20 $CH_3CN/H_2O$+0.1% TFA; linear gradient: from 20% B to 60% B in 15 minutes and isocratic from 60% B for 10 minutes; ambient temperature; detection: PDA (chromatograms extracted at 215 nm). The compounds according to the present invention prevent the modifications induced by methylglyoxal.
Figure 10:
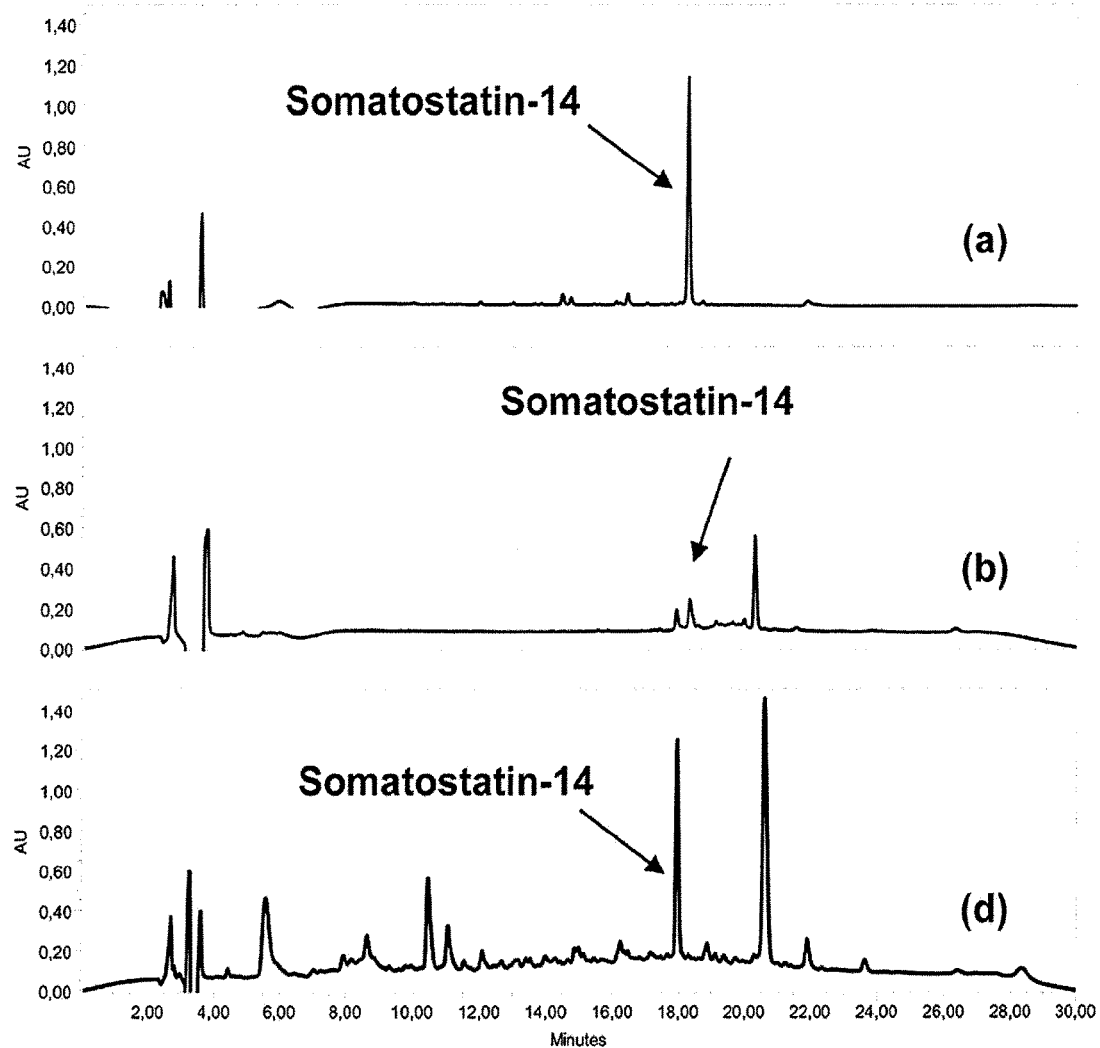

As illustrated in FIG. 6, methylglyoxal (MG) suppresses cell growth.

The results are summarized in table 2 below.

TABLE 2

Cell growth in the presence or absence of MG and MG scavengers

| MG scavengers | Cells + MG scavengers (A) | SD | Cells + MG scavengers + Methylglyoxal (B) | SD | Difference (B) − (A) |
|---|---|---|---|---|---|
| 0 | 100 | 0 | 24 | | |
| Aminoguanidine | 97 | 6 | 92 | 5 | −5 |
| L-DAPA-L-Val•2HCl (example 23) | 94 | 8 | 93 | 3 | −1 |
| L-DAPA-L-Leu•2HCl (example 1) | 94 | 16 | 81 | 7 | −13 |
| Carnosine | 99 | 0.2 | 50 | 3 | −49 |
| L-DAPA-L-Ile•2HCl (example 18) | 86 | 6 | 79 | 4 | −7 |
| (2S,3S)-DASA-L-Val•2HCl (example 29) | 85 | 5 | 70 | 9 | −15 |
| L-DABA-L-leu•2HCl (example 12) | 77 | 15 | 73 | 9 | −4 |
| L-DAPA-L-Phe•2HCl (example 21) | 77 | 6 | 71 | 7 | −6 |
| Metformin | 91 | 4 | 45 | 4 | −46 |
| D-DAPA | 83 | 3 | 68 | 13 | −15 |
| D-DAPA-D-Ala•2HCl (example 8) | 77 | 6 | 71 | 7 | −6 |
| L-DAPA-L-(S)-Leu•2HCl (example 16) | 71 | | 74 | | +3 |
| L-DAPA-Gly•2HCl (example 17) | 54 | 8 | 50 | 10 | −4 |
| (2S,3R)-DASA-Gly•2HCl (example 28) | 61 | 8 | 54 | 11 | −7 |
| L-Lys | 81 | | 43 | | −38 |

Mean of 3 experiments

The addition of aminoguanidine (AG), a known MG scavenger, suppresses this process in a spectacular manner. The same trend can be observed with the compounds according to the present invention, in particular L-DAPA-L-Val (example 23), L-DAPA-L-Leu (example 1) and L-DAPA-L-Ile (example 18). Other known MG scavengers, such as carnosine and metformin, proved less effective in this test. Additional examples of the inhibiting effect of the compounds according to the present invention compared to the suppression of cell growth by MG are illustrated in FIG. 15.

These results show that the compounds according to the present invention are non-toxic with respect to EA cells. This is true in particular for L-DAPA-L-Val.2HCl (example 23), L-DAPA-L-Leu.2HCl (example 1), L-DAPA-L-Ile.2HCl (example 18), (2S,3S)-DASA-L-Val.2HCl (example 29) and L-DAPA-L-Leu.2TFA (example 3) for which the number of cells is lower by less than 15% compared to the number of control cells growing without the addition of any product. The composition of the molecule's diamino moiety is not involved in toxicity nor is the associated salt. Indeed, L-DAPA, (2S,3S)-DASA and D-DAPA, as well as HCl and TFA salts, are found in toxic and nontoxic products. It can be noted that the non-toxicity of the compounds increases their MG-scavenging activity compared to cells growing with MG alone. The difference between the relative values of the number of cells growing with the analyzed compound and the cells growing in the presence of MG and the analyzed compound makes it possible to evaluate the product's role as a MG scavenger. Eight compounds according to the present invention possess this activity in particular, namely L-DAPA-L-Val.2HCl (−3) (example 23), L-DAPA-L-Leu.2HCl (−13) (example 1), L-DAPA-L-Ile.2HCl (−9) (example 18), (2S,3S)-DASA-L-Val.2HCl (−15) (example 29), L-DAPA-L-Leu.2TFA (−18) (example 3), L-DABA-L-Leu.2HCl (−4) (example 12) and L-DAPA-L-Phe.2HCl (−6) (example 21). Two other compounds also exhibit scavenging activity, namely D-DAPA-D-Ala.2HCl (+1) (example 8) and L-DAPA-Gly.2HCl (+3) (example 17). On the other hand, their cell toxicity is higher (39% and 43%, respectively). It can be noted that metformin is a weak scavenger even though this molecule has extremely low toxicity at this concentration.

Test of Mutagenicity of Two Compounds According to the Present Invention: L-DAPA-L-Leu (Example 1) and L-DAPA-L-Val (Example 23)

An Ames test was performed with L-DAPA-L-Leu (example 1) and L-DAPA-L-Val (example 23) alone and in combination with methylglyoxal on human liver S9 fractions and on seven strains of *Salmonella*.

The concentrations used in the Ames test were as follows:
L-DAPA-L-Leu alone or L-DAPA-L-Val alone: 10 μM, 1 μM and 0.1 μM.
L-DAPA-L-Leu/methylglyoxal mixture or L-DAPA-L-Val/methylglyoxal mixture: 10 μM, 1 μM and 0.1 μM.
Methylglyoxal: 10 μM.

The results are summarized in table 3 below.

TABLE 3

| Substance tested | Concentration (μM) | Human S9 | Six mixed strains | Strain TA98 |
|---|---|---|---|---|
| L-DAPA-L-Leu (example 1) | 10/1/0.1 | No | − | − |
| L-DAPA-L-Val (example 23) | 10/1/0.1 | No | − | − |
| L-DAPA-L-Leu example 1: (metabolites) | 10/1/0.1 | Yes | − | − |
| L-DAPA-L-Val example 23: (metabolites) | 10/1/0.1 | Yes | − | − |
| L-DAPA-L-Leu (example 1) + methylglyoxal | 10/1/0.1 | No | − | − |
| L-DAPA-L-Val (example 23) + methylglyoxal | 10/1/0.1 | No | − | − |
| L-DAPA-L-Leu (example 1) + methylglyoxal (metabolites) | 10/1/0.1 | Yes | − | − |
| L-DAPA-L-Val (example 23) + methylglyoxal (metabolites) | 10/1/0.1 | Yes | − | − |
| Methylglyoxal | 10 | No | − | − |
| Methylglyoxal (metabolites) | 10 | Yes | − | − |
| Positive control (4NQO)/2NF) | 2.6/9.5 | No | + | + |
| Positive control (2AA) (metabolites) | 51.7 | Yes | + | + |
| Negative control (solvent) | − | No | − | − |
| Negative control (solvent) | − | Yes | − | − |

−: non-mutagenic
+: mutagenic

Tested alone or in combination with methylglyoxal, neither substance (L-DAPA-L-Leu or L-DAPA-L-Val) was mutagenic for TA98, the mixed strains or the human liver S9 fractions at the concentrations tested. The metabolites produced by the human liver S9 fractions were not mutagenic at the concentrations tested.

The invention claimed is:

1. A method for treating a patient suffering from a disease or condition associated with reactive α-dicarbonyl compounds, the method comprising scavenging methylglyoxyl comprising the administration of an effective amount of a compound of following general formula I:

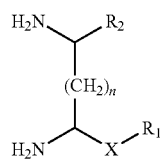

wherein:
X represents $CH_2$, C=O, or C=S;
$R_1$ represents
NH—$R_3$—(C=O)$R_4$ or

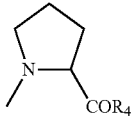

wherein
$R_3$ represents
a $C_1$-$C_{12}$ alkyl group optionally substituted by one or more groups selected from the group consisting of a halogen atom, a —$CF_3$, a phenyl, a phenol, a —COOH, an amine, and a phenyl group substituted by one or more halogen atoms or by one or more $CF_3$ groups; or
a phenyl group, optionally, substituted by an amine, an OH group, one or more halogen atoms, or one or more $CF_3$ groups; and
$R_4$ represents OH, $NH_2$, or a $C_1$-$C_{30}$ alkoxy;
n=0; and
$R_2$ represents H, $COR_1$, or a $C_1$-$C_6$ alkyl group optionally substituted by one or more halogen atoms, or by one or more $CF_3$ groups;
or the pharmaceutically acceptable addition salts, isomers, enantiomers and diastereoisomers thereof and mixtures thereof,
to a patient in need thereof, and wherein the disease or condition is selected from the group consisting of cataract, uremia, artheriosclerosis, Alzheimer's disease, Parkinson's disease, diabetic ulcers, type 2 diabetes, diabetic retinopathy, diabetic nephropathy, microangiopathies, and macroangiopathies.

2. The method according to claim 1, wherein said compound is represented by the following general formula II:

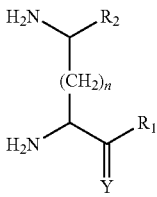

wherein:
$R_1$ represents NH—$R_3$—(C=O)$R_4$ or

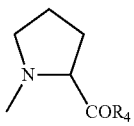

wherein
$R_3$ represents
a $C_1$-$C_{12}$ alkyl group, optionally substituted by one or more groups selected from the group consisting of a halogen atom, a —$CF_3$, a phenyl, a phenol, a —COOH, an amine, and a phenyl group substituted by one or more halogen atoms, or by one or more $CF_3$ groups; or
a phenyl group, optionally substituted by an amine, an OH group, one or more halogen atoms, or one or more $CF_3$ groups; and
$R_4$ represents OH, $NH_2$, or a $C_1$-$C_{30}$ alkoxy;
$R_2$ represents H, $COR_1$, or a $C_1$-$C_6$ alkyl group optionally substituted by one or more halogen atoms, or by one or more $CF_3$ groups; and Y represents an oxygen or sulfur atom;
or the pharmaceutically acceptable addition salts, isomers, enantiomers and diastereoisomers thereof and mixtures thereof.
3. The method according to claim 1, wherein said compound is selected among
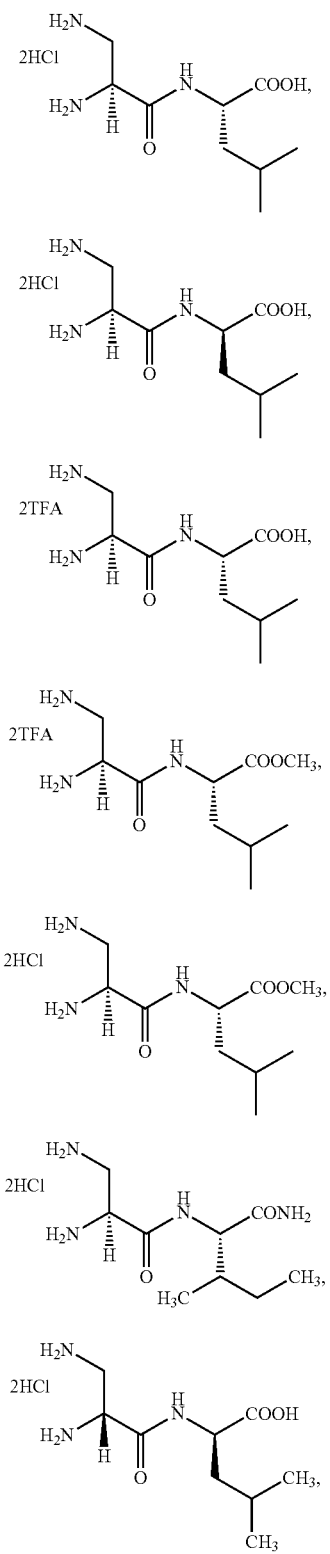
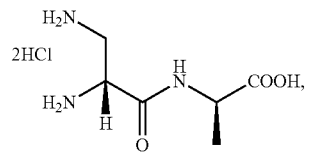
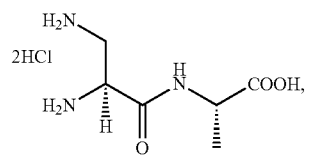
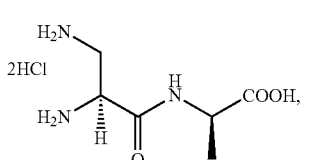
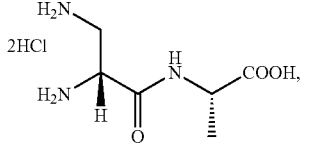
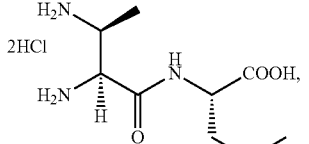
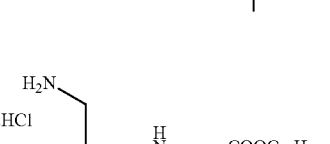
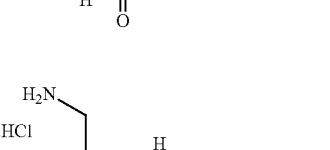
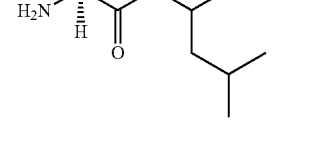

-continued
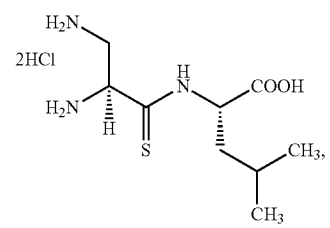
16
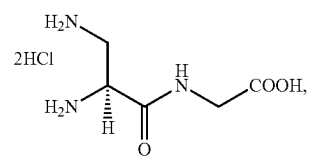
17
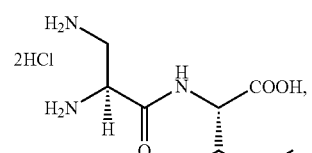
18
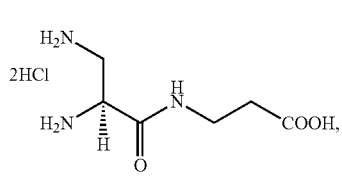
19
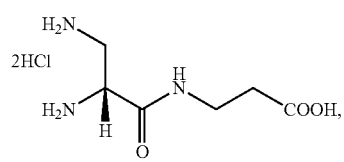
20
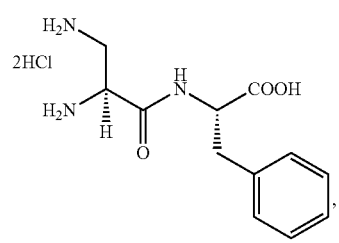
21
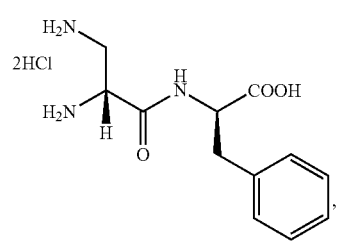
22
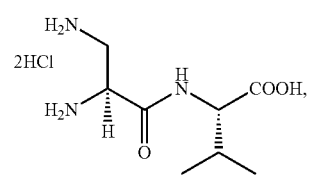
23
-continued
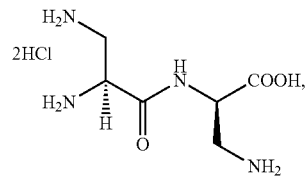
24
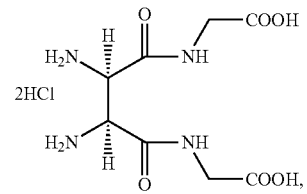
28
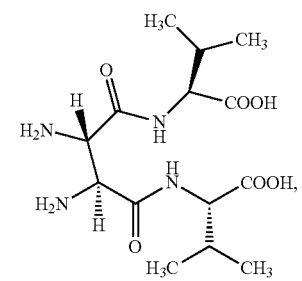
29
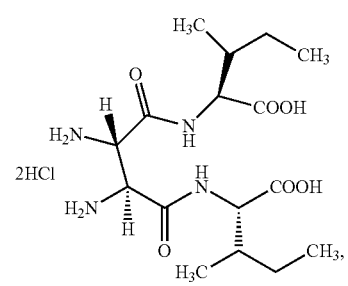
30
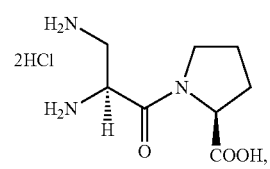
31
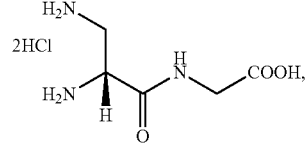
37
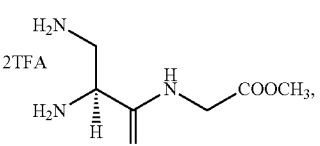
38
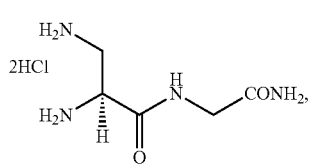
39

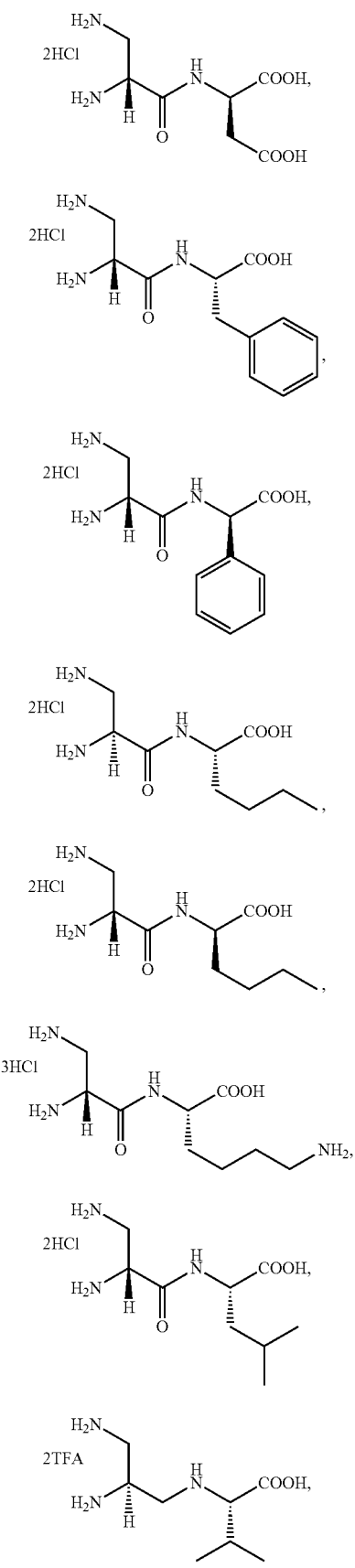

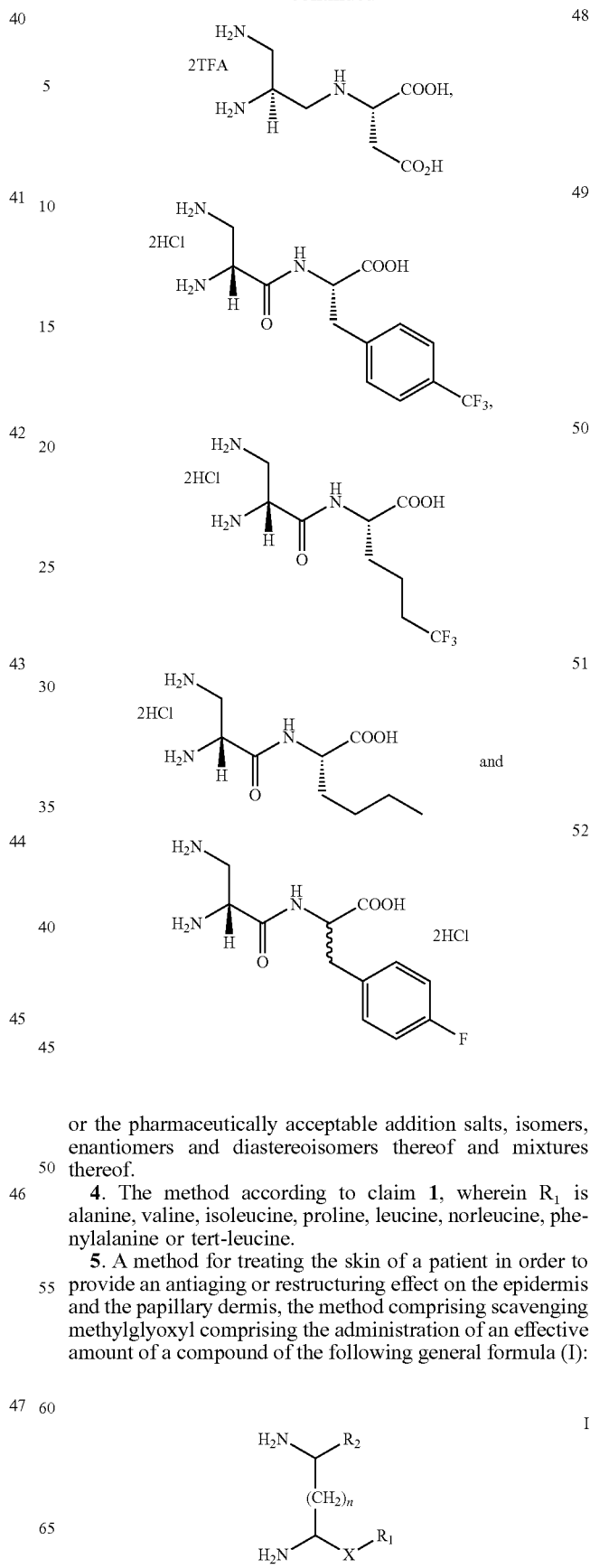

or the pharmaceutically acceptable addition salts, isomers, enantiomers and diastereoisomers thereof and mixtures thereof.

4. The method according to claim 1, wherein $R_1$ is alanine, valine, isoleucine, proline, leucine, norleucine, phenylalanine or tert-leucine.

5. A method for treating the skin of a patient in order to provide an antiaging or restructuring effect on the epidermis and the papillary dermis, the method comprising scavenging methylglyoxyl comprising the administration of an effective amount of a compound of the following general formula (I):

wherein:

X represents $CH_2$, C=O, C=S or CHOH;

$R_1$ represents

NH—$R_3$—(C=O)$R_4$ or

[structure: N-methylpyrrolidine with COR$_4$ substituent]

wherein $R_3$ represents a $C_1$-$C_{12}$ alkyl group optionally substituted by one or more groups selected from the group consisting of a halogen atom, a —$CF_3$, a phenyl, a phenol, a —COOH, an amine, and a phenyl group substituted by one or more halogen atoms or by one or more $CF_3$ groups; or a phenyl group, optionally, substituted by an amine, an OH group, one or more halogen atoms, or one or more $CF_3$ groups; and $R_4$ represents OH, NH2, or a $C_1$-$C_{30}$ alkoxy;

n=0; and $R_2$ represents H, $COR_1$, or $C_1$-$C_6$ alkyl group optionally substituted by one or more halogen atoms, or by one or more $CF_3$ groups;

or the pharmaceutically acceptable addition salts, isomers, enantiomers and diastereoisomers thereof and mixtures thereof, to a patient in need thereof.

6. The method according to claim 1, wherein the compound has the following formula:

[structure with 2HCl, H$_2$N groups, COOH]

7. A method for treating a patient suffering from a disease or condition associated with reactive α-dicarbonyl compounds, the method comprising scavenging methylglyoxyl comprising the administration of an effective amount of a compound selected from the group consisting of 1
[structure with 2HCl, H$_2$N, COOH]

2
[structure with 2HCl, H$_2$N, COOH]

3
[structure with 2TFA, H$_2$N, COOH]

4
[structure with 2TFA, H$_2$N, COOCH$_3$]

5
[structure with 2HCl, H$_2$N, COOCH$_3$]

6
[structure with 2HCl, H$_2$N, CONH$_2$, CH$_3$]

7
[structure with 2HCl, H$_2$N, COOH, CH$_3$]

8
[structure with 2HCl, H$_2$N, COOH]

9
[structure with 2HCl, H$_2$N, COOH]

10
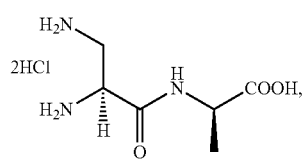
11
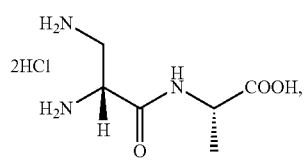
12
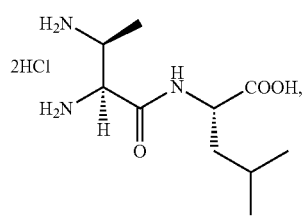
13
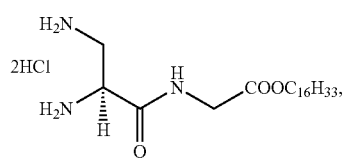
14
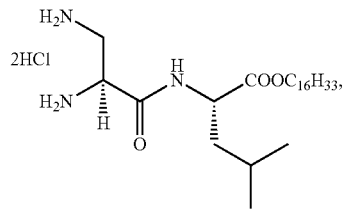
15
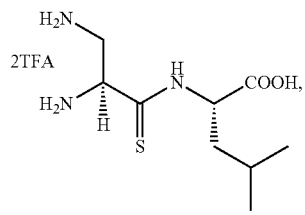
16
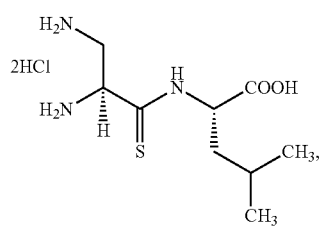
17
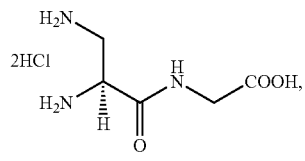
18
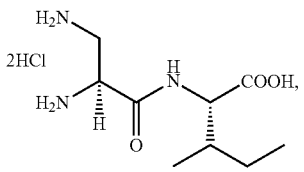
19
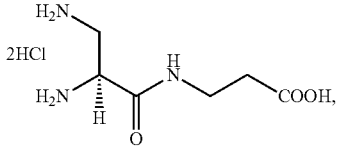
20
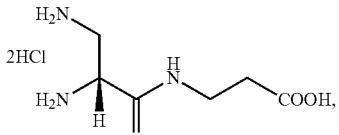
21
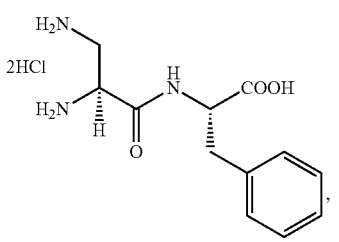
22
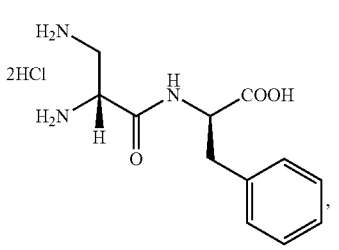
23
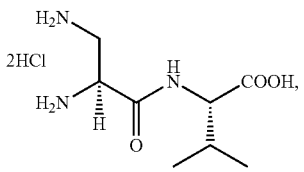
24
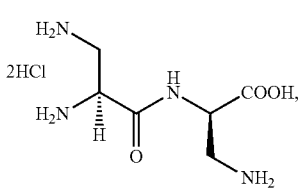
28
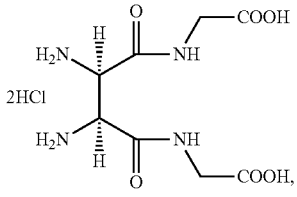

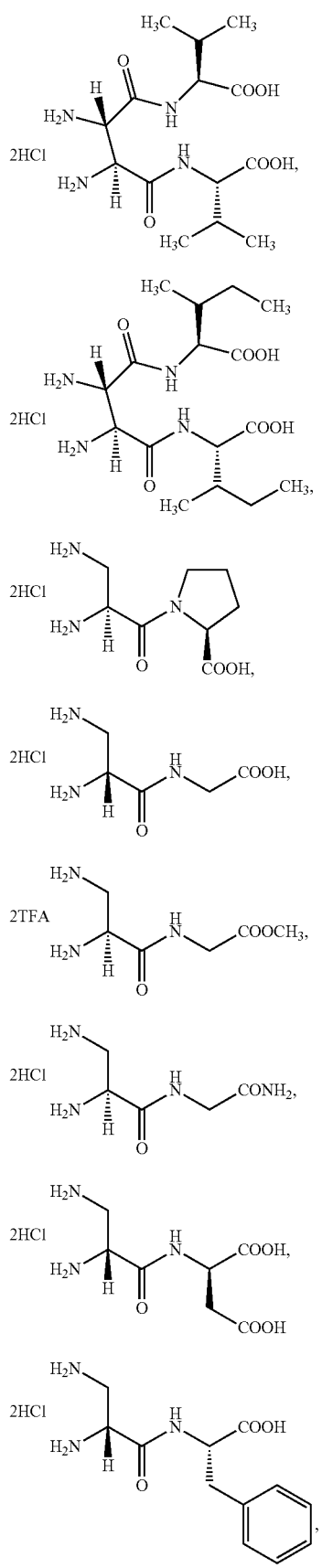
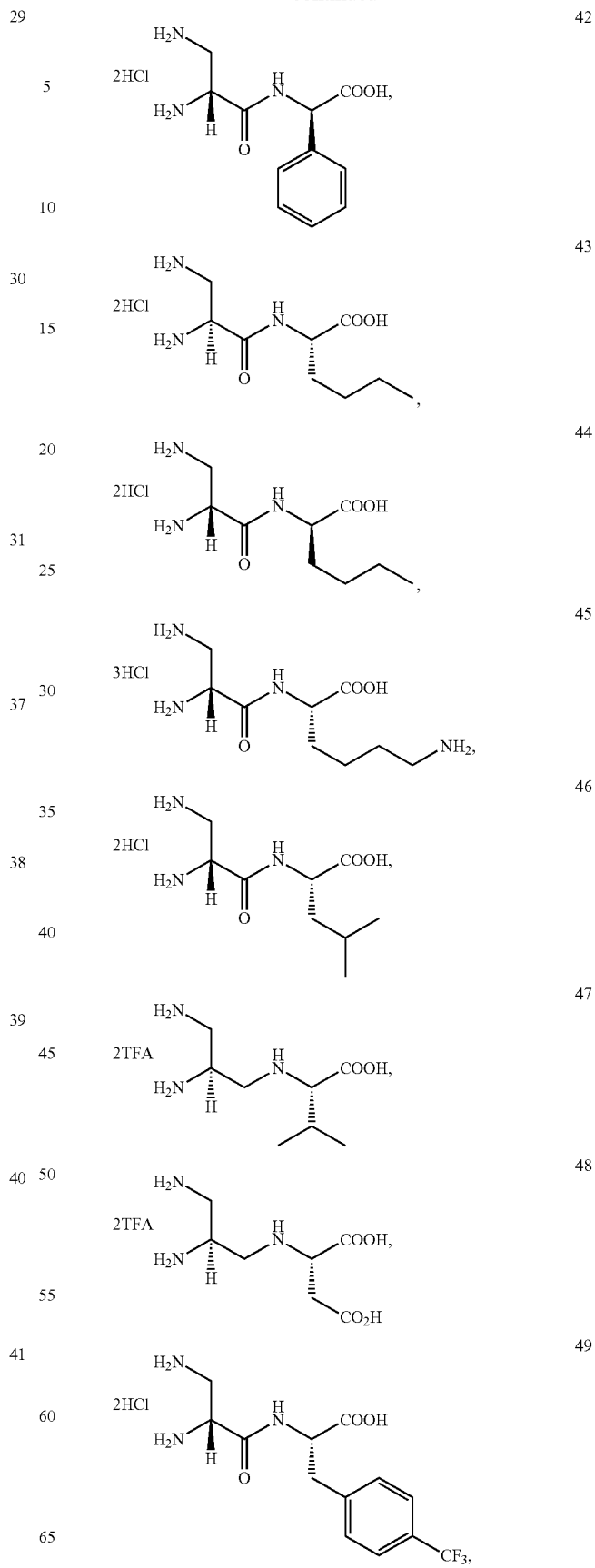

-continued

[Structure 50: dipeptide with CF3 group, 2HCl]

[Structure 51: dipeptide with pentyl chain, 2HCl, "and"]

[Structure 52: dipeptide with 4-fluorobenzyl group, 2HCl]

or the pharmaceutically acceptable addition salts, isomers, enantiomers and diastereoisomers thereof and mixtures thereof, and wherein the disease or condition is selected from the group consisting of cataract, uremia, artheriosclerosis, Alzheimer's disease, Parkinson's disease, type 2 diabetes, diabetic retinopathy, diabetic nephropathy, microangiopathies, and macroangiopathies.

8. The method of claim 7, wherein the compound is selected from the group consisting of

[Structure: dipeptide with leucine, 2HCl]

[Structure: dipeptide with isoleucine-like group, 2HCl]

[Structure: dipeptide with leucine, 2HCl]

[Structure: thioamide dipeptide with leucine, 2HCl]

-continued

[Structure: dipeptide with glycine, 2HCl]

[Structure: dipeptide with isoleucine, 2HCl]

[Structure: dipeptide with phenylalanine, 2HCl]

[Structure: dipeptide with valine, 2HCl, "and"]

[Structure: tripeptide with two valine-like groups, 2HCl]

9. A method for treating a patient suffering from a disease or condition selected from the group consisting of cataract, uremia, artheriosclerosis, Alzheimer's disease, Parkinson's disease, diabetic ulcers, type 2 diabetes, diabetic retinopathy, diabetic nephropathy, microangiopathies, and macroangiopathies, the method comprising administering to a patient in need thereof an effective amount of a compound of following general formula I:

$$\text{H}_2\text{N}-\overset{R_2}{\underset{(CH_2)_n}{\big|}}-\text{CH}-\text{X}-R_1 \quad \text{with NH}_2 \text{ branch} \qquad \text{I}$$

wherein:
X represents $CH_2$, C=O, or C=S;
$R_1$ represents
$NH-R_3-(C=O)R_4$ or

[Structure: N-methylpyrrolidine with COR4]

wherein
$R_3$ represents
a $C_1$-$C_{12}$ alkyl group optionally substituted by one or more groups selected from the group consisting of a halogen atom, a —CF$_3$, a phenyl, a phenol, a —COOH, an amine, and a phenyl group substituted by one or more halogen atoms or by one or more CF$_3$ groups; or a phenyl group, optionally substituted by an amine, an OH group, one or more halogen atoms, or one or more CF$_3$ groups; and R$_4$ represents OH, NH$_2$, or a C$_1$-C$_{30}$ alkoxy;

n=0; and

R$_2$ represents H, COR$_1$, or a C$_1$-C$_6$ alkyl group optionally substituted by one or more halogen atoms, or by one or more CF$_3$ groups;

or the pharmaceutically acceptable addition salts, isomers, enantiomers and diastereoisomers thereof and mixtures thereof.

10. A method for treating the skin of a patient in order to provide an antiaging or restructuring effect on the epidermis and the papillary dermis, the method comprising administering to a patient in need thereof an effective amount of a compound of following general formula I:

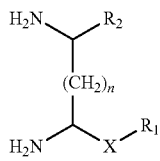

wherein:
X represents CH$_2$, C=O, or C=S;

R$_1$ represents
NH—R$_3$—(C=O)R$_4$ or

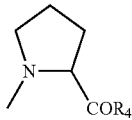

wherein
R$_3$ represents
a C$_1$-C$_{12}$ alkyl group optionally substituted by one or more groups selected from the group consisting of a halogen atom, a —CF$_3$, a phenyl, a phenol, a —COOH, an amine, and a phenyl group substituted by one or more halogen atoms or by one or more CF$_3$ groups; or a phenyl group, optionally substituted by an amine, an OH group, one or more halogen atoms, or one or more CF$_3$ groups; and R$_4$ represents OH, NH$_2$, or a C$_1$-C$_{30}$ alkoxy;

n=0; and

R$_2$ represents H, COR$_1$, or C$_1$-C$_6$ alkyl group optionally substituted by one or more halogen atoms, or by one or more CF$_3$ groups;

or the pharmaceutically acceptable addition salts, isomers, enantiomers and diastereoisomers thereof and mixtures thereof.

* * * * *

UNITED STATES PATENT AND TRADEMARK OFFICE
CERTIFICATE OF CORRECTION

PATENT NO. : 9,512,176 B2  
APPLICATION NO. : 13/437491  
DATED : December 6, 2016  
INVENTOR(S) : Potier et al.

It is certified that error appears in the above-identified patent and that said Letters Patent is hereby corrected as shown below:

In the Claims

Column 56,
Composition No. 29 should appear as follows:

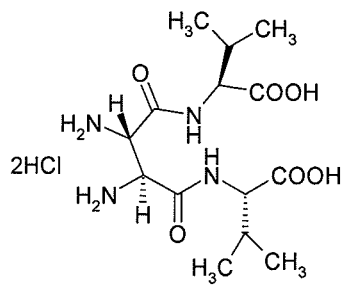

Signed and Sealed this
Third Day of October, 2017

Joseph Matal
*Performing the Functions and Duties of the
Under Secretary of Commerce for Intellectual Property and
Director of the United States Patent and Trademark Office*